US010010594B2

(12) United States Patent
Desrosiers et al.

(10) Patent No.: US 10,010,594 B2
(45) Date of Patent: Jul. 3, 2018

(54) METHODS AND COMPOSITIONS FOR TRANSGENE EXPRESSION IN A HERPESVIRUS VECTOR SYSTEM

(71) Applicants: UNIVERSITY OF MIAMI, Miami, FL (US); PRESIDENT AND FELLOWS OF HARVARD COLLEGE, Cambridge, MA (US)

(72) Inventors: Ronald Desrosiers, Miami, FL (US); Young Shin, Miami, FL (US)

(73) Assignees: UNIVERSITY OF MIAMI, Miami, FL (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/118,421

(22) PCT Filed: Feb. 11, 2015

(86) PCT No.: PCT/US2015/015432

§ 371 (c)(1),
(2) Date: Aug. 11, 2016

(87) PCT Pub. No.: WO2015/123307

PCT Pub. Date: Aug. 20, 2015

(65) Prior Publication Data

US 2017/0165336 A1 Jun. 15, 2017

Related U.S. Application Data

(60) Provisional application No. 61/061,945, filed on Oct. 9, 2014, provisional application No. 62/061,943, filed on Oct. 9, 2014, provisional application No. 61/938,455, filed on Feb. 11, 2014, provisional application No. 61/938,454, filed on Feb. 11, 2014.

(51) Int. Cl.

| | |
|---|---|
| ***A61K 39/00*** | (2006.01) |
| ***A61K 39/21*** | (2006.01) |
| ***A61K 39/04*** | (2006.01) |
| ***C12N 15/869*** | (2006.01) |
| ***A61K 39/015*** | (2006.01) |
| ***A61K 39/12*** | (2006.01) |

(52) U.S. Cl.

CPC ........ *A61K 39/0011* (2013.01); *A61K 39/015* (2013.01); *A61K 39/04* (2013.01); *A61K 39/12* (2013.01); *A61K 39/21* (2013.01); *C12N 15/869* (2013.01); *A61K 2039/5256* (2013.01); *A61K 2039/53* (2013.01); *C12N 2710/16443* (2013.01); *C12N 2740/15034* (2013.01); *C12N 2800/22* (2013.01)

(58) Field of Classification Search

None

See application file for complete search history.

(56) References Cited

U.S. PATENT DOCUMENTS

| | | | |
|---|---|---|---|
| 4,040,388 | A | 8/1977 | Miller |
| 4,469,047 | A | 9/1984 | Miller |
| 4,522,811 | A | 6/1985 | Eppstein et al. |
| 4,593,646 | A | 6/1986 | Miller et al. |
| 4,681,063 | A | 7/1987 | Hebrank |
| 4,968,615 | A | 11/1990 | Koszinowski et al. |
| 5,168,062 | A | 12/1992 | Stinski |
| 5,385,839 | A | 1/1995 | Stinski |
| 5,739,081 | A | 4/1998 | Lloyd et al. |
| 6,156,567 | A | 12/2000 | Fischer |
| 2002/0151033 | A1 | 10/2002 | Knipe et al. |
| 2010/0291127 | A1 | 11/2010 | Eisenbach et al. |
| 2011/0123485 | A1 | 5/2011 | Desrosiers et al. |
| 2012/0076823 | A1 | 3/2012 | Nair et al. |
| 2013/0251747 | A1 | 9/2013 | Audonnet et al. |
| 2013/0337009 | A1 | 12/2013 | Chebloune |

FOREIGN PATENT DOCUMENTS

| | | | |
|---|---|---|---|
| EP | 260148 | A2 | 3/1988 |
| WO | WO-1987/03905 | A1 | 7/1987 |
| WO | WO-1998/00166 | A1 | 1/1998 |
| WO | WO-2005/092374 | A2 | 10/2005 |

OTHER PUBLICATIONS

Fu M. Codon usage bias in herpesvirus. Arch Virol. Mar. 2010;155(3):391-6. Epub Jan. 27, 2010.*

Garber DA, Demma LJ, Staprans SI, Feinberg MB. Simian immunodeficiency virus clone RCr003.09 envelope glycoprotein (env) gene, complete cds. GenBank: FJ804604.1, Pub. Apr. 18, 2009.*

Karlin S, Blaisdell BE, Schachtel GA. Contrasts in codon usage of latent versus productive genes of Epstein-Barr virus: data and hypotheses. J Virol. Sep. 1990;64(9):4264-73.*

Argnani et al., Replication-competent herpes simplex vectors: design and applications, *Gene Ther*., 12:S170-7 (2005).

Bilello et al., A genetic system for rhesus monkey rhadinovirus: use of recombinant virus to quantitate antibody-mediated neutralization, *J. Virol*., 80:1549-62 (2006).

Bilello et al., Extreme dependence of gH and gL expression on ORF57 and association with highly unusual codon usage in rhesus monkey rhadinovirus, *J. Virol*., 82:7231-7 (2008).

Bilello et al., Vaccine protection against simian immunodeficiency virus in monkeys using recombinant gamma-2 herpesvirus, *J. Virol*., 85:12708-20 (2011).

Blissenbach et al., Nuclear RNA export and packaging functions of HIV-1 Rev revisited, *J. Virol*., 84:6598-604 (2010).

(Continued)

*Primary Examiner* — Rachel B Gill

(74) *Attorney, Agent, or Firm* — Marshall, Gerstein & Borun LLP

(57) ABSTRACT

Compositions are provided comprising a replication-competent herpesvirus vector system and/or a herpesvirus vector particle comprising a heterologous recombinant transgene of interest encoding an antigen of interest (e.g., a tumor-associated antigen, a microbial antigen, etc.), wherein the recombinant transgene has been modified to comprise a codon usage signature of a herpesvirus late gene operably linked to an active promoter. Such compositions find use in a variety of methods including, for example, methods of generating an immune response against an antigen of interest in a subject in need thereof, as well as methods for treating or preventing cancer or a microbial infection.

43 Claims, 46 Drawing Sheets

(56) References Cited

OTHER PUBLICATIONS

Brandt et al., Rev proteins of human and simian immunodeficiency virus enhance RNA encapsidation, *PLoS pathogens*, 3(4):e54 (2007).
Bustos et al., Evolution of the Schlafen genes, a gene family associated with embryonic lethality, meiotic drive, immune processes and orthopoxvirus virulence, *Gene*, 447:1-11 (2009).
Chang et al., Regulation by HIV Rev depends upon recognition of splice sites, *Cell*, 59:789-95 (1989).
Cochrane et al., Specific interaction of the human immunodeficiency virus Rev protein with a structured region in the env mRNA, *Proc. Nat. Acad. Sci. USA*, 87:1198-202 (1990).
D'Agostino et al., The Rev protein of human immunodeficiency virus type 1 promotes polysomal association and translation of gag/pol and vpu/env mRNAs, *Molec. Cell. Biol.*, 12:1375-86 (1992).
Felber et al., Rev protein of human immunodeficiency virus type 1 affects the stability and transport of the viral mRNA, *Proc. Nat. Acad. Sci. USA*, 86:1495-99 (1989).
Fuhrmann et al., Monitoring dynamic expression of nuclear genes in Chlamydomonas reinhardtii by using a synthetic luciferase reporter gene, *Plant molec. Biol.*, 55:869-81 (2004).
Gillet et al., Development of bovine herpesvirus 4 as an expression vector using bacterial artificial chromosome cloning, *J. Gen. Biol.*, 4:907-17(2004).
Groom et al., Beyond nuclear export, *J. General virology*, 90:1303-18 (2009).
Hamrnarskjold et al. Regulation of human immunodeficiency virus env expression by the rev gene product, *J. Virol.*, 63:1959-66 (1989).
Hansen et al. Effector memory T cell responses are associated with protection of rhesus monkeys from mucosal simian immunodeficiency virus challenge, *Nature medicine*, 15:293-9 (2009).
Hansen et al. Profound early control of highly pathogenic SIV by an effector memory T-cell vaccine, *Nature*, 473:523-7 (2011).
Kirshner et al., Kaposi's sarcoma-associated herpesvirus open reading frame 57 encodes a posttranscriptional regulator with multiple distinct activities, *J. Virol.*, 74:3586-97 (2000).
Kwissa et al., Efficient vaccination by intradermal or intramuscular inoculation of plasmid DNA expressing hepatitis B surface antigen under desmin promoter/enhancer control, Vaccine, 8(18):2337-44 (2000).
Langer, New methods of drug delivery, *Science*, 249:1527-33 (1990).
Li et al. Codon-usage-based inhibition of HIV protein synthesis by human schlafen 11, *Nature*, 491:125-8 (2012).
Lu et al., U1 small nuclear RNA plays a direct role in the formation of a rev-regulated human immunodeficiency virus env mRNA that remains unspliced, *Proc. Nat. Acad. Sci. USA*, 7598-602 (1990).
Lukac et al., Transcriptional activation by the product of open reading frame 50 of Kaposi's sarcoma-associated herpesvirus is required for lytic viral reactivation in B cells, *J. Virol.*, 73:9348-61 (1999).
Malik et al., The evolutionarily conserved Kaposi's sarcoma-associated herpesvirus ORF57 protein interacts with REF protein and acts as an RNA export factor, *J. Biol. Chem.*, 279:33001-11 (2004).
Malim et al. HIV-1 structural gene expression requires binding of the Rev trans-activator to its RNA target sequence, *Cell*, 60:675-83 (1990).
Malim et al., The HIV-1 rev trans-activator acts through a structured target sequence to activate nuclear export of unspliced viral mRNA, *Nature*, 338:254-57 (1989).
Martinez-Navio et al., Neutralizing capacity of monoclonal antibodies that recognize peptide sequences underlying the carbohydrates on gp41 of simian immunodeficiency virus, *J. Virol.*, 86:12484-93 (2012).
Meignier et al., In vivo behavior of genetically engineered herpes simplex viruses R7017 and R7020. II. Studies in immunocompetent and immunosuppressed owl monkeys (*Aotus trivirgatus*), *J. Infect. Dis.*, 162:313-21 (1990).
Nekorchuk et al., Kaposi's sarcoma-associated herpesvirus ORF57 protein enhances mRNA accumulation independently of effects on nuclear RNA export, *J. Virol.*, 81:9990-8 (2007).
Perales et al., Regulation of HIV-1 env mRNA translation by Rev protein, *Biochimica. Biophys. Acta*, 1743:169-75 (2005).
Pilkington et al., Kaposi's sarcoma-associated herpesvirus ORF57 is not a bona fide export factor, *J. Virol.*, 86:13089-94 (2012).
Prichard et al., Evaluation of AD472, a live attenuated recombinant herpes simplex virus type 2 vaccine in guinea pigs, *Vaccine*, 23:5424-31 (2005).
Ruvolo et al., The Epstein-Barr virus nuclear protein SM is both a post-transcriptional inhibitor and activator of gene expression, *Proc. Nat. Acad. Sci. USA*, 95:8852-7 (1998).
Sahin et al., Kaposi's sarcoma-associated herpesvirus ORF57 protein binds and protects a nuclear noncoding RNA from cellular RNA decay pathways, *PLoS pathogens*, 6:e1000799 (2010).
Sandri-Goldin et al., A herpesvirus regulatory protein appears to act post-transcriptionally by affecting mRNA processing, *Genes& Devel.*, 6:848-63 (1992).
Shin et al., Rhesus monkey rhadinovirus 'ORF57 induces gH and gL glycoprotein expression through posttranscriptional accumulation of target mRNAs, *J. Virol*, 85(15):7810-7 (2011).
Spector, Evaluation of a live attenuated recombinant virus RAV 9395 as a herpes simplex virus type 2 vaccine in guinea pigs, *J. Infect. Dis.*, 177:1143-54 (1998).
Sun et al., A viral gene that activates lytic cycle expression of Kaposi's sarcoma-associated Herpesvirus, *Proc. Nat. Acad. Sci. USA*, 95:10866-71 (1998).
Williams et al., The prototype gamma-2 herpesvirus nucleocytoplasmic shuttling protein, ORF 57, transports viral RNA through the cellular mRNA export pathway, *Biochem. J.*, 387: 295-308 (2005).
Zalani et al., Epstein-Barr viral latency is disrupted by the immediate-early BRLF1 protein through a cell-specific mechanism, *Proc. Nat. Acad. Sci. USA*, 93:9194-9 (1996).
International Search Report and Written Opinion of the International Search Authority, United States Patent Office, PCT/US2015/015432, dated Apr. 24, 2015.
International Preliminary Report on Patentability, United States Patent Office, PCT/US2015/015432, dated Aug. 16, 2016.

* cited by examiner

Figure 1F 1210 1220 1230 1240
SIV_gp160-wild_type TACTGTAAAATGAATTGGTTTCTAAATTGGGTAGAAGAT[illegible]
SIV_gp160-codon_alted TACTGTAAAATGAATTGGTTTCTAAATTGGGTAGAAGAT[illegible]

1250 1260 1270 1280
SIV_gp160-wild_type G[illegible]AATACAGCTAACCAGAAGCCAAAGGAACAGCATAAA[illegible]G
SIV_gp160-codon_alted G[illegible]AATACAGCTAACCAGAAGCCAAAGGAACAGCATAAA[illegible]G 1290 1300 1310 1320
SIV_gp160-wild_type [illegible]AATTACGTGCCATGTCATATTAGACAAATAATCAACAC[illegible]
SIV_gp160-codon_alted [illegible]AATTACGTGCCATGTCATATTAGACAAATAATCAACAC[illegible]

1330 1340 1350 1360
SIV_gp160-wild_type TGGCATAAAGTAGGCAAAAATGTTTATTTGCC[illegible]CCAAGAG
SIV_gp160-codon_alted TGGCATAAAGTAGGCAAAAATGTTTATTTGCC[illegible]CCAAGAG 1370 1380 1390 1400
SIV_gp160-wild_type A[illegible]GGAGAC[illegible]T[illegible]ACGTGTAACTCCACAGTGACCAGT[illegible]T[illegible]AT
SIV_gp160-codon_alted A[illegible]GGAGAC[illegible]T[illegible]ACGTGTAACTCCACAGTGACCAGT[illegible]T[illegible]AT 1410 1420 1430 1440
SIV_gp160-wild_type AGCAAACATAGATTGGATTGATGGAAACCAAAC[illegible]AATATC
SIV_gp160-codon_alted AGCAAACATAGATTGGATTGATGGAAACCAAAC[illegible]AATATC

Figure 1H

| | 1690 | 1700 | 1710 | 1720 |
|---|---|---|---|---|
| SIV_gp160-wild_type | ATAGTGCAGC | AACAGCAACA | GCTGTTGGAC | GTGGTCAAGA |
| SIV_gp160-codon_alted | ATAGTGCAGC | AACAGCAACA | GCTGTTGGAC | GTGGTCAAGA |

| | 1730 | 1740 | 1750 | 1760 |
|---|---|---|---|---|
| SIV_gp160-wild_type | GACAACAAGA | ATTGTTGCGA | CTGACCGTCT | GGGGAACAAA |
| SIV_gp160-codon_alted | GACAACAAGA | ATTGTTGCGA | CTGACCGTCT | GGGGAACAAA |

| | 1770 | 1780 | 1790 | 1800 |
|---|---|---|---|---|
| SIV_gp160-wild_type | GAACCTCCAG | ACTAGGGTCA | CTGCCATCGA | GAAGTACTTA |
| SIV_gp160-codon_alted | GAACCTCCAG | ACTAGGGTCA | CTGCCATCGA | GAAGTACTTA |

| | 1810 | 1820 | 1830 | 1840 |
|---|---|---|---|---|
| SIV_gp160-wild_type | AAGGACCAGG | CGCAGCTGAA | TGCTTGGGGA | TGTGCGTTTA |
| SIV_gp160-codon_alted | AAGGACCAGG | CGCAGCTGAA | TGCTTGGGGA | TGTGCGTTTA |

| | 1850 | 1860 | 1870 | 1880 |
|---|---|---|---|---|
| SIV_gp160-wild_type | GACAAGTCTG | CCACACTACT | GTACCATGGC | CAAATGCAAG |
| SIV_gp160-codon_alted | GACAAGTCTG | CCACACTACT | GTACCATGGC | CAAATGCAAG |

| | 1890 | 1900 | 1910 | 1920 |
|---|---|---|---|---|
| SIV_gp160-wild_type | TCTAACACCA | AAGTGGAACA | ATGAGACTTG | GCAAGAGTGG |
| SIV_gp160-codon_alted | TCTAACACCA | AAGTGGAACA | ATGAAACATG | GCAAGAATGG |

Figure 2A

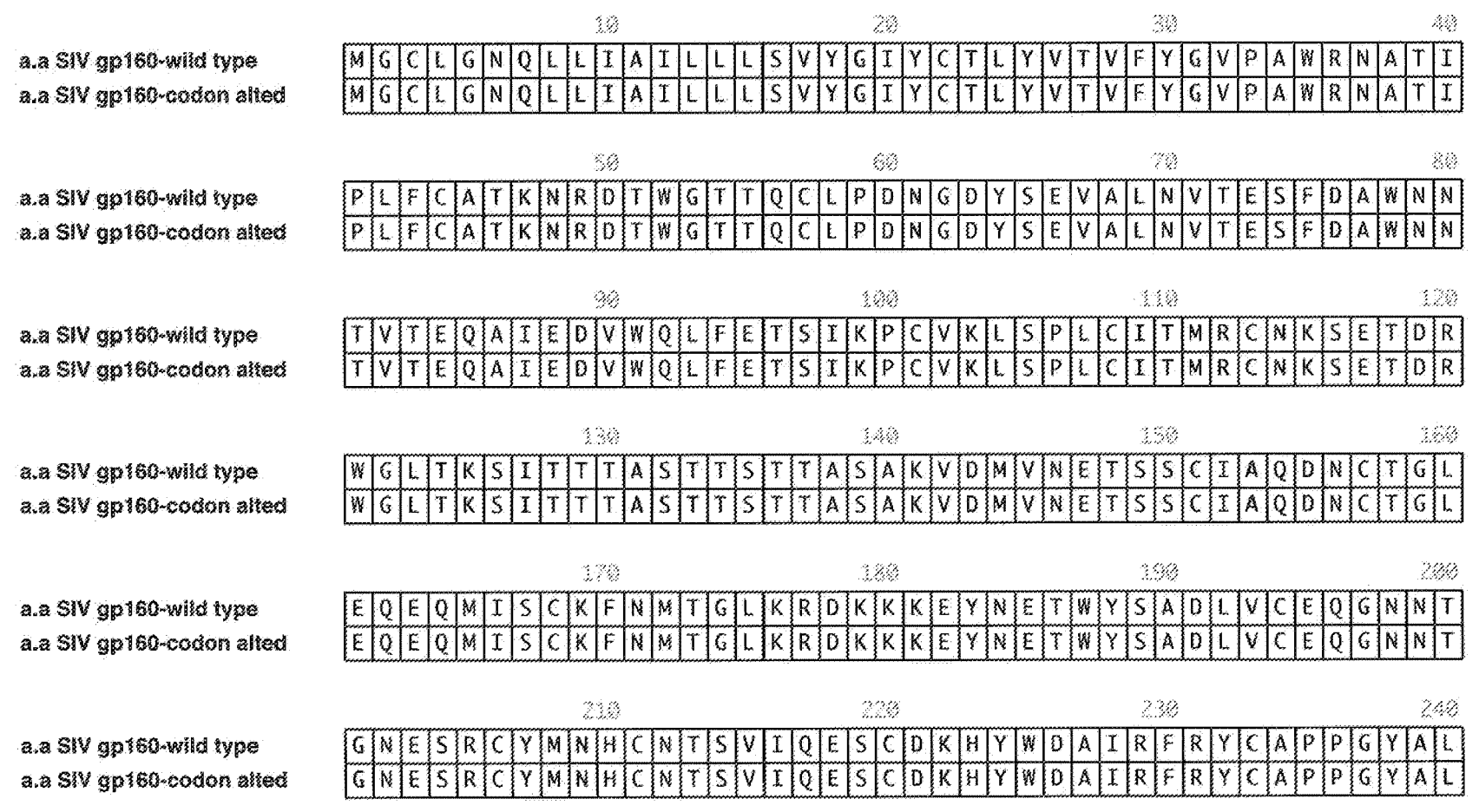

| | 10 20 30 40 |
|---|---|
| a.a SIV gp160-wild type | MGCLGNQLLIAILLLSVYGIYCTLYVTVFYGVPAWRNATI |
| a.a SIV gp160-codon alted | MGCLGNQLLIAILLLSVYGIYCTLYVTVFYGVPAWRNATI |

| | 50 60 70 80 |
|---|---|
| a.a SIV gp160-wild type | PLFCATKNRDTWGTTQCLPDNGDYSEVALNVTESFDAWNN |
| a.a SIV gp160-codon alted | PLFCATKNRDTWGTTQCLPDNGDYSEVALNVTESFDAWNN |

| | 90 100 110 120 |
|---|---|
| a.a SIV gp160-wild type | TVTEQAIEDVWQLFETSIKPCVKLSPLCITMRCNKSETDR |
| a.a SIV gp160-codon alted | TVTEQAIEDVWQLFETSIKPCVKLSPLCITMRCNKSETDR |

| | 130 140 150 160 |
|---|---|
| a.a SIV gp160-wild type | WGLTKSITTTASTTSTTASAKVDMVNETSSCIAQDNCTGL |
| a.a SIV gp160-codon alted | WGLTKSITTTASTTSTTASAKVDMVNETSSCIAQDNCTGL |

| | 170 180 190 200 |
|---|---|
| a.a SIV gp160-wild type | EQEQMISCKFNMTGLKRDKKKEYNETWYSADLVCEQGNNT |
| a.a SIV gp160-codon alted | EQEQMISCKFNMTGLKRDKKKEYNETWYSADLVCEQGNNT |

| | 210 220 230 240 |
|---|---|
| a.a SIV gp160-wild type | GNESRCYMNHCNTSVIQESCDKHYWDAIRFRYCAPPGYAL |
| a.a SIV gp160-codon alted | GNESRCYMNHCNTSVIQESCDKHYWDAIRFRYCAPPGYAL |

Figure 2B

| | 250 | 260 | 270 | 280 |
|---|---|---|---|---|
| a.a SIV gp160-wild type | LRCNDTNYSG | FMPKCSKVVV | SSCTRMMETQ | TSTWFGFNGT |
| a.a SIV gp160-codon alted | LRCNDTNYSG | FMPKCSKVVV | SSCTRMMETQ | TSTWFGFNGT |

| | 290 | 300 | 310 | 320 |
|---|---|---|---|---|
| a.a SIV gp160-wild type | RAENRTYIYW | HGRDNRTIIS | LNKYYNLTMK | CRRPGNKTVL |
| a.a SIV gp160-codon alted | RAENRTYIYW | HGRDNRTIIS | LNKYYNLTMK | CRRPGNKTVL |

| | 330 | 340 | 350 | 360 |
|---|---|---|---|---|
| a.a SIV gp160-wild type | PVTIMSGLVF | HSQPINDRPK | QAWCWFGGKW | KDAIKEVKQT |
| a.a SIV gp160-codon alted | PVTIMSGLVF | HSQPINDRPK | QAWCWFGGKW | KDAIKEVKQT |

| | 370 | 380 | 390 | 400 |
|---|---|---|---|---|
| a.a SIV gp160-wild type | IVKHPRYTGT | NNTDKINLTA | PGGGDPEVTF | MWTNCRGEFL |
| a.a SIV gp160-codon alted | IVKHPRYTGT | NNTDKINLTA | PGGGDPEVTF | MWTNCRGEFL |

| | 410 | 420 | 430 | 440 |
|---|---|---|---|---|
| a.a SIV gp160-wild type | YCKMNWFLNW | VEDRNTANQK | PKEQHKRNYV | PCHIRQIINT |
| a.a SIV gp160-codon alted | YCKMNWFLNW | VEDRNTANQK | PKEQHKRNYV | PCHIRQIINT |

| | 450 | 460 | 470 | 480 |
|---|---|---|---|---|
| a.a SIV gp160-wild type | WHKVGKNVYL | PPREGDLTCN | STVTSLIANI | DWIDGNQTNI |
| a.a SIV gp160-codon alted | WHKVGKNVYL | PPREGDLTCN | STVTSLIANI | DWIDGNQTNI |

Figure 2C

```
                             490       500       510       520
a.a SIV gp160-wild type      TMSAEVAELYRLELGDYKLVEITPIGLAPTDVKRYTTGGT
a.a SIV gp160-codon alted    TMSAEVAELYRLELGDYKLVEITPIGLAPTDVKRYTTGGT

                             530       540       550       560
a.a SIV gp160-wild type      SRNKRGVFVLGFLGFLATAGSAMGAASLTLTAQSRTLLAG
a.a SIV gp160-codon alted    SRNKRGVFVLGFLGFLATAGSAMGAASLTLTAQSRTLLAG

                             570       580       590       600
a.a SIV gp160-wild type      IVQQQQQLLDVVKRQQELLRLTVWGTKNLQTRVTAIEKYL
a.a SIV gp160-codon alted    IVQQQQQLLDVVKRQQELLRLTVWGTKNLQTRVTAIEKYL

                             610       620       630       640
a.a SIV gp160-wild type      KDQAQLNAWGCAFRQVCHTTVPWPNASLTPKWNNETWQEW
a.a SIV gp160-codon alted    KDQAQLNAWGCAFRQVCHTTVPWPNASLTPKWNNETWQEW

                             650       660       670       680
a.a SIV gp160-wild type      ERKVDFLEENITALLEEAQIQQEKNMYELQKLNSWDVFGN
a.a SIV gp160-codon alted    ERKVDFLEENITALLEEAQIQQEKNMYELQKLNSWDVFGN

                             690       700       710       720
a.a SIV gp160-wild type      WFDLASWIKYIQYGVYIVVGVILLRIVIYIVQMLAKLRQG
a.a SIV gp160-codon alted    WFDLASWIKYIQYGVYIVVGVILLRIVIYIVQMLAKLRQG
```

Figure 2D

```
                               730       740       750       760
a.a SIV gp160-wild type     YRPVFSSPPSYFQQTHIQQDPALPTREGKERDGGEGGGNS
a.a SIV gp160-codon alted   YRPVFSSPPSYFQQTHIQQDPALPTREGKERDGGEGGGNS

                               770       780       790       800
a.a SIV gp160-wild type     SWPWQIEYIHFLIRQLIRLLTWLFSNCRTLLSRVYQILQP
a.a SIV gp160-codon alted   SWPWQIEYIHFLIRQLIRLLTWLFSNCRTLLSRVYQILQP

                               810       820       830       840
a.a SIV gp160-wild type     ILQRLSATLQRIREVLRTELTYLQYGWSYFHEAVQAVWRS
a.a SIV gp160-codon alted   ILQRLSATLQRIREVLRTELTYLQYGWSYFHEAVQAVWRS

                               850       860       870
a.a SIV gp160-wild type     ATETLAGAWGDLWETLRRGGRWILAIPRRIRQGLELTLL
a.a SIV gp160-codon alted   ATETLAGAWGDLWETLRRGGRWILAIPRRIRQGLELTLL
```

Codon changes in SIVgp160

| Amino Acid | Changed from | %in gH | %in gp160 | %in human | Changed into | %in gH | %in gp160 | %in human | Number of changes |
|---|---|---|---|---|---|---|---|---|---|
| **Arg** | AGG | 15 | 38 | 21 | CGT | 19 | 0 | 8 | 18 |
| **Glu** | GAG | 13 | 51 | 58 | GAA | 87 | 49 | 42 | 23 |
| **Pro** | CCT | 19 | 19 | 29 | CCG | 39 | 6 | 11 | 6 |
| **Thr** | ACT | 12 | 40 | 25 | ACG | 26 | 6 | 11 | 25 |
| **Leu** | CTC | 1 | 19 | 20 | TTA | 32 | 16 | 8 | 14 |
| **Gly** | GGG | 0 | 18 | 25 | GGA | 62 | 41 | 25 | 7 |
| | | | | | | | | | 93/880 (10.5 %) |

FIG. 4

Figure 6: Expression of SIVmac239-SD-gp160

N: non-optimized (n.o) gp160

D: deoptimized (d.o) gp160 with intact RRE

1. SD-expression optimized (e.o) gp160
2. SD-nonoptimized (n.o) gp160
3. SD-deoptimized (d.o) gH-like gp160

Codon changes in gH (gp160-like)

| Amino Acid | Changed into | %in gH | %in gp160 | %in human | Changed from | %in gH | %in gp160 | %in human | Number of changes |
|---|---|---|---|---|---|---|---|---|---|
| **Arg** | AGG | 15 | 38 | 21 | CGT | 19 | 0 | 8 | 5 |
| **Glu** | GAG | 13 | 51 | 58 | GAA | 87 | 49 | 42 | 33 |
| **Pro** | CCT | 19 | 19 | 29 | CCG | 39 | 6 | 11 | 12 |
| **Thr** | ACT | 12 | 40 | 25 | ACG | 26 | 6 | 11 | 11 |
| **Leu** | CTC | 1 | 19 | 20 | TTA | 32 | 16 | 8 | 27 |
| **Gly** | GGG | 0 | 18 | 25 | GGA | 62 | 41 | 25 | 16 |
| | | | | | | | | | 104/726 (14.3 %) |

FIG. 13

Neutralization assay of RRV-SIV env sera against SIV 316

METHODS AND COMPOSITIONS FOR TRANSGENE EXPRESSION IN A HERPESVIRUS VECTOR SYSTEM

CROSS-REFERENCE TO RELATED APPLICATIONS

This application claims priority to and the benefit of U.S. Provisional Application No. 61/938,455, filed Feb. 11, 2014, U.S. Provisional Application No. 62/061,945, filed Oct. 9, 2014, U.S. Provisional Application No. 61/938,454, filed Feb. 11, 2014, and U.S. Provisional Application No. 62/061,943, filed Oct. 9, 2014, which are hereby incorporated herein by reference in their entireties.

STATEMENT OF U.S. GOVERNMENTAL INTEREST

This invention was made with government support under AI063928 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 11, 2015, is named 7230-186WO_SL.txt and is 24,620 bytes in size.

FIELD OF THE INVENTION

The present invention is directed to a method for the delivery and expression of a polynucleotide of interest via a herpesvirus vector system.

BACKGROUND OF THE INVENTION

Herpesviruses represent a group of double-stranded DNA viruses distributed widely within the animal kingdom. Various forms of genetic engineering have been performed on herpesviruses which has resulted in the construction of viral vectors in which the viral genome contains deletions/modifications of certain genomic sequences and further comprises heterologous nucleic acid (e.g., DNA) sequences. Such viral vectors can infect a target cell and express the heterologous sequence. In effect, the virus becomes an elaborate delivery system for the heterologous nucleic acid sequence of interest. Such compositions find particular use in the fields of gene therapy, drug delivery and vaccine development.

Methods continue to be needed in the art to improve the herpesvirus vector systems and their ability to express nucleic acid sequences of interest.

SUMMARY OF THE INVENTION

Compositions comprising a replication-competent herpesvirus vector system and/or a herpesvirus vector particle are provided. The various replication-competent herpesvirus vectors and particles provided herein comprise a polynucleotide comprising a heterologous recombinant transgene of interest operably linked to a promoter, wherein the recombinant transgene has been modified to comprise a codon usage signature of at least one herpesvirus late gene. Such compositions find use in a variety of methods including, for example, methods of generating an immune response against an antigen of interest in a subject in need thereof and methods for treating or preventing cancer and microbial infection comprising administering to a subject a therapeutically effective amount of the replication competent herpesvirus particle disclosed herein.

BRIEF DESCRIPTION OF THE DRAWINGS

FIG. 2 provides an alignment of the SIVgp160 wild type polypeptide (SEQ ID NO: 2) aligned with the codon-altered SIVgp160 polypeptide (SEQ ID NO: 4).

FIG. 4 provides a summary of the codon changes made to SIVgp160.

FIG. 12 discloses SEQ ID NO: 5.

FIG. 13 provides a summary of the codon changes made to gH (gp160-like).

FIG. 16*a*: Comparison of codon usage in SIV gp160 and RRV gH. The usage of each indicated codon in RRV gH as % of all codons for that particular amino acid is plotted vs. that for gp160 using a XY scatter plot with a linear regression line and a coefficient of determination ($R^2$). Codons with the most skewed usage between the two sequences are those most appreciably removed from the regression line. To generate a codon-modified (gH-like) SIV gp160, some codons of SIV gp160 (colored circles with x mark) were changed into corresponding synonymous codons (colored circles) to reflect the codon usage of RRV gH. To generate a codon-modified (gp160-like) RRV gH, codon changes were performed in the exact opposite direction. FIG. 16*b*: Schematic representation of expression cassettes with the codon-modified (gH-like) SIV gp160 and codon-modified (gp160-like) RRV gH sequence. Rev exon1, splicing donor (SD) sequence (indicated by *, aaacaagtaagt (SEQ ID NO: 6)), and rev-response element (RRE) are shown. Each codon change is represented by a vertical line above the box. FIG. 16*c*: Expression cassettes of gp160 with the unmodified (U) (lanes 1, 3, and 5), and codon-modified (M, gH-like) SIV gp160 sequence (lanes 2, 4, and 6) were transfected into 293T cells together with either control, rev, or orf57 expression plasmid. The expression of gp160 was detected using kk41 antibody. The expression of orf57 and rev was detected using a v5 antibody. FIG. 16*d*: Expression cassettes of gH with the unmodified (U) or codon-modified (M, gp160-like) RRV gH sequence with or without flanking splicing donor (SD, ctaatacatcttctgcatcaaacaagtaagt (SEQ ID NO: 5)) and RRE sequences was transfected into 293T cells together with either control, rev, or orf57 expression plasmid. The expressions of RRV gH, orf57, and rev were detected using a v5 antibody.

FIG. 18*a*: Induction of gp160 from the expression cassette with the unmodified SIV gp160 sequence by rev and its abrogation by schlafens. FIG. 18*b*: Induction of gp160 from the expression cassette with the codon-modified (gH-like) SIV gp160 sequence by orf57 and its abrogation by schlafens. The band indicated by * is a degradation product of orf57. FIG. 18*c*: Schlafen 14 inhibits rev-mediated rescue of gp160 expression from the expression cassette with the unmodified (U) SIV gp160 sequence in a dose-dependent manner. FIG. 18*d*: Schlafen 14 inhibits orf57-mediated rescue of gp160 expression from the expression cassette with the codon-modified (M) SIV gp160 (gH-like) sequence in a dose-dependent manner. FIG. 18*e*: Rev rescues schlafen 14-mediated inhibition of gp160 expression from the expression cassette with the unmodified gp160 sequence in a dose-dependent manner. FIG. 18*f*: Orf57 rescues schlafen 14-mediated inhibition of gp160 expression from the expression cassette with the codon-modified (gH-like) gp160 sequence in a dose-dependent manner.

FIG. 19*a*: Rev and orf57 from transfected cells were immunoprecipitated using a mouse v5 antibody. Any co-precipitated schlafen 14 protein in immunoprecipitated fractions was detected using an anti-FLAG antibody. FIG. 19*b*: Streptactin pull-down of rev and orf57 with or without nuclease treatments. Samples were treated with DNase I (D, 3 μl) and RNase A (R, 3 μl) for 30 minutes at 37° C. where indicated. The co-purified schlafen 14 proteins were detected using an anti-FLAG antibody.

FIG. 20*a*: Recombinant RRVs harboring codon-modified (gH-like) gp160 sequence were inoculated into two rhesus macaques ($9\times10^7$ genome copies/animal) and levels of anti-SIV envelope antibodies were measured by an enzyme-linked immunosorbent assay (ELISA). FIG. 20*b*: Neutralization of SIV316 by sera taken at weeks 17 and 33 post-inoculation with rRRV with codon-modified gp160 sequence. SPF denotes negative control sera from specific pathogen free animals.

FIG. 21*a*: The usage (%) of each codon in RRV gH, SIV gp160, simian virus40 (SV40) VP1, human papilloma virus16 (HPV16) L1, or human adenovirus2 (hAV2) fiber was plotted on x axis vs. the codon usage of human exome sequences on Y axis. Also shown is coefficient of determination ($R^2$). Enterovirus C P1 was included as a comparison. FIG. 21*b*: Expression of SV40 VP1 from the unmodified (lane 1) or codon-optimized (lane 2) sequence.

FIG. 22*a*: The change of RNA levels of codon-modified (M, gH-like) gp160 by expression of rev or orf57. Shown below the bar graph were the corresponding protein levels of gp160 measured by a immunoblotting using the part of cell pellets. FIG. 22*b*: The change of RNA levels of unmodified (U) gp160 by expression of rev or orf57. Shown below the bar graph were the corresponding protein levels of gp160 measured by a immunoblotting using the part of cell pellets. FIG. 22*c*: The ratio of gp160 RNA from expression cassette with the unmodified (U) gp160 sequence between cytoplasm (C) and nucleus (N) in transient over-expression. Total RNAs from each compartment were isolated and the amount of SIV gp160-specific RNA was measured by a real time RT-PCR. The ratio of gp160 RNA (cytoplasm over nucleus) was presented with error bars. RNA fractions from each compartment were analyzed by a glyoxal-based agarose gel and it revealed that 32S and 45S RNAs were found only in the nuclear but not cytoplasmic fraction (data not shown).

DETAILED DESCRIPTION OF THE INVENTION

I. Overview

Figure 1A:
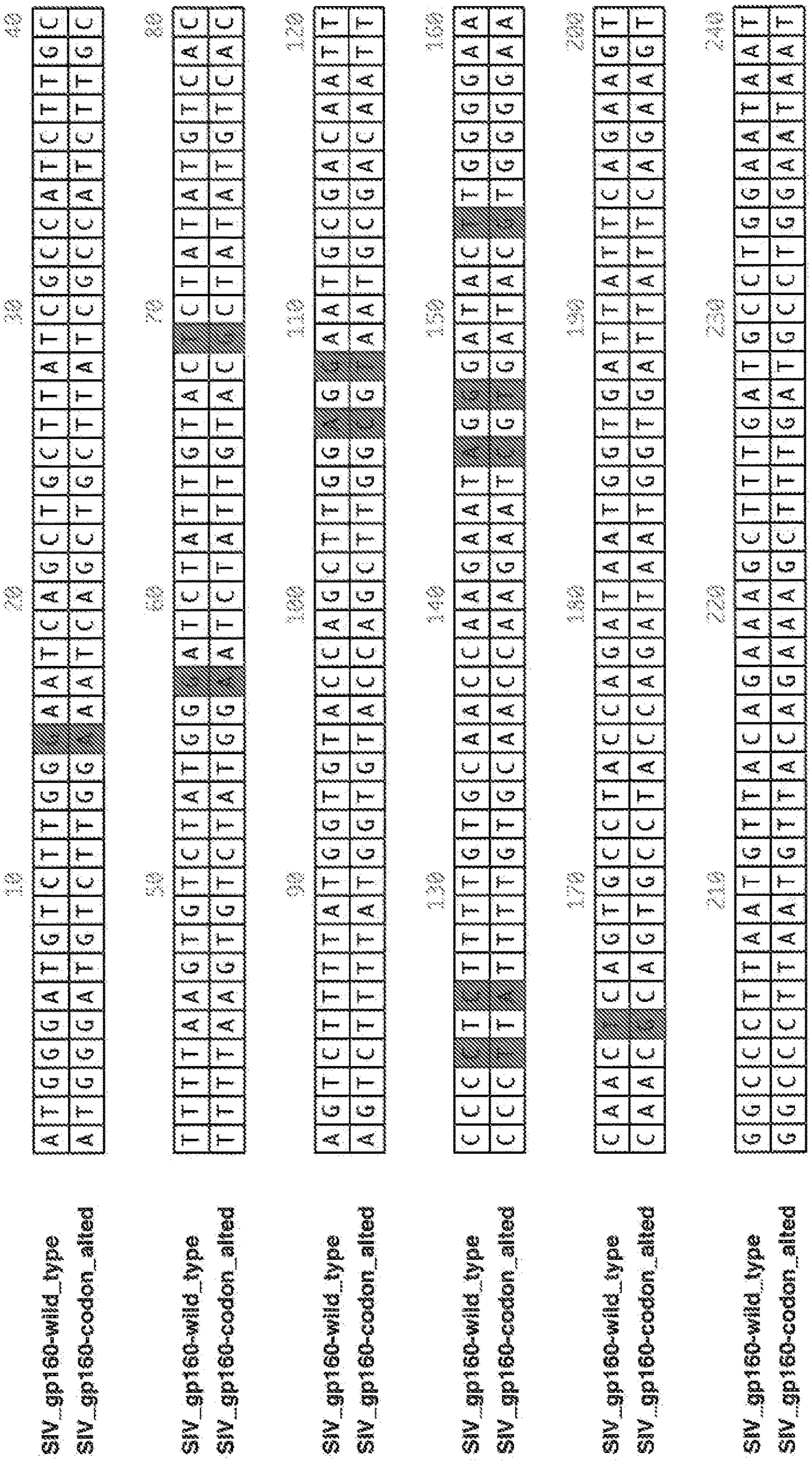
FIG. 1 provides an alignment of the SIVgp160 wild type nucleotide sequence (SEQ ID NO: 1) aligned with the codon-altered SIVgp160 nucleotide sequence (SEQ ID NO: 3).
Figure 1B:
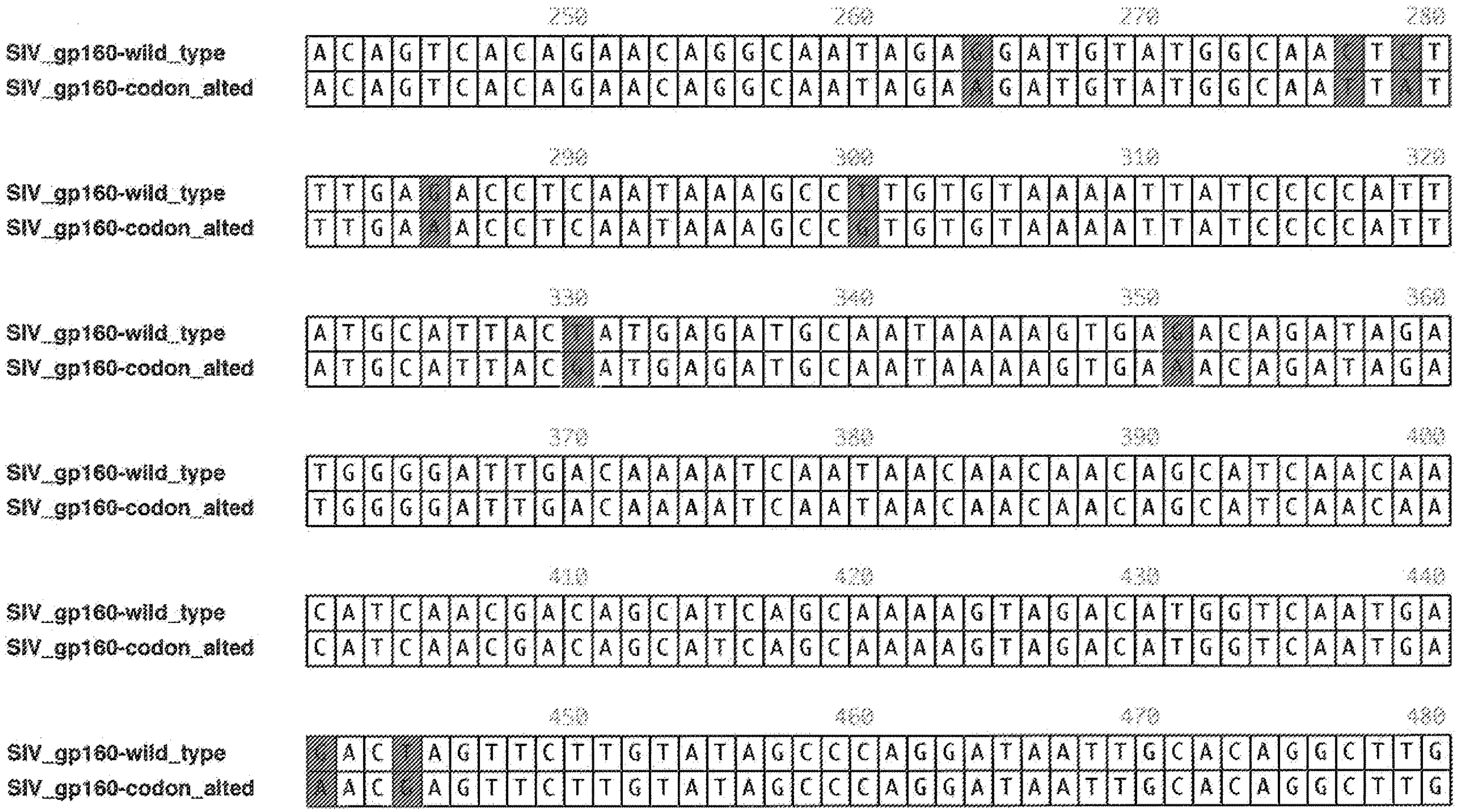
Figure 1C:
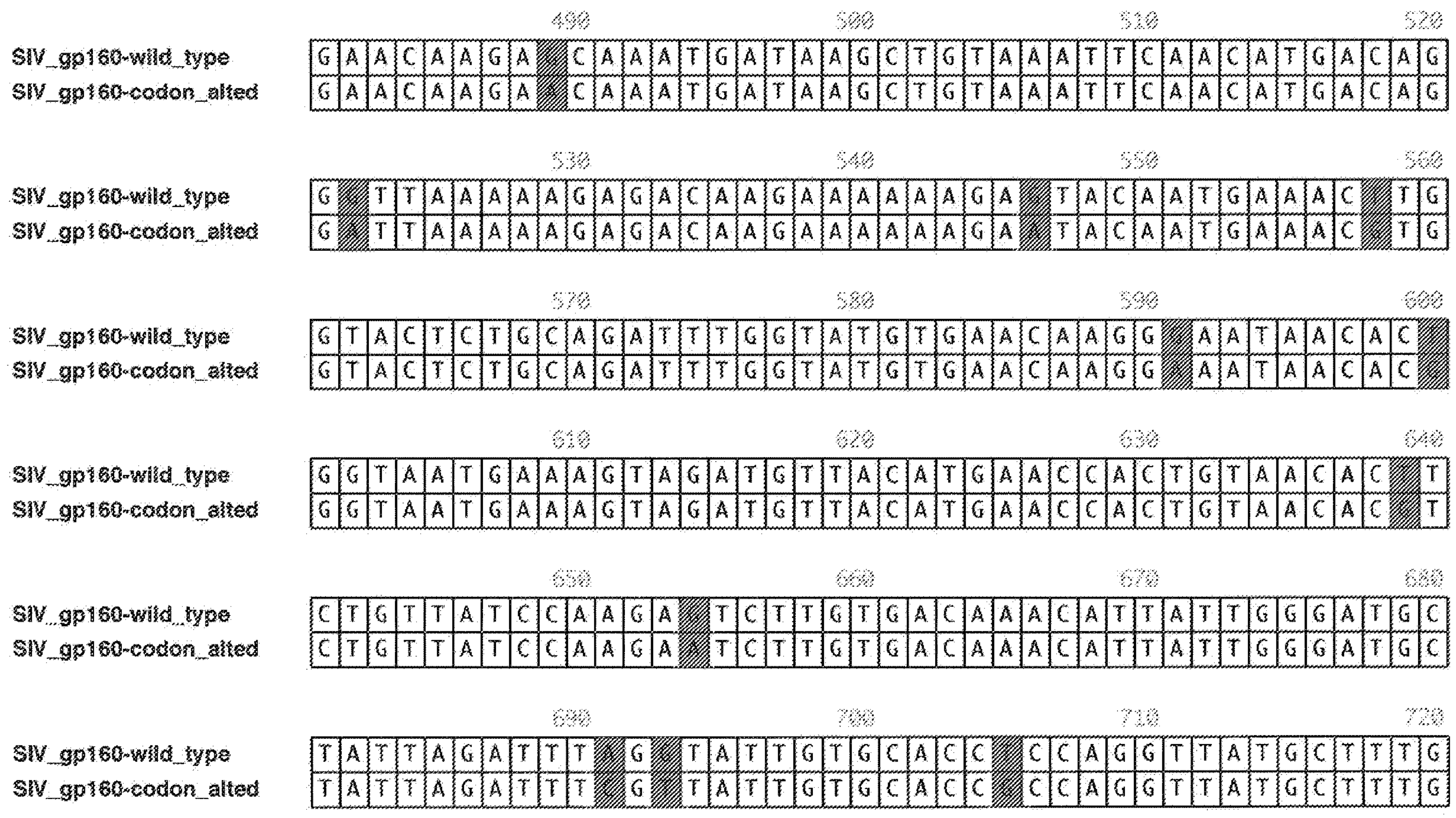
Figure 1D:
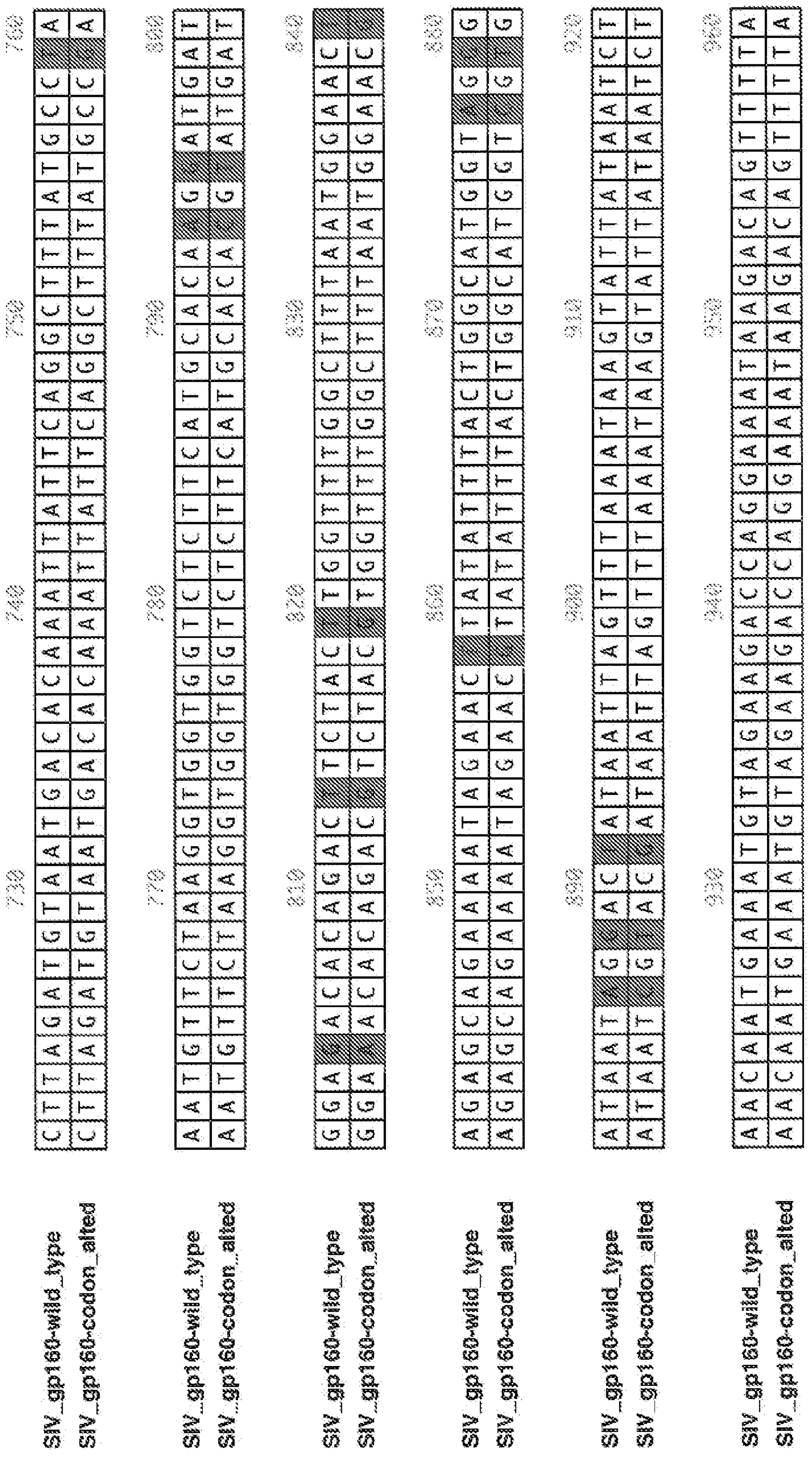
Figure 1E:
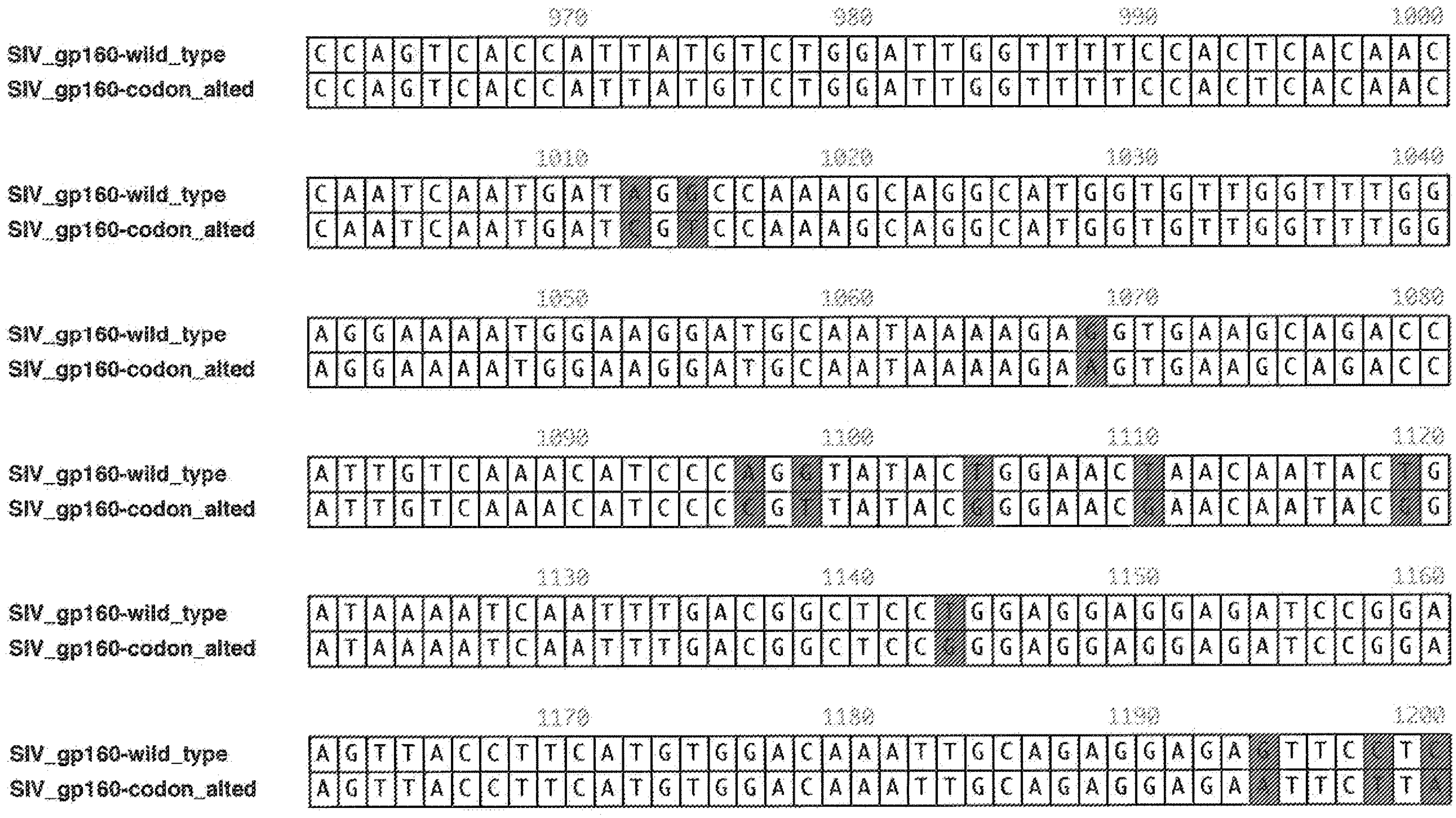
Figure 1G:
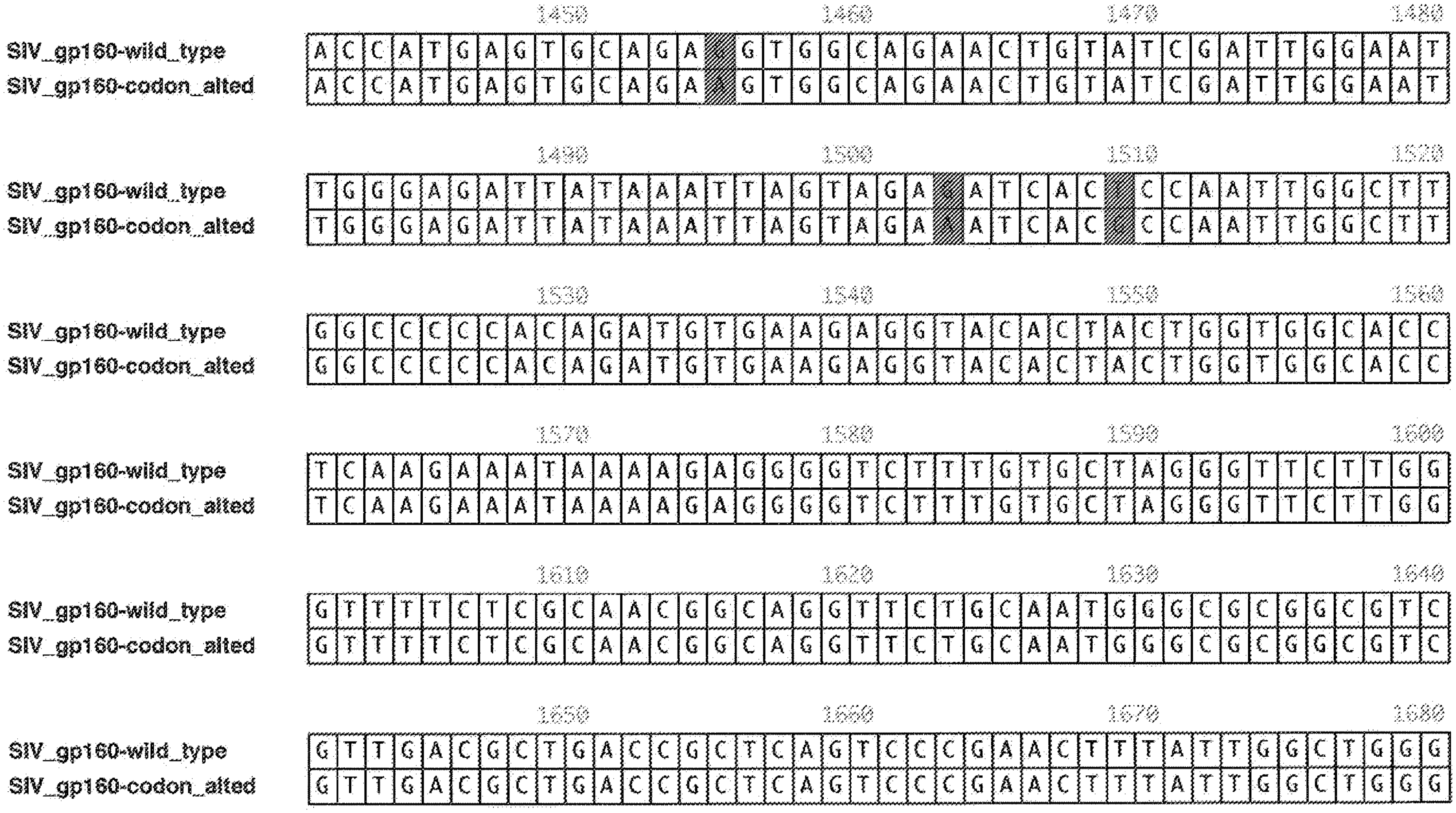
Figure 11:
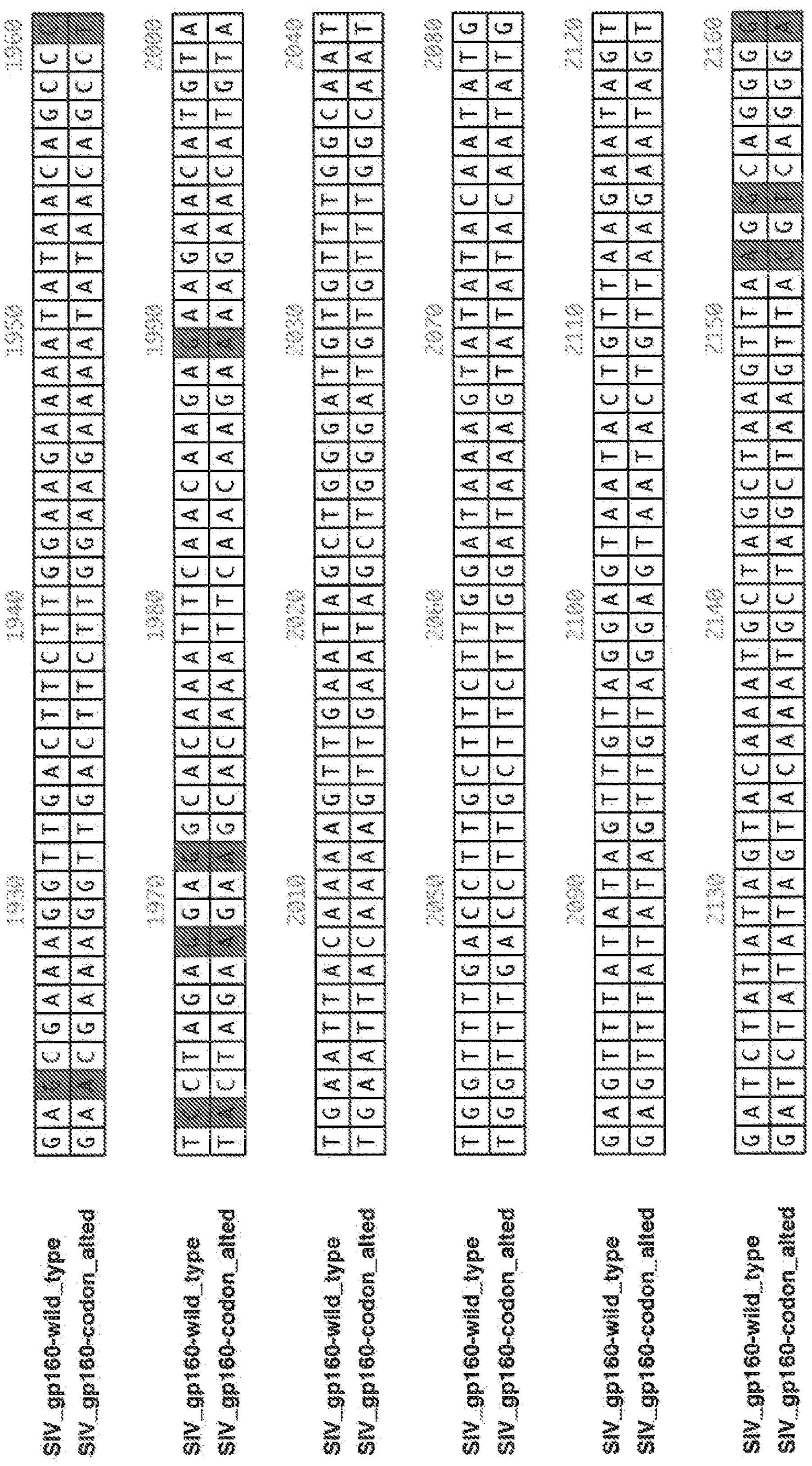
FIG. 11 shows the codon usage of SIVgp160 verses that of RRV gH.
Figure 1J:
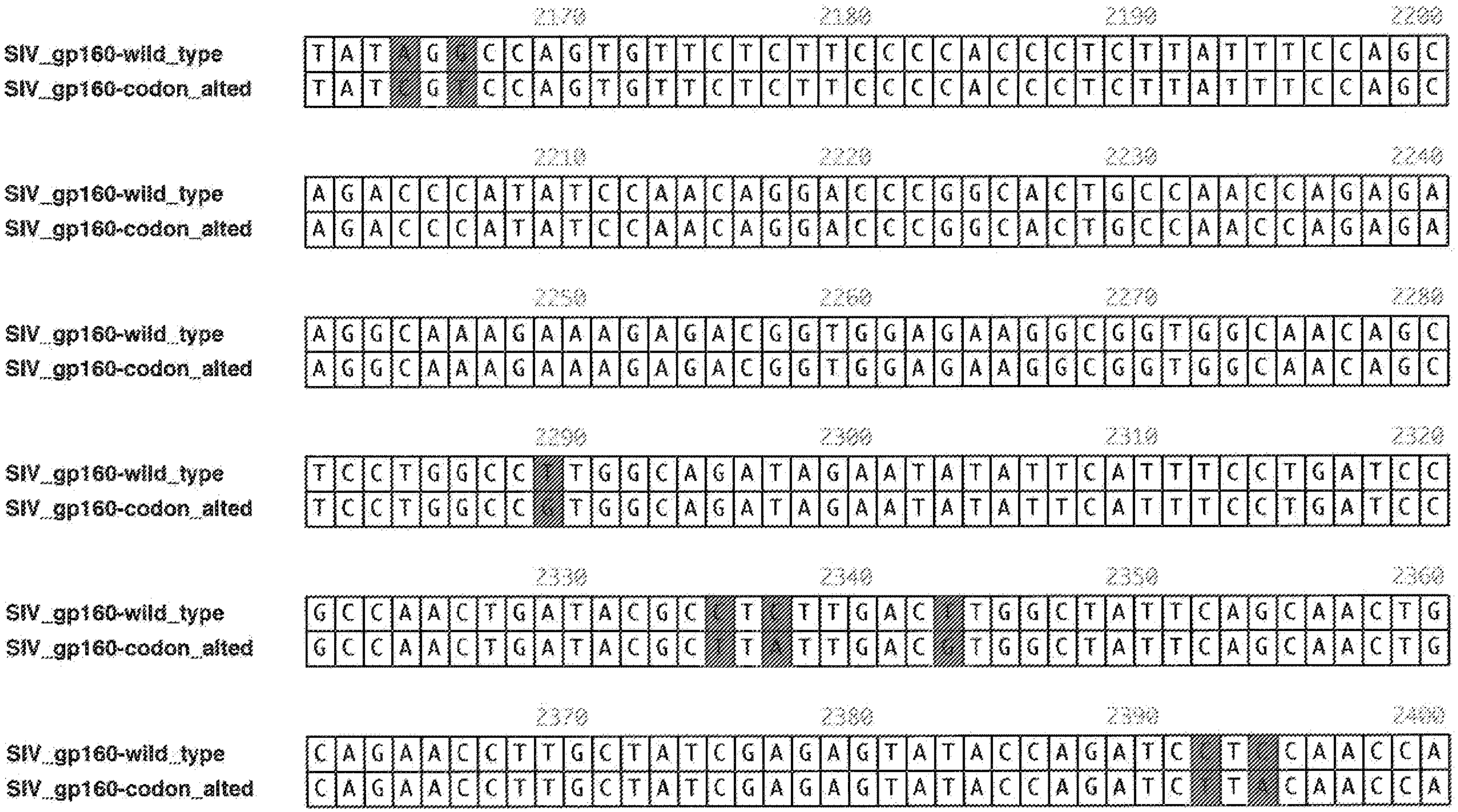
Figure 1K:
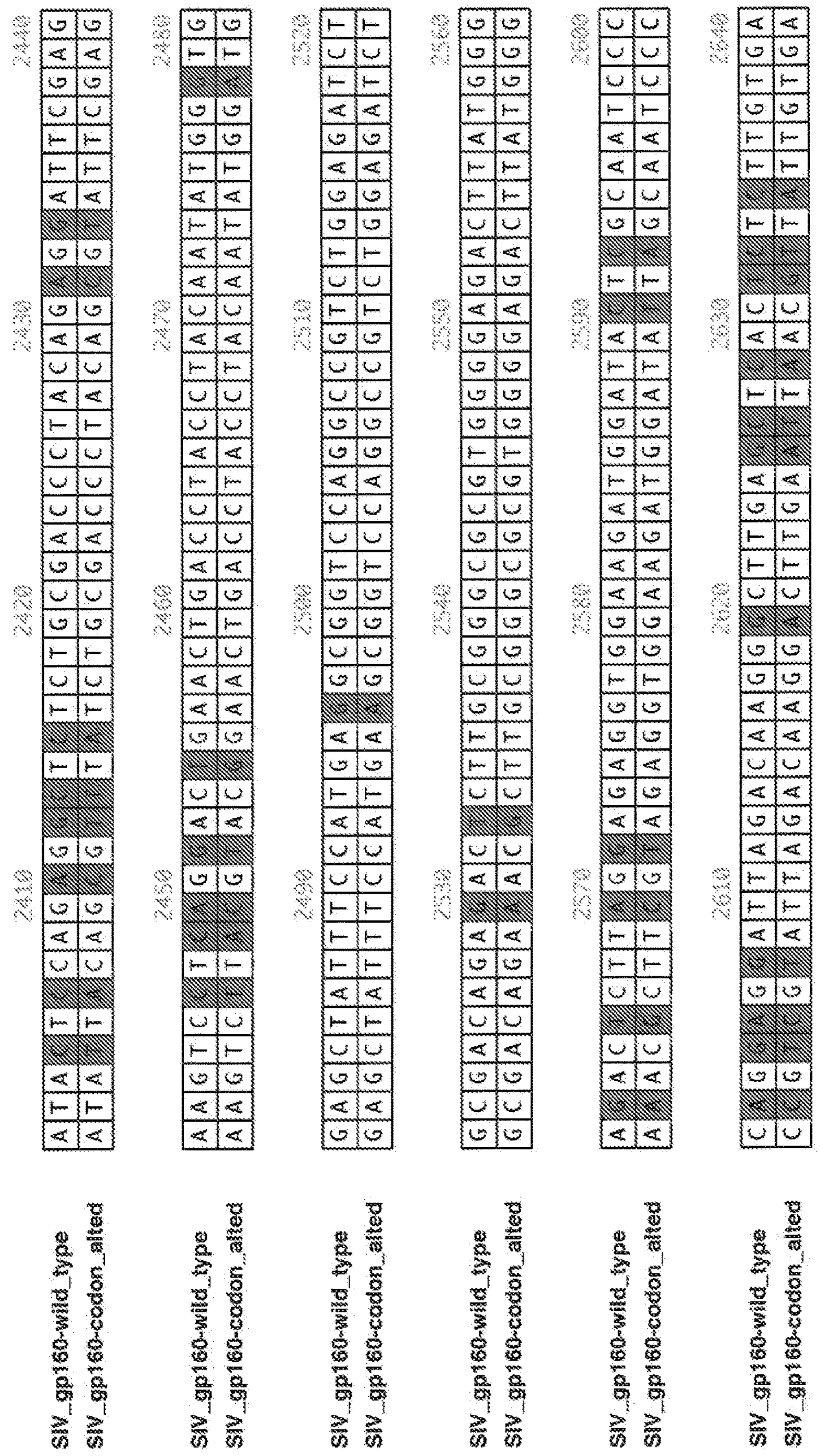
Figure 3:
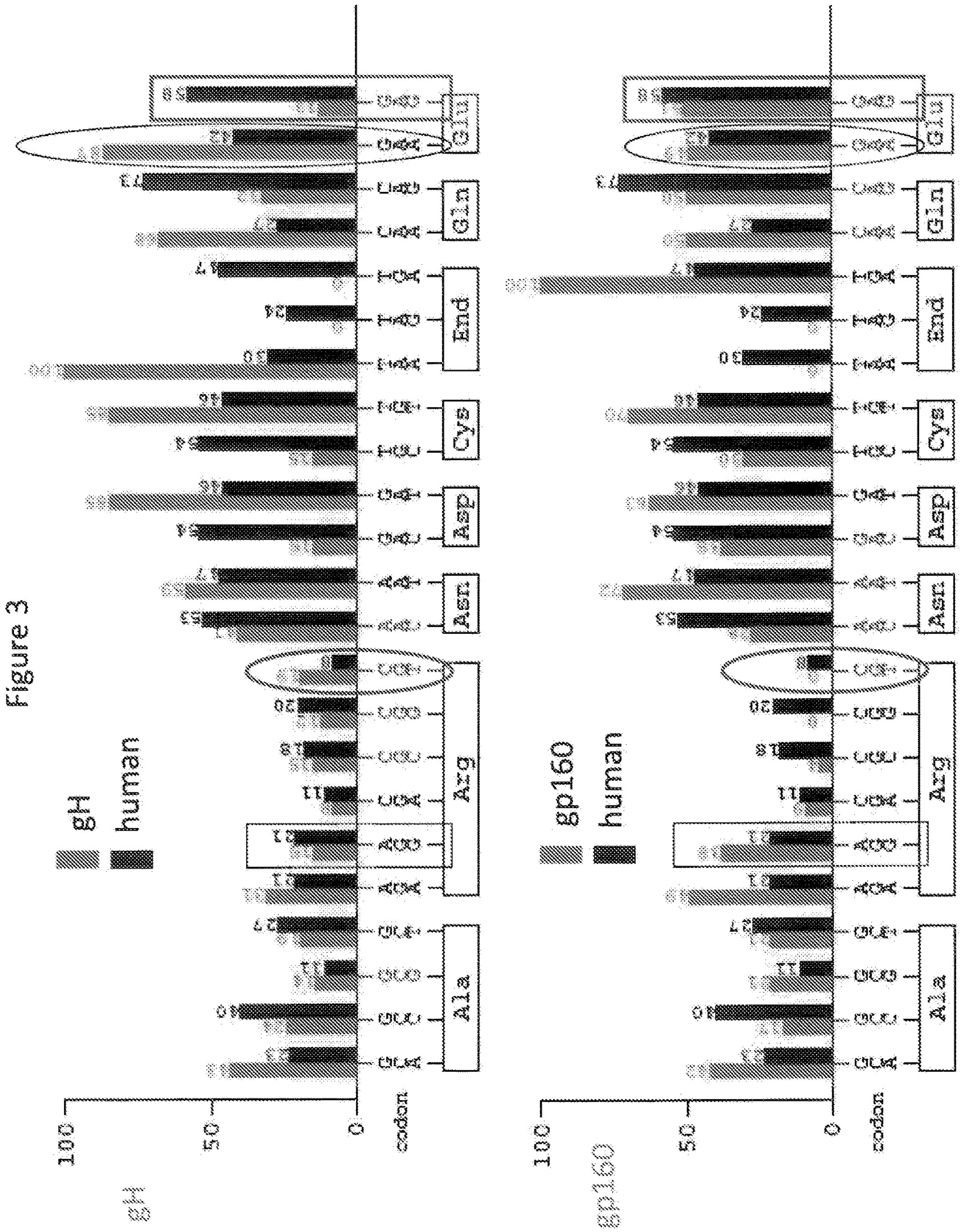
FIG. 3 provides the codon usage of the gH polypeptide of rhesus monkey rhadinovirus compared to the codon usage found in humans.
Figure 5:
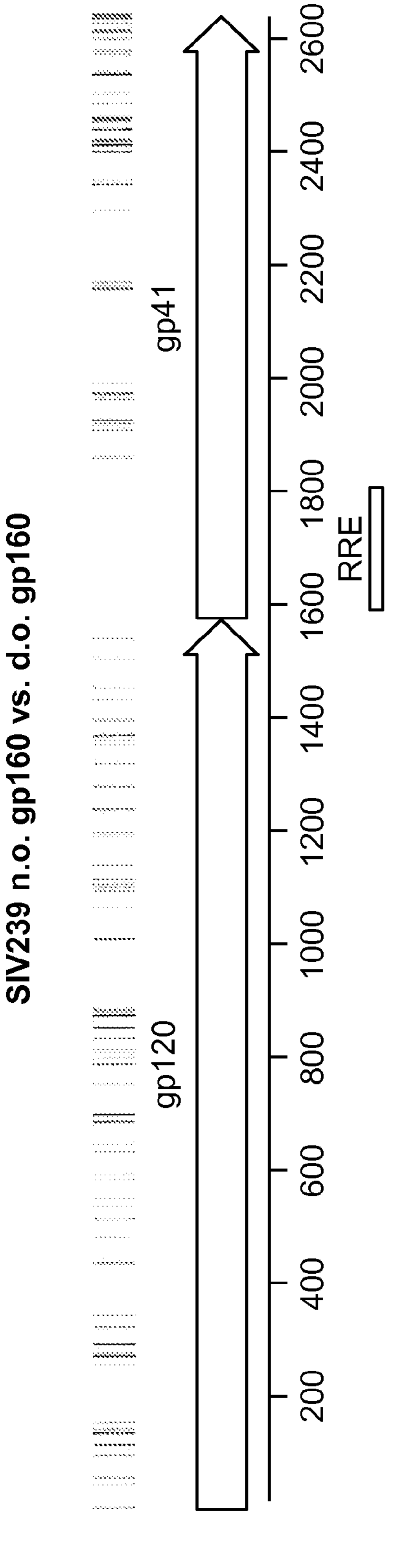
FIG. 5 provides a schematic of SIV239 n.o. gp160 vs. d.o. gp160.
Figure 6:
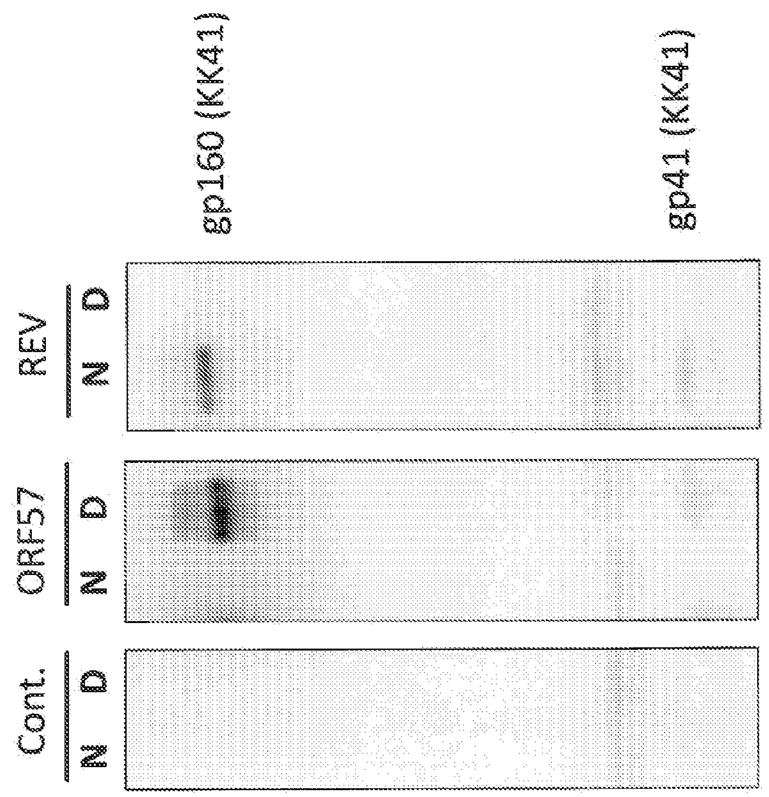
FIG. 6 shows the expression of SIVmac239-SD-gp160.
Figure 7:
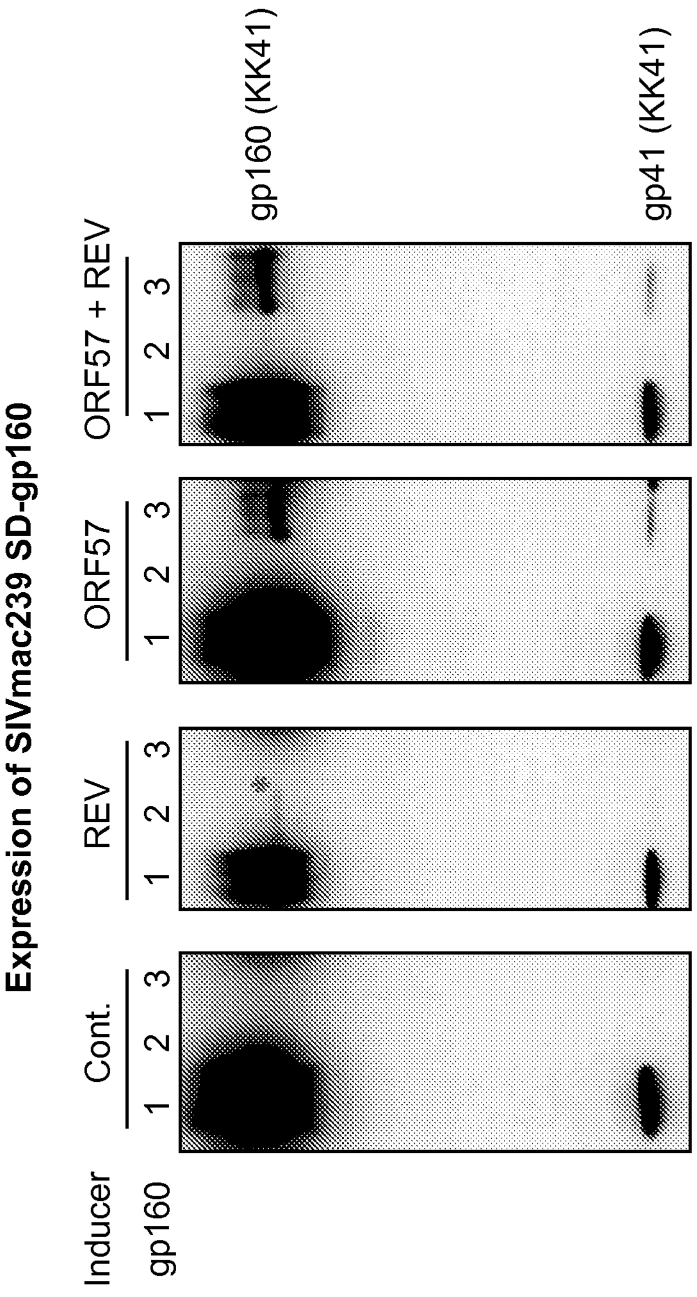
FIG. 7 shows the expression of SIVmac239 SD-gp160.
Figure 8:
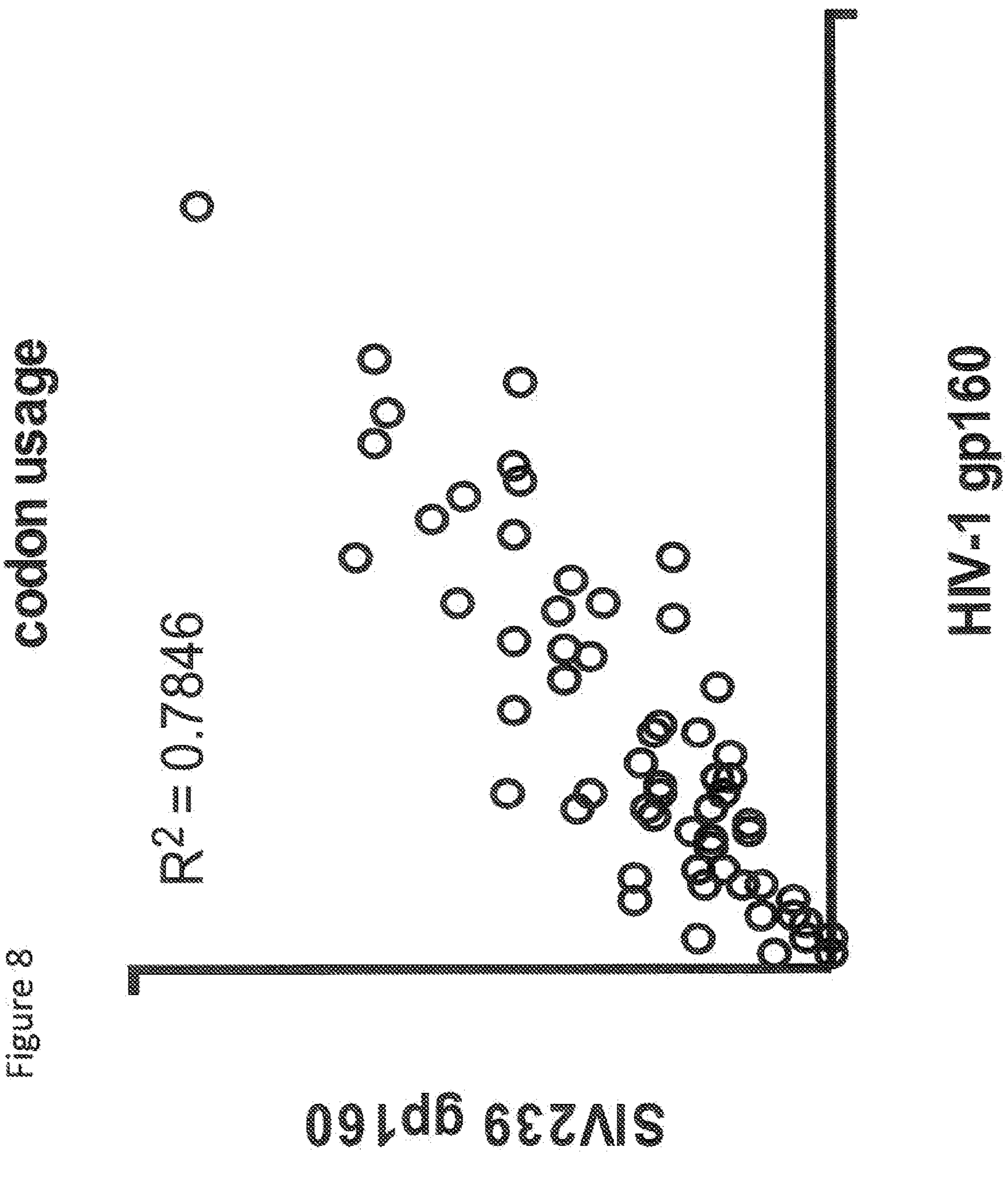
FIG. 8 shows the codon usage of SIV239gp160 verses that of HIV-1gp160.
Figure 9:
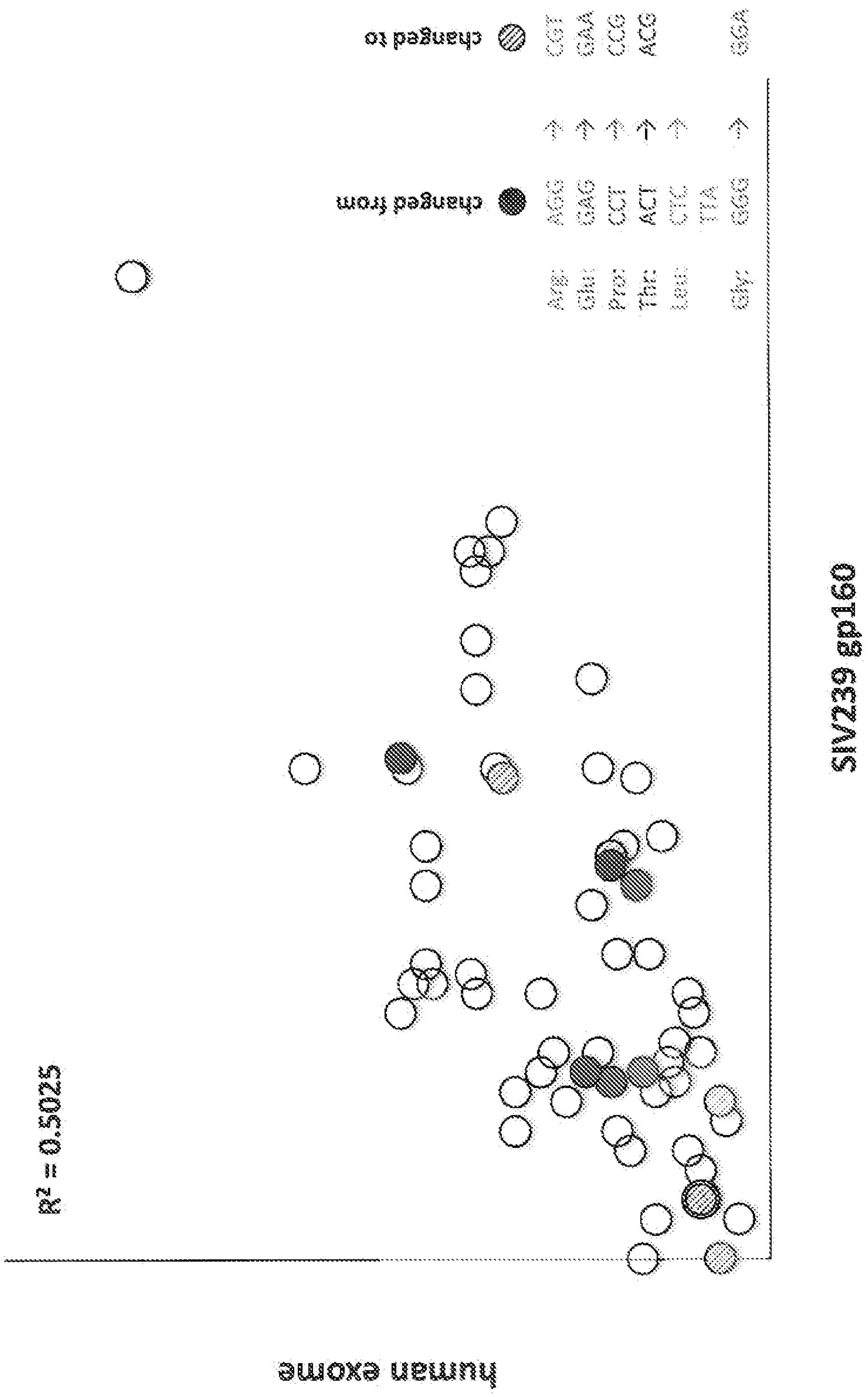
FIG. 9 shows the codon usage of the human exome verses that of SIV239 gp160.
Figure 10:
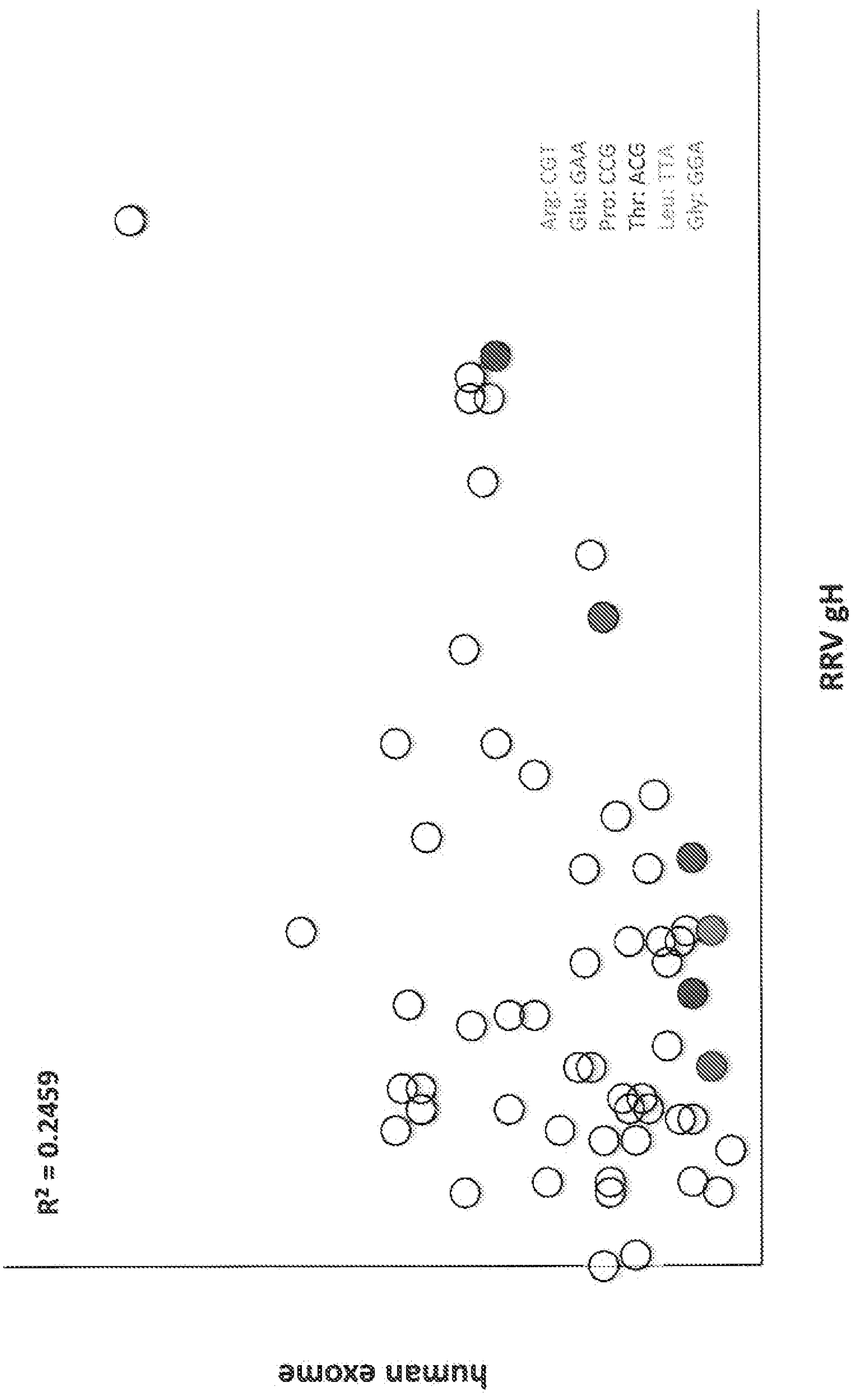
FIG. 10 shows the codon usage of the human exome verses that of RRV gH.
Figure 11:
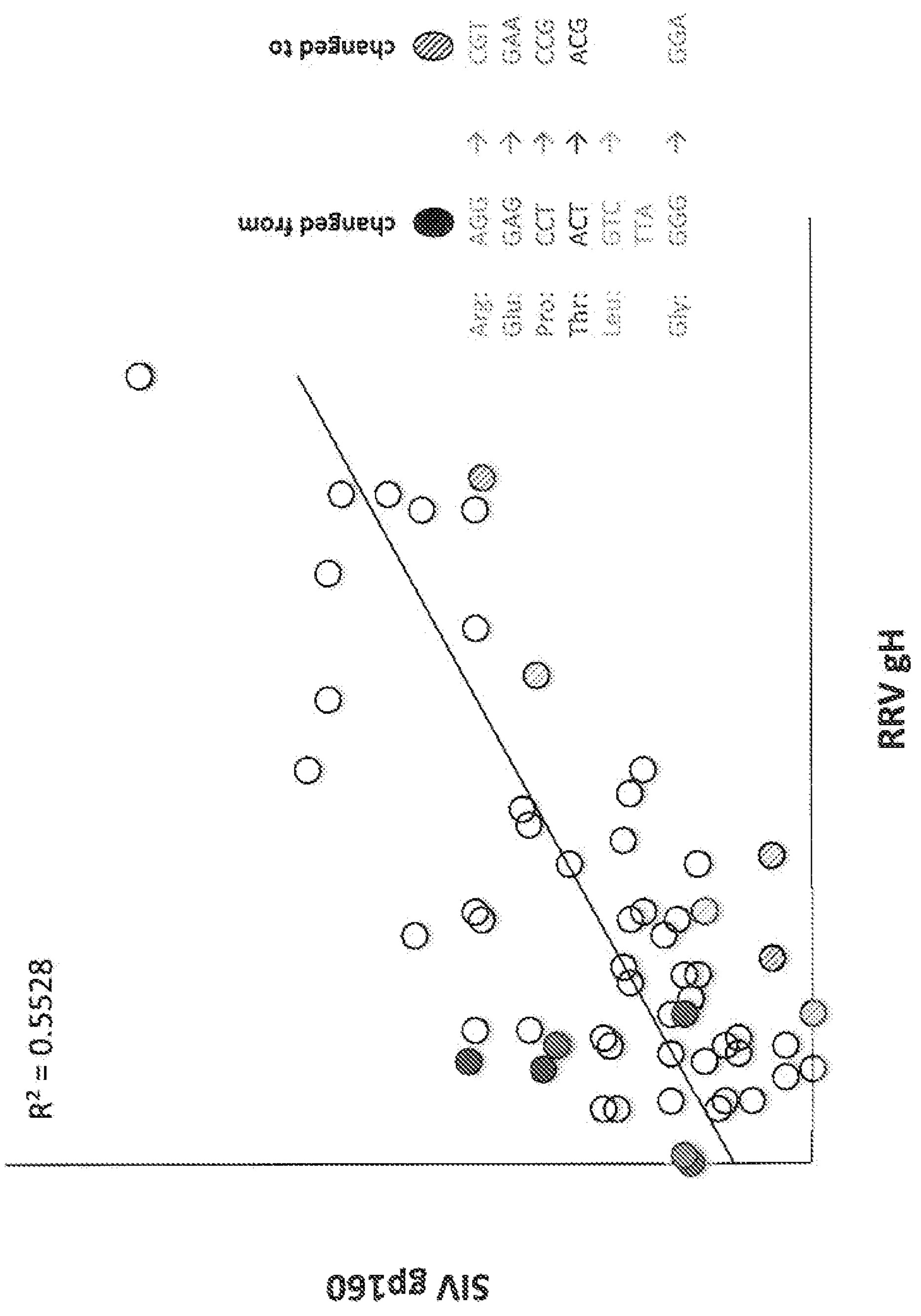
Figure 12:
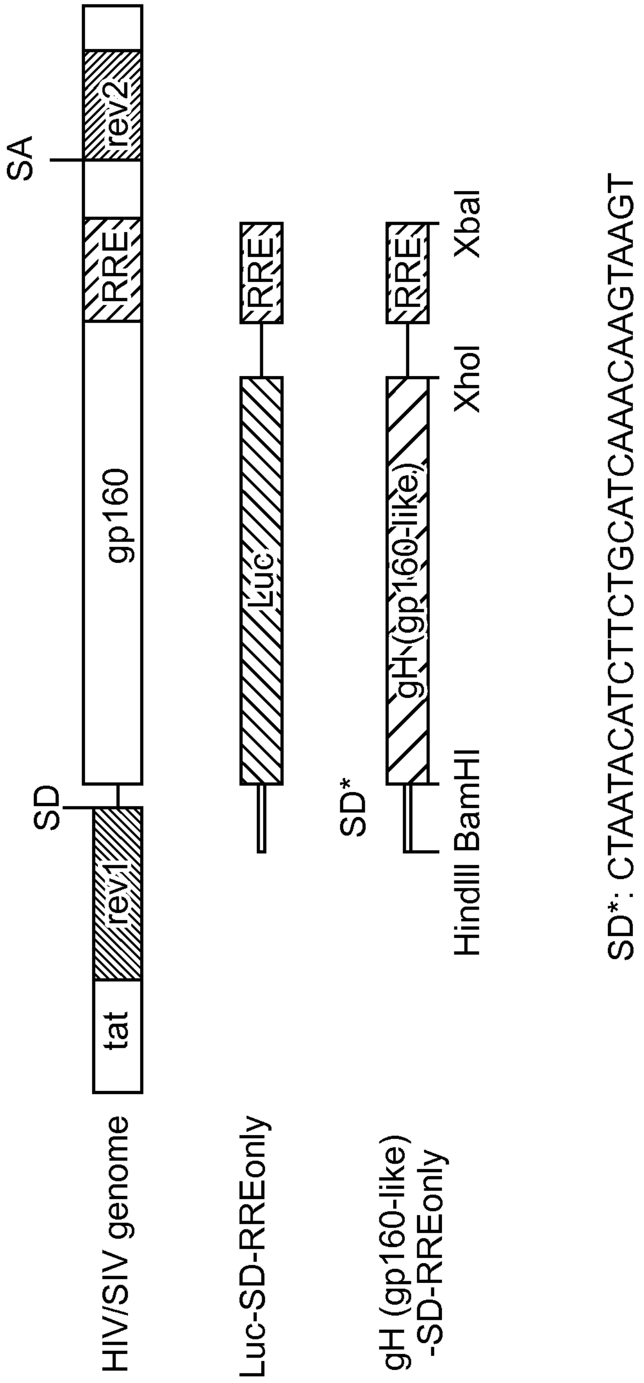
FIG. 12 provides schematics of various constructs.
Figure 14:
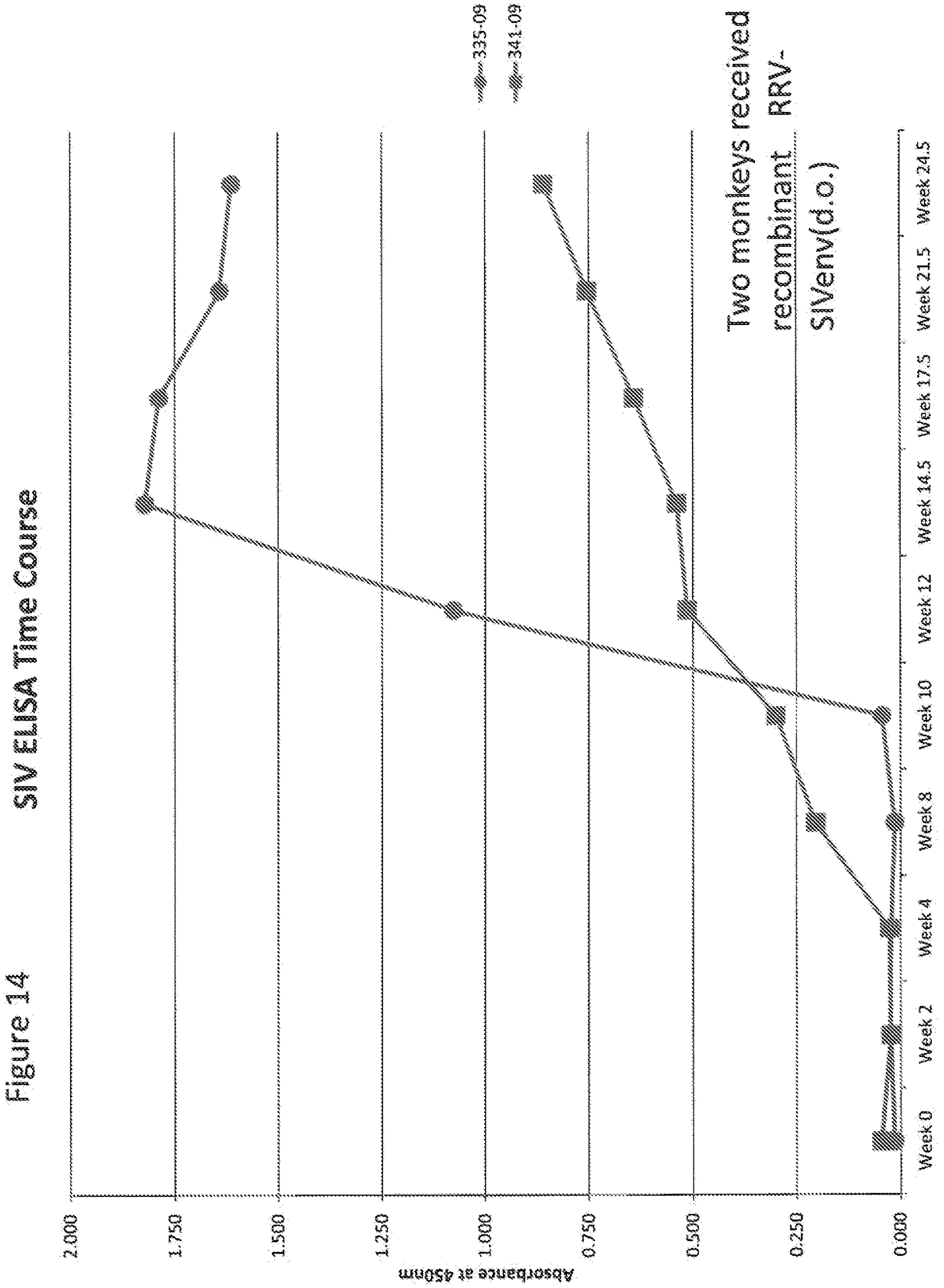
FIG. 14 provides an SIV ELISA time course from two monkeys that received recombinant RRV-SIVenv (d.o.).
Figure 15:
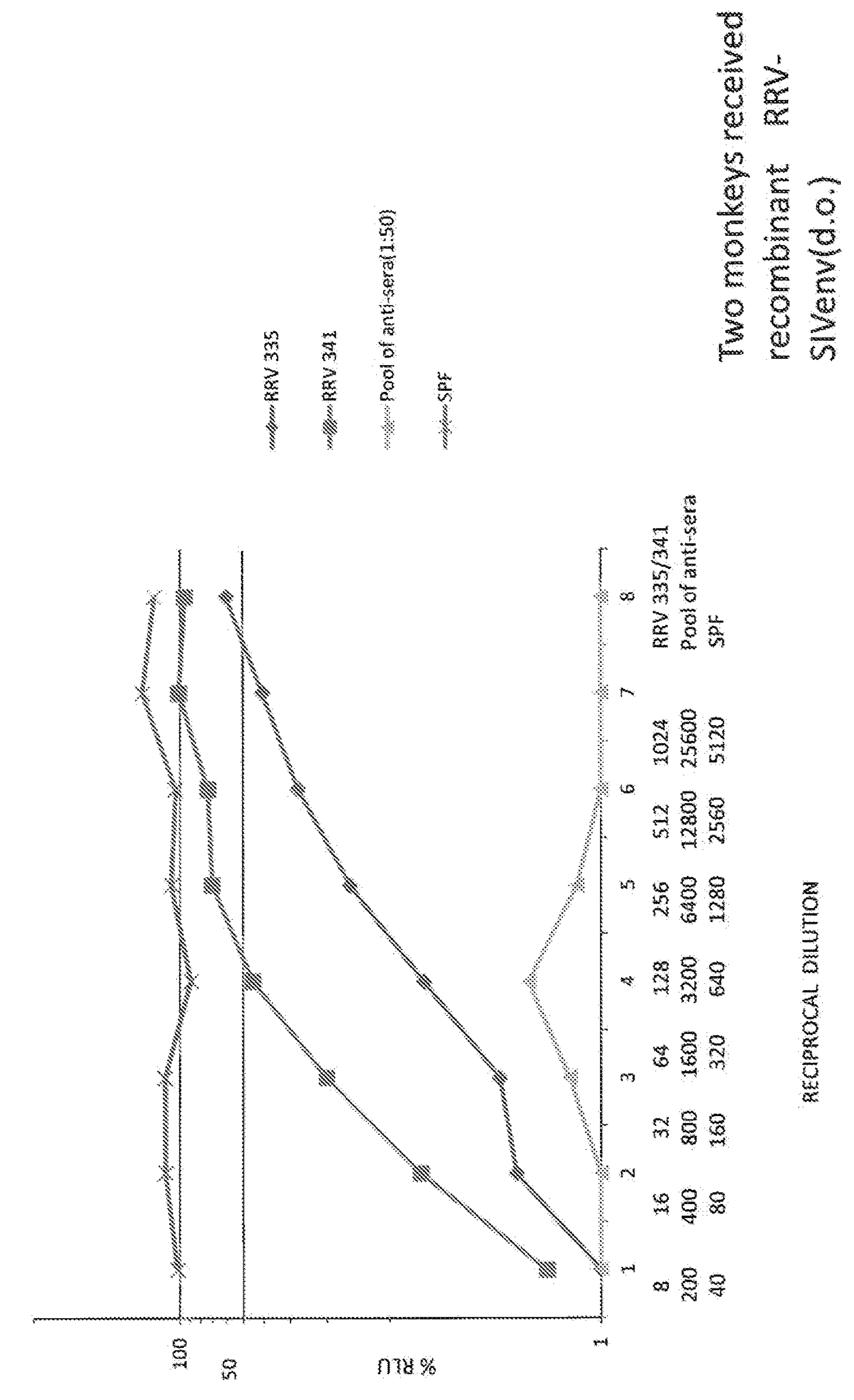
FIG. 15 provides a neutralization assay of RRV-SIV env against SIV 316.

Persisting viruses, such as the herpesviruses and the human AIDS virus HIV, temporally regulate the expression of their gene products. Structural gene products of the virus, such as the capsid protein and envelope protein, are expressed late in the lytic cycle. As demonstrated herein, when herpesviruses are used as gene expression vectors, it is useful to regulate expression of the inserted transgene as a late gene product. Specifically, temporal regulation of the expression of the transgene inserted into a herpesvirus vector can be achieved by altering the codon usage of the transgene to reflect the codon usage signature of the herpesvirus late genes. In the presence of a corresponding trans-inducer, the herpesvirus vector systems comprising a transgene of interest (e.g., a transgene encoding an antigen such as a microbial antigen or a tumor-associated antigen) having a codon usage signature of the herpesvirus late genes, find use in producing an increased immune response against the antigen encoded by the transgene of interest ("antigen of interest") when compared to other known herpesvirus vector systems which do not employ the codon usage signatures disclosed herein. Thus, in specific embodiments, various methods and compositions are provided for improving an immune response against an antigen of interest (e.g., a microbial antigen or a tumor-associated antigen).

II. Codon Usage Signature of Herpesvirus Late Genes

Methods and compositions are provided which employ a codon usage signature of at least one herpesvirus late gene. As used herein a, "herpesvirus late gene" comprises a polynucleotide encoding a herpesvirus protein required for virus assembly and egress. Such genes either show an increased expression following the replication of the viral genome, or alternatively, are expressed exclusively after and are dependent upon viral DNA replication. Representative herpesvirus late genes include structural proteins of the capsid, tegument, and envelope. In a specific embodiment, the herpesvirus late gene comprises a glycoprotein. Herpesvirus late genes that encode glycoproteins can include, for example, glycoprotein B (gB), gC, gD, gH and gL.

A codon is a series of three nucleotides that encodes a specific amino acid residue or encode for the termination of translation (stop codons). As used herein, the term "codon usage" refers to the frequency with which the various alternative codons are used to specify an amino acid in a given organism. There are 64 different codons (61 codons encoding for amino acids plus 3 stop codons) but only 20 different translated amino acids. The overabundance in the number of codons allows many amino acids to be encoded by more than one codon. Because of such redundancy, it is said that the genetic code is degenerate. Different organisms and/or different protein groups (i.e., herpesvirus late genes) and/or a given protein coding region often show particular preferences for one of the several codons that encode the same amino acid. In other words, a greater frequency of one codon will be found than expected by chance. The codon usage of any organism and/or polypeptide can be determined through a routine analysis of the polynucleotide encoding the polypeptide of interest. Thus, the codon usage of any given herpesvirus late gene or for any given group of herpesvirus late genes can be readily determined.

As used herein, a "codon usage signature" is intended a codon usage that is similar to (or in some instances identical to) the codon usage of a given target sequence (i.e., to a given herpesvirus late gene) or to a consensus codon usage derived from a group of target sequences (i.e., to a consensus codon usage derived from a group of herpesvirus late genes). A codon usage signature is "similar" to the codon usage of a given herpesvirus late gene if an engineered transgene of interest (e.g., transgene encoding a microbial antigen or tumor-associated antigen) comprising the herpesvirus late gene codon usage signature, when expressed in the corresponding herpesvirus vector, displays a temporal expression pattern of the herpesvirus late gene and/or results in an increased immune response when the herpesvirus vector particle having said transgene is introduced into a subject.

The phrase "codon usage signature" as used herein can refer to the heterologous transgene of interest and to the antigen of interest.

Methods of generating a transgene of interest having a codon usage signature for a herpesvirus late gene are provided herein in Example 1 and in FIGS. 1, 2, 4 and 13. As demonstrated herein, the design of the codon usage signature is influenced both by the codon usage of the at least one herpesvirus late gene being used and the codon usage already present in the transgene of interest. Codons to be changed in the transgene of interest can include, for example, codons in the "natural" transgene of interest that are highly utilized in the "natural" transgene of interest and/or codons in the "natural" transgene of interest that are not extensively utilized in a given herpesvirus late gene. Such codons would then be changed to codons that are highly utilized in the given herpesvirus late gene and/or changed to codons that are not extensively utilized in the natural transgene of interest sequence.

In generating a codon usage signature of a herpesvirus late gene, the total number of codons changed in the transgene of interest can be at least 1%, 2%, 3%, 4%, 5%, 6%, 7%, 8%, 9%, 10%, 11%, 12%, 13%, 14%, 15%, 20%, 25%, 30%, 35%, 40% or greater of the total number of codons in the transgene. Alternatively, the total number of codon changes in the transgene of interest can be at least 1, 5, 10, 15, 20, 25, 30, 35, 45, 55, 65, 75, 85, 95, 105, 115, 125, 135, 145 or greater.

In one non-limiting embodiment, the codons of a transgene encoding a tumor-associated antigen of interest are altered, without changing their amino acid-coding specificities, in order to reflect the codon usage of the late gene of the herpesvirus of interest.

In one non-limiting embodiment, 10.5% of the codons of SIV gp160 (93 of 880) were altered, without changing their amino acid-coding specificities, in order to reflect the codon usage of RRV gH. Six codons of relatively high prevalence in SIV gp160 were selected for change to a different codon encoding that same amino acid. The six codons selected for change were in general sparsely used (i.e., used less than 25%, less than 20%, 19%, 18%, 17%, 16%, 15%, 14%, 13%, 12%, 11%, 10%, 9%, 8%, 7%, 6%, 5%, 4%, 3%, 2%, 1% or 0%) in glycoprotein H (gH) of the rhesus monkey rhadinovirus (RRV). The new codons reflected ones of high prevalence (greater than 15%, 18%, 19%, 20%, 25%, 30%, 35%, 40%, 45%, 50%, 55%, 60%, 65%, 70%, 75%, 80%, 85%, 87% or greater) in glycoprotein H of the rhesus monkey rhadinovirus and in general relatively low prevalence (less than 45%, 40%, 35%, 30%, 25%, 20%, 15%, 10%, 5% or less) in the human exome. See FIG. 4. These changes resulted in a gp160 reading frame whose codon usage more closely resembled that of RRV gH, a gp160 reading frame that was no longer inducible by the natural trans-inducer rev but this gp160 reading frame was now trans-induced by the RRV trans-inducer orf 57. Similar methods could be used to alter trans-inducibility in other herpesviral systems, for example by changing the reading frames to reflect the abnormal codon usage in glycoproteins of other hepresviruses.

In still other non-limiting embodiments, the at least one or more codons selected for change in the transgene of interest are in general sparsely used (i.e., used less than 25%, less than 20%, 19%, 18%, 17%, 16%, 15%, 14%, 13%, 12%, 11%, 10%, 9%, 8%, 7%, 6%, 5%, 4%, 3%, 2%, 1% or 0%) in the late gene of the herpesvirus of interest. The new codons engineered into the transgene of interest reflect codons of higher prevalence (at least or greater than 15%, 18%, 19%, 20%, 25%, 30%, 35%, 40%, 45%, 50%, 55%, 60%, 65%, 70%, 75% 80% or greater) in the herpesvirus late gene of interest and in general are of relatively low prevalence (less than 45%, 40%, 35%, 30%, 25%, 20%, 15%, 10%, 5% or less) in the human exome.

Similar methods could be used to alter trans-inducibility in any herpesviral systems, for example, by changing the reading frames to reflect the abnormal codon usage in glycoproteins of any of the herpesviruses.

A non-limiting example, of a SIV gp160 coding sequence having an RRV gH codon usage signature is set forth in SEQ ID NO: 3. Variants and fragments of such a sequence are also provided. Such variants and fragments of the gp160 will retain the ability to display a temporal expression pattern of the herpesvirus late gene when expressed from an appropriate herpesvirus vector and/or result in an increased immune response when the herpesvirus vector particle having the transgene is introduced into a subject.

The term "corresponding" or "corresponds" when used to refer a herpesvirus particle or a herpesvirus vector system and a herpesvirus late gene is intended that the herpesvirus late gene was native to or derived from the given herpesvirus being used. For example, if a replication-competent herpesvirus vector or vector system is derived from herpesvirus KSHV (Kaposi's Sarcoma-Associated Herpesvirus), then a herpesvirus late gene (e.g., herpesvirus glycoprotein H (gH)) that corresponds to the replication-competent herpesvirus vector or vector system is a late gene (e.g., gH) from herpesvirus KSHV.

III. The Herpesvirus Vector Systems and Particles

Herpesviruses represent a group of double-stranded DNA viruses distributed widely within the animal kingdom. The family Herpesviridae comprises three subfamilies, namely Alphaherpesvirinae, Betaherpesvirinae and Gammaherpesvirinae. Gammaherpesviruses belong to four separate genera: Lymphocryptovirus, Rhadinovirus, Macavirus and Percavirus. Herpesvirus from the subfamily Alphaherpesvirinae include viruses from the genus Simplexvirus, such as, Bovine herpesvirus 2; Cercopithecine herpesvirus 1 (also known as Herpes B virus), Ateline herpesvirus 1, and Spider monkey herpesvirus. Herpesvirus from the genus Varicellovirus include, Bovine herpesvirus 1, Bovine herpesvirus 5, Caprine herpesvirus 1, Porcine herpesvirus 1, Equine herpesvirus 1, Equine herpesvirus 3, Equine herpesvirus 4, Canine herpesvirus 1, Feline herpesvirus 1, and Duck herpesvirus 1. Herpesvirus from the genus Mardivirus include Gallid herpesvirus 2, Gallid herpesvirus 3 (GaHV-3 or MDV-2), and Herpesvirus of turkeys (HVT). Herpesvirus from the Genus Ilovirus include, for example, Gallid herpesvirus 1. Herpesvirus from the subfamily Betaherpesvirinae include, for example, Porcine herpesvirus 2. Herpesvirus from the subfamily Gammaherpesvirinae include virus from the genus Rhadinovirus including, for example, Alcelaphine herpesvirus 1, Bovine herpesvirus 4, Equine herpesvirus 2, and Equine herpesvirus 5.

The lymphocryptoviruses (gamma-1) can include Epstein-Ban virus (EBV) or Human herpesvirus 4, Lymphocryptovirus of rhesus monkeys and Herpesvirus papio of baboons. The rhadinoviruses (gamma-2) include Herpesvirus saimiri (HVS), Kaposi's sarcoma-associated herpesvirus (KSHV) or Human herpesvirus 8, Rhesus monkey rhadinovirus (RRV), Equine herpesvirus 2 and Murid herpesvirus 68. Of particular interest within the Gammaherpesviruses are the two human viruses EBV and KSHV. Such herpesviruses have been used to generate herpesvirus vectors.

As used herein, a "herpesvirus vector" refers to a recombinant herpesvirus genome that has been modified to comprise a heterologous polynucleotide of interest. The term "herpesvirus vector" can also refer to a herpesvirus particle produced from the modified genome The herpesvirus vector is thereby designed to deliver the heterologous polynucleotide of interest to a cell. A "herpesvirus vector system" refers to the various polynucleotide components which comprise and encode the various parts of a herpesvirus vector particle. As discussed elsewhere herein, a herpesvirus vector system can be introduced into a cell and under appropriate culture conditions, a herpesvirus vector "particle" is produced. The term "herpesvirus vector particle" refers to a complete viral particle, consisting of RNA or DNA surrounded by a protein shell and constituting the infective form of a herpesvirus.

The herpesvirus vector employed herein can be replication-competent. A replication-competent herpesvirus vector particle or system comprises a modified herpesvirus genome such that the virus retains the ability to replicate. In specific embodiments, the replication-competent herpesvirus vector is an attenuated live virus (i.e., a herpesvirus which has been modified or cultivated under conditions that reduce its virulence). Various replication-competent viral vectors are known. See, for example, Argnani et al. 2005 *Gene Ther* 12: S170-S177; Meignier et al. (1990) *J Infect Dis* 162:313-321; Spector (1998) *J Infect Dis* 177:1143-1154 and Prichard et al. (2005) *Vaccine* 23:5424-5431, and US Application Publications 20020151033 and 20130251747.

A replication-competent herpesvirus encodes a trans-inducer polypeptide. As used herein, a "trans-inducer polypeptide" comprises a polypeptide that functions to enhance the expression of delayed-early and late genes of a virus. It is recognized that the trans-inducer can correspond to the replication-competent herpesvirus vector being employed. The term "corresponding" or "corresponds" when used to refer a herpesvirus particle or a herpesvirus vector system and a trans-inducer is intended that the trans-inducer was native to or derived from the given herpesvirus being used. For example, a trans-inducer comprising ORF57 from human KSHV will correspond to the herpesvirus vector system of human KSHV. Alternatively, the herpesvirus vector can be manipulated to comprise a trans-inducer from a different herpesvirus or an active variant or fragment thereof. In such instances, the trans-inducer employed will continue to allow for the production of a replication-competent viral particle and to enhance the expression of delayed-early and late genes of the herpesvirus vector system from which it is expressed.

Various methods of making the herpesvirus vector systems and viral particles disclosed herein are known. For example, BAC cloning and prokaryotic recombination technology can be employed to generate a herpesvirus vector system which comprises the transgene of interest having a codon usage signature of the herpesvirus late genes. See, for example, Gille et al. (2004) *Journal of General Biology* 4:907-917 and United States Patent Application 20120076821 each of which is herein incorporated by reference in their entirety. Such a system can be introduced into in a host cell by standard transformation procedures. Such means include, but are not limited to, electroporation, the use of liposomes, and $CaPO_4$ precipitation. See, for example, Ausabel et al. (1994) *Current Protocols in Molecular Biology*; John Wileg and Sons, Inc., and U.S. Pat. No. 5,739,081, both of which are herein incorporated by reference.

As used herein, a "host cell" comprises any cell that the herpesvirus vector system can be introduced into and/or a herpesvirus vector particle can infect. The host cell can then be cultured (in vitro or in vivo) and thereby produce a herpesvirus vector particle. Suitable host cells include, but are not limited to, prokaryotic or eukaryotic cells, e.g. bacterial cells (including gram positive cells), yeast cells, fungal cells, insect cells, and animal cells or any cell of the subject being administered the herpesvirus vector particle. Numerous mammalian cells may be used as host cells.

Methods for culturing the host cell under conditions in which the herpesvirus vector is produced and for the subsequent isolation of herpesvirus vector particles are also known in the art. For instance, the host cell comprising the herpesvirus vector system may be cultured using standard culturing techniques. Such host cells may be cultured in T-flasks, roller bottles, or bioreactors. Any acceptable culture medium may be used.

Methods of isolating herpesvirus vector particles are known in the art. As used herein, "purified herpesvirus vector particles" means a preparation of herpesvirus vector particles containing at least 50%, 60%, 70%, 80% by weight, preferably at least 85% by weight, and more preferably at least 90%, 93%, 95%, 98%, 99% by weight, of the herpesvirus vector particles.

IV. Transgenes of Interest

Methods are provided to express a transgene of interest in a target cell. In a typical embodiment, a transgene of interest encodes an antigen of interest, such as, for example, a microbial antigen or a tumor-associated antigen. As used herein, a "transgene" refers to a polynucleotide which one desires to be expressed. The target cell can be from any animal, and in specific embodiments the animal is a vertebrate, and more particularly the vertebrate is a mammal. In specific embodiments, the vertebrate is a human. In still other embodiments, the target cell is from an avian. In other embodiments the vertebrate is a non-human vertebrate. Such non-human vertebrates include, but are not limited to, rodents, non-human primates, ovines, bovines, ruminants, lagomorphs, porcines, caprines, equines, murines, canines, felines, ayes, etc. By "subject" is intended a vertebrate, typically a mammal (e.g., primates, humans, agricultural and domesticated animals such as, but not limited to, dogs, cats, cattle, horses, pigs, sheep, and the like) or an avian. In one embodiment, the subject undergoing treatment with the pharmaceutical formulations disclosed herein is a human.

As used herein, a "tumor-associated antigen" comprises any antigen produced by a tumor cell. A "tumor-associated antigen" can be an antigen present only in a tumor cell and not on any other cell, or it may be an antigen present in some tumor cells and also in some normal cells. Tumor-associated antigens can include, for example, products of mutated oncogenes and tumor suppressor genes, overexpressed or aberrantly expressed cellular proteins, tumor antigens produced by oncogenic viruses, oncofetal antigens, altered cell surface glycolipids and glycoproteins or cell-type specific differentiation antigens.

In one, non-limiting embodiment, the tumor-associated antigen comprises BAGE, GAGE, MAGE, NY-ESO-1, SSX, gp100, Melan-A/Mart-1, Tyrosinase, PSA, CEA, Mammaglobin-A, p53, HER-2/neu, livin, survivin, ß-catenin-m, ß-Actin/4/m, Myosin/m, HSP70-2/m, HLA-A2-R17OJ, GM2, GD2, GD3, MUC-1, sTn, globo-H, WT1, PR1, E75, ras, alpha fetoprotein (AFP), URLC10, VEGFR1 and 2, mutant p53, NY-ESO-1, HPV16 E7, ß-catenin, CDK4, CDC27, α actinin-4, TRP1/gp75, TRP2, gangliosides, PSMA, HER2, WT1, EphA3, EGFR, CD20, telomerase, MART-1 or any antigenic portion thereof.

The transgene of interest used in the compositions and methods provided herein can comprise any polynucleotide of interest and can be from any organism including, but not limited to, rodents, non-human primates, ovines, bovines, ruminants, lagomorphs, porcines, caprines, equines, murines, canines, felines, ayes, humans, and/or microbes. As used herein, a microbe includes any bacterial, viral, parasites, protozoan, mycoplasma, fungus, yeast or prior. Additionally, the transgene of interest may be a variant of a naturally occurring sequence or even a synthetic sequence.

A transgene of interest used in the methods and compositions disclosed herein comprises a nucleotide sequence encoding a polypeptide. Such a sequence may be native to the target cell of the herpesvirus vector (i.e., naturally expressed in the target cell) or native to the backbone of the herpesvirus vector being employed or the nucleotide sequence may be heterologous or foreign to the target cell or to the herpesvirus vector being employed. As used herein, "heterologous" in reference to a sequence is a sequence that originates from a foreign species, or, if from the same species, is substantially modified from its native form in composition and/or genomic locus by deliberate human intervention.

While it is recognized that a variety of transgenes of interest may be used in the methods and compositions disclosed herein, in one embodiment, the transgene of interest comprises an antigen. As used herein the term "antigen" or "antigenic portion thereof" refers to a substance which when introduced into the body stimulates the production of antibodies (antigenicity). In specific embodiments, that antigen may further be immunogenic. The term "immunogenic" refers to the ability of a substance to induce an immune response when administered to an animal. Immunogenicity or antigenicity can be assayed for by a variety of methods including, for example, by detecting binding to antibody, various immunoassays known in the art, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), Western blots, immunoprecipitation reactions, agglutination assays (e.g., gel agglutination assays, hemagglutination assays), complement fixation assays, immunofluorescence assays, protein A assays, and immunoelectrophoresis assays, etc. Many means are known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Various antigens (e.g., tumor-associated antigens, microbial antigens) or antigenic portions thereof can be selected for use as antigens of interest from among those antigens known in the art or determined by immunoassay to be able to bind to antibody or MHC molecules (antigenicity) or generate an immune response (immunogenicity) as described above. Additional, useful antigens or derivatives thereof can also be identified by various criteria, such as the antigen's involvement in cancer (where it is desired to treat or prevent cancer) or in neutralization of a pathogen's infectivity (wherein it is desired to treat or prevent infection by such a pathogen) (Norrby (1985) *Vaccines* 85, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope can display a small or no degree of antigenic variation in time or amongst different isolates of the same pathogen.

While any antigen of interest can be employed in the methods and compositions provided herein, non-limiting examples include tumor-associated antigens or antigenic portions thereof that are associated with, derived from, or predicted to be associated with a cancer. In such instances the tumor-associated antigen of interest can be from any cancer cell, including, but not limited to, melanoma, lymphoma, leukemia, lung cancer, bladder cancer, colon cancer, breast cancer, prostate cancer, esophageal cancer, liver cancer, pancreatic cancer, ovarian cancer, non-small cell lung cancer, renal cancer, neuroblastoma, colorectal cancer, uterine cancer, acute myelocytic leukemia, sarcomas, brain cancer, bone cancer, basal cell carcinoma, cervical cancer, colorectal cancer, endometrial cancer, Ewing sarcoma, retinoblastoma, gastric cancer, gastrointestinal cancer, testicular cancer, glioma, head and neck cancer, hepatocellular cancer, kidney cancer, oral cancer, melanoma, multiple myeloma, nasopharyngeal cancer, thyroid cancer, rectal cancer, skin cancer, squamous cell carcinoma, throat cancer, AIDS related cancers such as Kaposi sarcoma and lymphoma, or any antigenic portion thereof.

Additional non-limiting examples of an antigen of interest include antigens or antigenic portions thereof that are associated with, derived from, or predicted to be associated with an infectious disease. In such instances the antigen of interest can be from a microbe including from a bacterium, virus, protozoan, mycoplasma, fungus, yeast, parasite, or prion. For example, but not by way of limitation, the antigen may be from a human immunodeficiency virus (HIV) 1 or 2 (see below), a herpes virus such as herpes simplex or herpes zoster, other retroviruses, such Human T-cell Lymphotropic Virus, a hepatitis virus, an influenza virus, a rhinovirus, respiratory syncytial virus, cytomegalovirus, adenovirus, Mycoplasma pneumoniae, polio viruses, hepatitis A virus, human coxsackie viruses, echoviruses, equine encephalitis viruses, rubella viruses, dengue viruses, encephalitis viruses, yellow fever viruses, coronaviruses, vesicular stomatitis viruses, rabies viruses, Ebola viruses, parainfluenza viruses, mumps virus, measles virus, Hantaan viruses, bunga viruses, hemorrhagic fever viruses, reoviruses, orbiviruses, rotaviruses, Hepatitis B virus, parvoviruses, papilloma viruses, polyoma viruses, adenoviruses), herpes simplex virus (HSV) 1 and 2, varicella zoster virus, cytomegalovirus (CMV), variola viruses, vaccinia viruses, pox viruses, African swine fever virus, the unclassified agent of delta hepatitis, the agents of non-A, non-B hepatitis; a bacterium of the genus *Salmonella, Staphylococcus, Streptococcus, Enterococcus, Clostridium, Escherichia, Klebsiella, Vibrio, Mycobacterium*, amoeba, a malarial parasite, *Trypanosoma cruzi, Helicobacter pylori, Borrelia burgdorferi, Legionella pneumophila, Mycobacterium tuberculosis, Mycobacterium bovis* (BCG), *Mycobacterium avium, Mycobacterium intracellulare, Staphylococcus aureus, Neisseria gonorrhoeae, Neisseria meningitidis, Listeria monocytogenes, Streptococcus pyogenes, Streptococcus pneumoniae, Haemophilus influenzae, Moraxella catharralis, Klebsiella pneumoniae, Bacillus anthracia, Corynebacterium diphtheriae, Clostridium perfringens, Clostridium tetani, Enterobacter aerogenes, Klebsiella pneumoniae, Pasteurella multocida*, and *Treponema pallidum*; infectious fungi like: *Cryptococcus neoformans, Histoplasma capsulatum, Coccidioides immitis, Blastomyces dermatitidis, Candida albicans*; and infectious protists like, for example: *Plasmodium falciparum, Trypanosoma cruzi, Leishmania donovani* and *Toxoplasma gondii*; as well as infectious fungi such as those causing e.g., histoplasmosis, candidiasis, cryptococcosis, blastomycosis and cocidiodomycosis; as well as *Candida* spp. (i.e., *C. albicans, C parapsilosis, C. krusei, C. glabrata, C. tropicalis*, or *C. lusitaniaw*); *Torulopus* spp. (i.e., *T. glabrata*); *Aspergillus* spp. (i.e., *A. fumigalus*), *Histoplasma* spp. (i.e., *H. capsulatum*); *Cryptococcus* spp. (i.e., *C. neoformans*); *Blastomyces* spp. (i.e., *B. dermatilidis*); *Fusarium* spp.; *Trichophyton* spp., *Pseudallescheria boydii, Coccidioides immits*, and *Sporothrix schenckii*, etc or any antigenic portion thereof.

In specific embodiments, the antigen of interest is viral antigen including, for example, an antigen from Retrovirdae, Flaviviridae, dengue virus, lentivirus, HIV virus or SIV virus.

In other embodiments, the antigen of interest is a bacterial antigen including, for example, an antigen from *Mycobacterium tuberculosis.*

In other embodiments, the antigen of interest is a parasitic antigen including, for example, an antigen from *plasmodium.*

The transgene of interest having the codon usage signature of the herpesvirus late gene can be operably linked to any promoter that drives expression of the sequence at a sufficient level to produce the desired level of the gene product. A nucleotide sequence is "operably linked" to an expression control sequence (e.g., a promoter) when the expression control sequence controls and regulates the transcription and translation of that sequence. The term "operably linked" when referring to a nucleotide sequence includes having an appropriate start signal (e.g., ATG) in front of the nucleotide sequence to be expressed and maintaining the correct reading frame to permit expression of the sequence under the control of the expression control sequence and production of the desired product encoded by the sequence. If a gene that one desires to insert into a recombinant nucleic acid molecule does not contain an appropriate start signal, such a start signal can be inserted in front of the gene.

In specific embodiments and as used herein, the DNA construct containing the transgene of interest will include in the 5'-3' direction of transcription, a transcriptional and translational initiation region, a nucleotide sequence of interest, and a transcriptional and translational termination region functional in the targeted host cell. The transcriptional initiation region, the promoter, may be native or foreign to the target cell. Additionally, the promoter may be the natural sequence or, alternatively, a synthetic sequence. By "foreign" is intended that the transcriptional initiation region is not found in the target cell into which the herpesvirus vector is introduced. While expression of the sequence using heterologous promoters can be done, the native promoter sequence may also be used. The termination region may be native with the transcriptional initiation region, may be native with the operably linked transgene of interest, or may be derived from another source.

In selecting an expression control sequence, a variety of factors will normally be considered. These include, for example, the relative strength of the system, its controllability, and its compatibility with the particular nucleotide sequence or gene to be expressed.

Any promoter may be operably linked to the transgene of interest so long as the promoter is active in the target cell. Non-limiting examples of promoters that can be employed to express the transgene of interest include, but are not limited to, constitutive promoter, tissue-preferred (e.g., tissue-specific) promoter, or temporally regulated promoters.

One example of a useful promoter is the immediate early cytomegalovirus promoter (CMV-IE) of human or murine origin, or it may optionally have another origin such as from rat or guinea pig. See, for example, EP 260 148, EP 323 597, U.S. Pat. Nos. 5,168,062, 5,385,839, and 4,968,615, as well as to WO 87/03905. In more general terms, the promoter may have either a viral or a cellular origin. A strong viral promoter other than CMV-IE that may be employed is the early/late promoter of the SV40 virus or the LTR promoter of the Rous sarcoma virus, the promoter of a gene of the cytoskeleton, such as the desmin promoter (Kwissa M. et al.), or the actin promoter (Miyazaki J. et al.). Functional fragments or variants of these promoters, i.e., portions of these promoters that maintain adequate promoter activity can further be employed, e.g. truncated CMV-IE promoters according to WO 98/00166 or U.S. Pat. No. 6,156,567 and may be used. In specific embodiments, the promoter is a strong promoter that is functional in eukaryotic cells.

In preparing the expression cassette, the various polynucleotides may be manipulated, so as to provide for the polynucleotide sequences in the proper orientation and, as appropriate, in the proper reading frame. Toward this end, adapters or linkers may be employed to join the polynucleotides or other manipulations may be involved to provide for convenient restriction sites, removal of superfluous DNA, removal of restriction sites, or the like. For example, linkers such as two glycines may be added between polypeptides. Methionine residues encoded by atg nucleotide sequences may be added to allow initiation of gene transcription. For this purpose, in vitro mutagenesis, primer repair, restriction, annealing, resubstitutions, e.g., transitions and transversions, may be involved.

Conventional molecular biology, microbiology, and recombinant DNA techniques within the skill of the art may be employed herein. Such techniques are explained fully in the literature. See, e.g., Sambrook et al., "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues.

An "isolated" polynucleotide is substantially or essentially free from components that normally accompany or interact with the polynucleotide as found in its naturally occurring environment. Thus, an isolated polynucleotide is substantially free of other cellular material or culture medium when produced by recombinant techniques, or substantially free of chemical precursors or other chemicals when chemically synthesized.

A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

It is further recognized that the DNA construct may contain various sequences that facilitate the expression, stabilization, and/or localization of the nucleotide sequence of interest and/or the resulting gene product. Such sequences include enhancers, introns, and post-transcriptional elements. In yet other embodiments the DNA construct further includes affinity tags for purification or labeling (e.g., with antibodies).

At least one DNA construct may further comprise a selectable marker operably linked to a promoter. Selectable markers include, but are not limited to, luciferase, β-gal, GFP, and various antibiotic resistance sequences. One of skill will appreciate that numerous possibilities exist.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments. For this purpose, in vitro mutagenesis, primer repair, restriction, annealing, resubstitutions, e.g., transitions and transversions, may be involved.

V. Pharmaceutical Compositions

The herpesvirus particles disclosed herein can be incorporated into pharmaceutical compositions suitable for administration. Such compositions typically comprise the herpesvirus particle and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. In addition, it may be desirable to administer a therapeutically effective amount of the pharmaceutical composition locally to an area in need of treatment. This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In one embodiment, administration can be by direct injection at the site (or former site) of a cancer that is to be treated. In another embodiment, the therapeutically effective amount of the pharmaceutical composition is delivered in a vesicle, such as liposomes (see, e.g., Langer, *Science* 249:1527-33, 1990 and Treat et al., in *Liposomes in the Therapy of Infectious Disease and Cancer*, Lopez Berestein and Fidler (eds.), Liss, N.Y., pp. 353-65, 1989).

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL® (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens, liposomes targeted to cancer cells with monoclonal antibodies to tumor-associated antigens, etc.) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

VI. Methods of Use

The methods provided herein comprise contacting a target cell with an effective amount of a replication-competent herpesvirus vector particle comprising a transgene of interest which has been modified to comprise a codon usage signature of a herpesvirus late gene operably linked to an active promoter. Such methods find use in delivering to the target cell the transgene of interest and modulating (i.e. increasing or decreasing) the level of the transgene of interest or the encoded polypeptide in the target cell. As used herein, the term "modulating" includes "inducing", "inhibiting", "potentiating", "elevating", "increasing", "decreasing" or the like. Each of these terms denote a quantitative difference between two states and in particular, refer to at least a statistically significant difference between the two states. A decrease or an increase in level and/or activity of a polypeptide or polynucleotide comprises any statistically significant increase or decrease including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the desired activity compared to an appropriate control. One example of a control is a recombinant transgene that lacks the codon usage signature.

Various methods of administering a herpesvirus vector particle to a cell in order to allow for the modulation in the level of the transgene of interest or the product encoded thereby are well known in the art. Any means of administering (i.e., contacting) the cell with the viral particle that permits the viral particle to infect the target cell may be used. In such embodiments, the effective dose administered to the target cells will be sufficient to allow for the production of the desired modulation of the level/activity of the transgene and/or the protein it encodes.

In further embodiments, the delivery and expression of the transgene of interest in a cell of a subject finds use in the improvement of a clinical outcome of the subject. For example, delivery of a therapeutically effective amount of a herpesvirus vector particle to a target cell of a subject may be accomplished via administration of a pharmaceutical composition comprising a therapeutically effective dose of the herpesvirus vector particle. By "therapeutically effective amount" or "dose" is meant the concentration of viral vector particle that is sufficient to elicit the desired therapeutic effect. For example, a therapeutically effective dose will be sufficient to reduce or lessen the clinical symptoms of the disorder (e.g., cancer, infection) being treated or prevented via the expression of the transgene of interest. Thus, an effective amount of the herpesvirus vector particle disclosed herein brings about a positive therapeutic response with respect to treatment or prevention of the disorder (e.g., cancer, infection). "Positive therapeutic response" refers to, for example, an increased immune response and/or improving the condition of at least one of the symptoms of disorder being treated. A positive therapeutic response in regard to treating a cancer includes curing or ameliorating the symptoms of the disease. In the present context, a deficit in the response of the subject can be evidenced by continuing or spreading of the cancer. An improvement in a clinically significant condition in the subject includes a decrease in the size of a tumor, increased necrosis of a tumor, clearance of the tumor from the host tissue, reduction or amelioration of metastasis, or a reduction in any symptom associated with the cancer.

a. Methods of Increasing an Immune Response

Further provided are methods of inducing an immune response against an antigen of interest in a subject. The methods comprise administering to the subject an effective amount of a pharmaceutical composition comprising a replication-competent herpesvirus vector particle comprising a polynucleotide comprising a heterologous transgene of interest encoding an antigen of interest, wherein the transgene of interest has been modified to comprise a codon usage signature of a herpesvirus late gene operably linked to an active promoter. The effective amount of the herpesvirus vector is sufficient to provide an immune response against the antigen of interest.

In specific embodiments, administration of a therapeutically effective amount of the herpesvirus vector particle having a heterologous transgene of interest encoding an antigen of interest and having been modified to comprises a codon usage signature of a herpesvirus late gene results in an increased immune response against an antigen of interest, when compared to the immune response produced by a herpesvirus vector particle comprising the heterologous transgene of interest encoding the antigen of interest, wherein the transgene of interest is not encoded by a polynucleotide comprising the codon usage signature of a herpesvirus late gene.

By "increased" or "enhanced" immune response is intended a statistically measurable induction or increase in an immune response over the control sample. In specific embodiments, the increased immune response comprises an increase in serum immunoglobulin levels against the antigen of interest. As used herein, an "increase in serum immunoglobulin levels" comprises any statistically significant increase in the level of serum antibody titers of any one or all of the immunoglobulin classes (i.e. IgE, IgG, IgM, IgD and/or IgA) in a subject. Such an increase can comprise an increase in serum IgE, IgM, IgD, or IgA antibody titers of at least 10%, 20%, 30%, 40%, 50%, 60%, 70%, 80%, 90%, 95% or greater in the serum of a subject following the administration of the herpesvirus vector particle comprising a heterologous transgene of interest encoding an antigen of interest having been modified to comprise a codon usage signature of a herpesvirus late gene.

An increased immune response can also refer to not only a greater response in terms of the production of more antibody or T cells but also the production of more protective antibody or T cells. Thus, in specific embodiments, an increase in an immune response refers to any statistically significant increase in the level of antibodies or T cells or antibody or T cell production or any statistically significant increase in a protective antibody response. Such an increase can include a 5%, 10%, 20%, 30%, 40%, 50%, 60%, 70%, 80%, 90%, 100% or higher increase in the level of antibodies or in the protective antibody response. The immunogenicity of a polypeptide can be assayed for by measuring the level of antibodies or T cells produced against the polypeptide. Assays to measure for the level of antibodies are known, for example, see Harlow and Lane (1988) *Antibodies, A Laboratory Manual* (Cold Spring Harbor Publications, New York), for a standard description of antibody generation, immunoassay formats and conditions that can be used to determine specific immunoreactivity. In other instances, increased immunogenicity can be detected as an improved clinical outcome, as discussed elsewhere herein.

In specific embodiments, the increased immune response against the antigen of interest having the codon usage signature of a herpesvirus late gene is increased when compared to the immune response generated against the antigen of interest when this codon usage signature is not used.

Such methods find use in, for example, increasing the immune response against the antigen of interest. As such, the various methods and compositions provided herein can be used to treat or prevent a variety of diseases including cancer and infectious diseases caused by various microbes including, for example, bacterium, virus, protozoan, mycoplasma, fungus, yeast, parasite, or prion.

"Treatment" is herein defined as curing, healing, alleviating, relieving, altering, remedying, ameliorating, improving, or affecting the condition or the symptoms of a subject. The subject to be treated can be suffering from or at risk of developing a cancer or various infectious diseases caused by various microbes including, for example, bacterium, virus, protozoan, mycoplasma, fungus, yeast, parasite, or prion. Administration of a replication-competent herpesvirus vector system comprising a polynucleotide comprising a heterologous transgene of interest encoding an antigen of interest, wherein the antigen of interest has been modified to comprise a codon usage signature of a herpesvirus late gene operably linked to an active promoter, can be for either a prophylactic or therapeutic purpose. By "preventing" is intended that the combination of agents is provided prophylactically, i.e., the herpesvirus vector particle is provided in advance of any symptom. The prophylactic administration of the herpesvirus vector particle serves to prevent or attenuate any subsequent symptom. When provided therapeutically, the substance is provided at (or shortly after) the onset of a symptom. The therapeutic administration of the substance serves to attenuate any actual symptom. In specific embodiments, the subject undergoing treatment with the pharmaceutical formulations of the invention is a human.

Thus, provided are various methods to treat or prevent a variety of cancers, including, but not limited to, melanoma, lymphoma, leukemia, lung cancer, bladder cancer, colon cancer, breast cancer, prostate cancer, esophageal cancer, liver cancer, pancreatic cancer, ovarian cancer, non-small cell lung cancer, renal cancer, neuroblastoma, colorectal cancer, uterine cancer, acute myelocytic leukemia, sarcomas, brain cancer, bone cancer, basal cell carcinoma, cervical cancer, colorectal cancer, endometrial cancer, Ewing sarcoma, retinoblastoma, gastric cancer, gastrointestinal cancer, testicular cancer, glioma, head and neck cancer, hepatocellular cancer, kidney cancer, oral cancer, melanoma, multiple myeloma, nasopharyngeal cancer, thyroid cancer, rectal cancer, skin cancer, squamous cell carcinoma, throat cancer, AIDS related cancers such as Kaposi sarcoma and lymphoma, etc. or any antigenic portion thereof. Such methods can include increasing the immune response in the subject against a tumor-associated antigen of any one of the cancers to be targeted.

Thus, also provided are various methods to treat or prevent a variety of infectious diseases caused by bacterium, virus, protozoan, mycoplasma, fungus, yeast, parasites, or prion including, but not limited to, increasing the immune response in the subject against human immunodeficiency virus 1 or 2, a herpes virus such as herpes simplex or herpes zoster, other retroviruses, such Human T-cell Lymphotropic Virus, a hepatitis virus, an influenza virus, a rhinovirus, respiratory syncytial virus, cytomegalovirus, adenovirus, Mycoplasma pneumoniae, polio viruses, hepatitis A virus, human coxsackie viruses, echoviruses, equine encephalitis viruses, rubella viruses, dengue viruses, encephalitis viruses, yellow fever viruses, coronaviruses, vesicular stomatitis viruses, rabies viruses, Ebola viruses, parainfluenza viruses, mumps virus, measles virus, Hantaan viruses, bunga viruses, hemorrhagic fever viruses, reoviruses, orbiviruses, rotaviruses, Hepatitis B virus, parvoviruses, papilloma viruses, polyoma viruses, adenoviruses), herpes simplex virus (HSV) 1 and 2, varicella zoster virus, cytomegalovirus (CMV), variola viruses, vaccinia viruses, pox viruses, African swine fever virus, the unclassified agent of delta hepatitis, the agents of non-A, non-B hepatitis; a bacterium of the genus *Salmonella, Staphylococcus, Streptococcus, Enterococcus, Clostridium, Escherichia, Klebsiella, Vibrio, Mycobacterium*, amoeba, a malarial parasite, *Trypanosoma cruzi, Helicobacter pylori, Borrelia burgdorferi, Legionella pneumophila, Mycobacterium tuberculosis, Mycobacterium bovis* (BCG), *Mycobacterium avium, Mycobacterium intracellulare, Staphylococcus aureus, Neisseria gonorrhoeae, Neisseria meningitidis, Listeria monocytogenes, Streptococcus pyogenes, Streptococcus pneumoniae, Haemophilus influenzae, Moraxella catharralis, Klebsiella pneumoniae, Bacillus anthracia, Corynebacterium diphtheriae, Clostridium perfringens, Clostridium tetani, Enterobacter aerogenes, Klebsiella pneumoniae, Pasteurella multocida*, and *Treponema pallidum*; infectious fungi like: *Cryptococcus neoformans, Histoplasma capsulatum, Coccidioides immitis, Blastomyces dermatitidis, Candida albicans*; and infectious protists like, for example: *Plasmodium falciparum, Trypanosoma cruzi, Leishmania donovani* and *Toxoplasma gondii*; as well as infectious fungi such as those causing e.g., histoplasmosis, candidiasis, cryptococcosis, blastomycosis and cocidiodomycosis; as well as *Candida* spp. (i.e., *C. albicans, C parapsilosis, C. krusei, C. glabrata, C. tropicalis*, or *C. lusitaniaw*); *Torulopus* spp. (i.e., *T. glabrata*); *Aspergillus* spp. (i.e., *A. fumigalus*), *Histoplasma* spp. (i.e., *H. capsulatum*); *Cryptococcus* spp. (i.e., *C. neoformans*); *Blastomyces* spp. (i.e., *B. dermatilidis*); *Fusarium* spp.; *Trichophyton* spp., *Pseudallescheria boydii, Coccidioides immits*, and *Sporothrix schenckii*, etc or any antigenic portion thereof. Such method can include increasing the immune response in the subject against an antigen of any one of the pathogens to be targeted.

As disclosed elsewhere herein, the methods comprise administering to a subject a therapeutically effective amount of a replication-competent herpesvirus vector particle comprising a polynucleotide comprising a heterologous transgene of interest encoding an antigen of interest, wherein the antigen of interest has been modified to comprise a codon usage signature of a herpesvirus late gene operably linked to an active promoter. In such methods, the therapeutically effective amount of the herpesvirus vector particle produces an improved immune response against the antigen of interest.

The herpesvirus vector particles provided herein can be used as a vaccine to treat various types of cancers. Various tumor-associated antigens can be used, including, for example, BAGE, GAGE, MAGE, NY-ESO-1, SSX, gp100, Melan-A/Mart-1, Tyrosinase, PSA, CEA, Mammaglobin-A, p53, HER-2/neu, livin, survivin, ß-catenin-m, ß-Actin/4/m, Myosin/m, HSP70-2/m, HLA-A2-R17OJ, GM2, GD2, GD3, MUC-1, sTn, globo-H, WT1, PR1, E75, ras, alpha fetoprotein (AFP), URLC10, VEGFR1 and 2, mutant p53, NY-ESO-1, HPV16 E7, ß-catenin, CDK4, CDC27, α actinin-4, TRP1/gp75, TRP2, gangliosides, PSMA, HER2, WT1, EphA3, EGFR, CD20, telomerase, MART-1 or any antigenic portion thereof.

In addition, the herpesvirus vector particles provided herein can be used as a vaccine to *Plasmodium*(P.) parasites causing malaria. Various *Plasmodium*(P.) parasites antigens can be used, including, for example, an antigen from *P. falciparum*.

Thus, the herpesvirus vector particles provided herein can be used as a vaccine to *Mycobacterium tuberculosis* causing tuberculosis. Various *Mycobacterium tuberculosis* antigens can be used, including, for example, a *Mycobacterium tuberculosis* antigen comprising the 65 kD heat shock protein (HSP65), antigen 85A (Ag85A), antigen 85B, antigen 85C, ESAT-6, Des protein, MPT32, MPT51, MPT63, MPT64, HspX and/or Phosphate binding protein 1.

In other embodiments, the herpesvirus vector particles provided herein can be used as a vaccine to *Bacillus anthracis* causing anthrax. Various *Bacillus anthracis* antigens can be used, including, for example, a *Bacillus anthracis* antigen comprising PA (protective antigen), LF (lethal antigen) or EA (edema antigen), and more preferably PA (protective antigen).

In addition, the herpesvirus vector particles provided herein can be used as a vaccine to HAV (Hepatitis A virus) causing Hepatitis A. Various HAV antigens can be used, including, for example, a HAV antigen comprising VP1, VP2, VP3, VP4, 2A, 2B, 2C, 3A, 3B, 3C and 3D protein.

The herpesvirus vector particles provided herein can be used as a vaccine to HBV (Hepatitis B virus) causing Hepatitis B. Various HBV antigens can be used, including, for example, a HBV antigen comprising HBcAg (core antigen of HBV) or HBsAg (surface antigen of HBV), and more preferably HBsAg.

In addition, the herpesvirus vector particles provided herein can be used as a vaccine to HCV (Hepatitis C virus) causing Hepatitis C. Various HCV antigens can be used, including, for example, a HCV antigen comprising E1, E2 or NS3/4a antigen, and more preferably NS3.

The herpesvirus vector particles provided herein can be used as a vaccine to HIV causing AIDS. Various HIV antigens can be used, including, for example, a HIV antigen comprising Gag (p55gag), Pol, Vif, Vpr, Tat, Rev, Vpu, Env or Nef antigen, and more preferably an Env antigen.

In addition, the herpesvirus vector particles provided herein can be used as a vaccine to influenza causing influenza. Various influenza antigens can be used, including, for example, an influenza antigen comprising an envelope glycoprotein HA or NA, and more preferably envelope glycoprotein HA.

In other embodiments, the herpesvirus vector particles provided herein can be used as a vaccine to Dengue virus causing Dengue fever and dengue hemorrhagic. Various Dengue virus antigens can be used, including, for example, antigens from DENV 1, DENV 2, DENV 3, or DENV 4.

Examples of possible routes of administration for the herpesvirus vectors include, for example, administration by oral (solid or liquid), parenteral (intramuscular, intraperitoneal, intravenous (IV) or subcutaneous injection), transdermal (either passively or using ionophoresis or electroporation), transmucosal and systemic (nasal, vaginal, rectal, or sublingual), or inhalation routes of administration, or using bioerodible inserts and can be formulated in dosage forms appropriate for each route of administration.

In some embodiments, the method comprises administration of multiple doses of the herpesvirus vector disclosed herein. The frequency and duration of administration of multiple doses of the herpesvirus vector is such as to allow for a therapeutic effect, which in some embodiments comprises an increased immune response against the antigen of interest. Moreover, treatment of a subject with a therapeutically effective amount of a herpesvirus vector disclosed herein can include a single treatment or can include a series of treatments. It will also be appreciated that the effective dosage of the herpesvirus vector disclosed herein may increase or decrease over the course of a particular treatment. Changes in dosage may result and become apparent from the results of diagnostic assays known in the art.

It is further recognized that the therapeutically effective dose of the herpesvirus vector particle may be administered intermittently. By "intermittent administration" is intended administration of a therapeutically effective dose of a herpesvirus vector particle disclosed herein, followed by a time period of discontinuance, which is then followed by another administration of a therapeutically effective dose, and so forth. The preferred length of the discontinuance period depends on the disorder being treated. The discontinuance period can be at least 1, 2, 4, 6, 8, 10, 12, 14, 16, 18, 20, 22, 24 months or greater. An intermittent schedule of administration of the herpesvirus vector particle can continue until the desired therapeutic effect is achieved.

Generally, the dosage of the combination of agents will vary depending upon such factors as the patient's age, weight, height, sex, general medical condition and previous medical history. In some aspects, patients can be administered the herpesvirus vector disclosed herein in one or more doses, including, for example, 1, 2, 3, 4, 5, 6, 7, 8, 9, 10 or more doses. The administrations can occur over any time period. In specific embodiments, the number of administrations will be sufficient to establish the protective immune response, particularly with respect to the primary immunization schedule. In some aspects, boosters can be administered at regular intervals such as every 2, 3, 4, 5, or 6 days, every 2, 3, 4, 5, 6, 7, 8, 9, 10, or more weeks, or every 2, 3, 4, 5, 6, 7, 8, 9, 10, 11, 12, or more months or every 1, 2, 3, 4, 5, 10, or 20 years. Boosters can also be administered on an as-needed basis. The dose will be determined by the immunological activity of the composition produced and the condition of the patient, as well as the body weight or surface areas of the patient to be treated. The size of the dose also will be determined by the existence, nature, and extent of any adverse side effects that may accompany the administration of a particular composition in a particular patient.

A vaccine administration schedule, including primary immunization and booster administration, can continue as long as needed for the subject, for example, over the course of several weeks, to several months, to several years, to over the lifetime of the patient. In some aspects, the vaccine schedule includes more frequent administration at the beginning of the vaccine regimen, and includes less frequent administration (e.g. boosters) over time to maintain the protective immunity. "Booster" refers to a dose of the herpesvirus vector particle administered to a patient to enhance, prolong, or maintain protective immunity.

A therapeutically effective amount of a herpesvirus particle disclosed herein comprises from about $5\times10^7$ to about $4\times10^3$ virus particles, from about $4\times10^6$ to about $5\times10^4$ infectious virus particles, from about $4\times10^5$ to about $5\times10^5$ infectious virus particles, or from about $4\times10^7$ to about $5\times10^7$ infectious virus particles.

It is further recognized that in specific embodiments, lower viral titers can be used. A "sufficient concentration" of herpesvirus vector particles will allow for the expression of the transgene of interest in a single target cell, but need not result in a therapeutic effect. Methods to assay for such an event are well known in the art.

For avian subjects, individual administration systems may not by practicable if a large number of birds require administration, so application by spray, or via feed or drinking water may be more appropriate. For smaller numbers of birds, it may be possible to treat each bird individually, which usually results in a more uniform dosage. Individual administration methods include eye drop administration, intranasal administration and parenteral delivery.

There may be different composition/formulation requirements dependent on the different delivery systems for avian subjects. By way of example, the herpesvirus particle can be formulated to be delivered by an oral route (e.g. in drinking water or feed, or by spray application) by a mucosal route, or parenterally in which the composition is formulated by an injectable form, for delivery, by, for example, an intravenous, intramuscular or subcutaneous route.

The composition may be formulated for in ovo or post-hatch delivery. The term "in ovo", means into a bird egg containing a live, developing embryo. The term "administering in ovo" or "in ovo administration", means administering the vaccine to a bird egg containing a live, developing embryo by any means of penetrating the shell of the egg and introducing the vaccine. Such means of administration include, but are not limited to, injection of the vaccine.

Various in ovo administration method are known in the art. An injection method may include the steps of making a hole is made in the egg shell at the large end of the egg using an appropriate needle to expose the egg's air cell, inserting a needle connected to a syringe through the hole and through the membrane of the air cell and then injecting the vaccine into the egg. The site of injection can be within any region of the egg or embryo. Preferably, injection is done axially through the centre of the large end of the egg into the amnion. An automated egg injection system can be used. Such systems known in the art (see for example U.S. Pat. Nos. 4,681,063, 4,040,388, 4,469,047, and 4,593,646).

Post-hatch vaccination systems for birds include spray applications and administration via feed or drinking water.

For spray applications a special cabinet may be used. Chicks can be vaccinated in the hatchery because the sprayer enables uniform distribution. A certain amount of spray (such as 20 ml) is delivered for each box of 100 chicks. Chicks "preen" to clean and dry their feathers and ingest the vaccine. Red dye mixed in with the vaccine gets their attention and stimulates preening, and also indicates which boxes of chicks have been vaccinated.

Administration via feed/drinking water is less uniform that spraying due to differences in uptake between birds. There is also a possible contamination problem. However, this type of administration is possible for older birds (i.e. when hatchery application is not possible).

Where the composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

VII. Sequence Identity

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Non-limiting embodiments include:

1. A replication-competent herpesvirus vector system comprising a polynucleotide comprising a heterologous recombinant transgene of interest operably linked to a promoter, wherein said recombinant transgene has been modified to comprise a codon usage signature of at least one (e.g., one, two, three, four, five) herpesvirus late gene and wherein the at least one herpesvirus late gene corresponds to the herpesvirus vector system.

2. The replication-competent herpesvirus vector system of embodiment 1, wherein said herpesvirus vector system is derived from a Gammaherpesvirus.

3. The replication-competent herpesvirus vector system of embodiment 2, wherein said Gammaherpesvirus is a gamma-2 herpesvirus.

4. The replication-competent herpesvirus vector system of embodiment 3, wherein the gamma-2 herpesvirus is a gamma-2 KSHV-related herpesvirus.

5. The replication-competent herpesvirus vector system of embodiment 4, wherein said gamma-2 KSHV-related herpesvirus comprises human KSHV and said polynucleotide comprising the heterologous recombinant transgene of interest comprises a codon usage signature of the human KSHV late genes.

6. The replication-competent herpesvirus vector system of embodiment 4, wherein said gamma-2 KSHV-related herpesvirus comprises a human KSHV vector system and said polynucleotide comprising the heterologous recombinant transgene of interest comprises a codon usage signature of the gH polypeptide of human KSHV.

7. The replication-competent herpesvirus vector system of any one of embodiments 1-6, wherein said heterologous recombinant transgene of interest encodes an antigen.

8. The replication-competent herpesvirus vector system of embodiment 7, wherein said antigen is a microbial antigen.

9. The replication-competent herpesvirus vector system of embodiment 8, wherein said microbial antigen comprises a viral antigen, a parasitic antigen, a mycobacteria antigen, or a bacterial antigen.

10. The replication-competent herpesvirus vector system of embodiment 9, wherein said viral antigen comprises a viral antigen from Retrovirdae or Flaviviridae.

11. The replication-competent herpesvirus vector system of embodiment 10, wherein said viral antigen comprises a viral antigen from a dengue virus, a lentivirus, an HIV virus or an SIV virus.

12. The replication-competent herpesvirus vector system of any of embodiments 9, 10, and 11, wherein said viral antigen comprises an envelope polypeptide.

13. The replication-competent herpesvirus vector system of embodiment 12, wherein said envelope polypeptide is from HIV or SIV.

14. The replication-competent herpesvirus vector system of embodiment 13, wherein said recombinant transgene comprises the polynucleotide set forth in SEQ ID NO: 1 or a polynucleotide having at least 90% sequence identity to SEQ ID NO:1, wherein said polynucleotide provides an improved immune response when compared to the appropriate control (e.g., when compared to a recombinant transgene that encodes the envelope polypeptide from HIV or SIV but that lacks the codon usage signature).

15. The replication-competent herpesvirus vector system of embodiment 9, wherein said bacterial antigen is from *Mycobacterium tuberculosis.*

16. The replication-competent herpesvirus vector system of embodiment 8, wherein said microbial antigen is from *plasmodium.*

17. The replication-competent herpesvirus vector system of embodiment 7, wherein said antigen is a tumor-associated antigen.

18. The replication-competent herpesvirus vector system of embodiment 17, wherein said tumor-associated antigen is associated with melanoma, lymphoma, leukemia, lung cancer, bladder cancer, colon cancer, breast cancer, prostate cancer, esophageal cancer, liver cancer, pancreatic cancer, ovarian cancer, non-small cell lung cancer, renal cancer, neuroblastoma, colorectal cancer, uterine cancer, acute myelocytic leukemia, sarcoma, brain cancer or bone cancer.

19. The replication-competent herpesvirus vector system of any of embodiments 17 and 18, wherein said tumor-associated antigen comprises BAGE, GAGE, MAGE, NY-ESO-1, SSX, gp100, Melan-A/Mart-1, Tyrosinase, PSA, CEA, Mammaglobin-A, p53, HER-2/neu, livin, survivin, ß-catenin-m, ß-Actin/4/m, Myosin/m, HSP70-2/m, HLA-A2-R17OJ, GM2, GD2, GD3, MUC-1, sTn, globo-H, WT1, PR1, E75, ras, AFP, URLC10, VEGFR1 and 2, mutant p53, NY-ESO-1, HPV16 E7, ß-catenin, CDK4, CDC27, α actinin-4, TRP1/gp75, TRP2, gangliosides, PSMA, HER2, WT1, EphA3, EGFR, CD20, telomerase, MART-1, or an antigenic portion thereof.

20. A cell line comprising the replication-competent herpesvirus vector system of any one of embodiments 1-16.

21. A cell line comprising the replication-competent herpesvirus vector system of any one of embodiments 1-7 and 17-19.

22. A replication-competent herpesvirus vector particle comprising within its genome a polynucleotide comprising a heterologous recombinant transgene of interest operably linked to a promoter, wherein said recombinant transgene has been modified to comprise a codon usage signature of at least one (e.g., one, two, three, four, five) herpesvirus late gene, wherein the at least one herpesvirus late gene corresponds to the herpesvirus vector.

23. The replication-competent herpesvirus vector particle of embodiment 22, wherein said herpesvirus particle is from a Gammaherpesvirus.

24. The replication-competent herpesvirus vector particle of embodiment 23, wherein said Gammaherpesvirus is a gamma-2 herpesvirus.

25. The replication-competent herpesvirus vector particle of embodiment 24, wherein the gamma-2 herpesvirus is a gamma-2 KSHV-related herpesvirus.

26. The replication-competent herpesvirus vector particle of embodiment 25, wherein said gamma-2 KSHV-related herpesvirus comprises a human KSHV and said polynucleotide comprising the heterologous recombinant transgene of interest comprises a codon usage signature of the KSHV late genes.

27. The replication-competent herpesvirus vector particle of embodiment 25, wherein said gamma-2 KSHV-related herpesvirus comprises a human KSHV and said polynucleotide comprising the heterologous recombinant transgene of interest comprises a codon usage signature of the gH polypeptide of human KSHV.

28. The replication-competent herpesvirus vector particle of any one of embodiments 22-27, wherein said heterologous recombinant transgene of interest encodes an antigen.

29. The replication-competent herpesvirus vector particle of embodiment 28, wherein said antigen is a microbial antigen.

30. The replication-competent herpesvirus vector particle of embodiment 29, wherein said microbial antigen comprises a viral antigen, a parasitic antigen, a mycobacteria antigen or a bacterial antigen.

31. The replication-competent herpesvirus vector particle of embodiment 30, wherein said viral antigen is from Retrovirdae or Flaviviridae.

32. The replication-competent herpesvirus vector particle of embodiment 31, wherein said viral antigen is from HIV or SIV.

33. The replication-competent herpesvirus vector particle of embodiment 32, wherein said viral antigen comprises an envelope polypeptide.

34. The replication-competent herpesvirus particle of embodiment 33, wherein said envelope polypeptide is from HIV or SIV.

35. The replication-competent herpesvirus vector particle of embodiment 34, wherein said recombinant transgene comprises the polynucleotide set forth in SEQ ID NO: 1 or a polynucleotide having at least 90% sequence identity to SEQ ID NO:1, wherein said polynucleotide provides an improved immune response when compared to the appropriate control (e.g., when compared to a recombinant transgene that encodes the envelope polypeptide from HIV or SIV but that lacks the codon usage signature).

36. The replication-competent herpesvirus vector particle of embodiment 30, wherein said bacterial antigen is from *Mycobacterium tuberculosis.*

37. The replication-competent herpesvirus vector particle of embodiment 29, wherein said microbial antigen is from *plasmodium.*

38. The replication-competent herpesvirus vector particle of embodiment 28, wherein said antigen is a tumor-associated antigen (e.g., a tumor-associated antigen from a human).

39. The replication-competent herpesvirus vector particle of embodiment 38, wherein said tumor-associated antigen is associated with melanoma, lymphoma, leukemia, lung cancer, bladder cancer, colon cancer, breast cancer, prostate cancer, esophageal cancer, liver cancer, pancreatic cancer, ovarian cancer, non-small cell lung cancer, renal cancer, neuroblastoma, colorectal cancer, uterine cancer, acute myelocytic leukemia, sarcomas, brain cancer or bone cancer.

40. The replication-competent herpesvirus vector particle of any of embodiments 38 and 39, wherein said tumor-associated antigen comprises BAGE, GAGE, MAGE, NY-ESO-1, SSX, gp100, Melan-A/Mart-1, Tyrosinase, PSA, CEA, Mammaglobin-A, p53, HER-2/neu, livin, survivin, ß-catenin-m, ß-Actin/4/m, Myosin/m, HSP70-2/m, HLA-A2-R17OJ, GM2, GD2, GD3, MUC-1, sTn, globo-H, WT1, PR1, E75, ras, AFP, URLC10, VEGFR1 and 2, mutant p53, NY-ESO-1, HPV16 E7, ß-catenin, CDK4, CDC27, α actinin-4, TRP1/gp75, TRP2, gangliosides, PSMA, HER2, WT1, EphA3, EGFR, CD20, telomerase, MART-1 or an antigenic portion thereof.

41. A pharmaceutical composition comprising the replication-competent herpesvirus vector particle of any one of embodiments 22-37.

42. A pharmaceutical composition comprising the replication-competent herpesvirus vector particle of any one of embodiments 22-28 and 38-40.

43. A method for delivering a transgene of interest to a cell comprising contacting the cell with a replication-competent herpesvirus vector particle of any one of embodiments 22-37.

44. The method of embodiment 43, wherein said cell is contacted in vivo or in vitro.

45. The method of embodiment 44, wherein said cell is from a mammal or an avian.

46. A method for delivering a transgene of interest to a cell comprising contacting the cell with a replication-competent herpesvirus vector particle of any one of embodiments 22-28 and 38-40.

47. The method of embodiment 46, wherein said cell is contacted in vivo or in vitro.

48. The method of embodiment 47, wherein said cell is from a mammal or avian.

49. A method of generating an immune response against an antigen of interest in a subject in need thereof comprising administering to said subject a therapeutically effective amount of the replication competent herpesvirus vector particle of any one of embodiments 22-40, wherein an immune response against said antigen of interest is generated in said subject.

50. A method of generating an immune response against a microbial antigen in a subject in need thereof comprising administering to said subject a therapeutically effective amount of the replication competent herpesvirus vector particle of any one of embodiments 22-37, wherein an immune response against said microbial antigen is generated in said subject.

51. A method of generating an immune response against a tumor-associated antigen in a subject in need thereof comprising administering to said subject a therapeutically effective amount of the replication competent herpesvirus vector particle of any one of embodiments 22-28 and 38-40, wherein an immune response against said tumor-associated antigen is generated in said subject.

52. A method for treating or preventing a microbial infection in a subject in need thereof comprising administering to said subject a therapeutically effective amount of a replication-competent herpesvirus vector particle comprising within its genome a polynucleotide comprising a heterologous recombinant transgene encoding a microbial antigen and operably linked to a promoter, wherein said recombinant transgene has been modified to comprise a codon usage signature of at least one herpesvirus late gene, wherein the at least one herpesvirus late gene corresponds to the herpesvirus vector, and wherein an immune response against said microbial antigen is generated in said subject and thereby treats or prevents said microbial infection.

53. The method of embodiment 52, wherein said microbial infection is HIV.

54. The method of embodiment 52, wherein said microbial infection is *Mycobacterium tuberculosis, plasmodium*, or a dengue virus.

55. The method of embodiment of 52, wherein the subject is a human.

56. A method for treating or preventing cancer in a subject in need thereof comprising administering to said subject a therapeutically effective amount of a replication-competent herpesvirus vector particle comprising within its genome a polynucleotide comprising a heterologous recombinant transgene encoding a tumor-associated antigen and operably linked to a promoter, wherein said recombinant transgene has been modified to comprise a codon usage signature of at least one herpesvirus late gene, wherein the at least one herpesvirus late gene corresponds to the herpesvirus vector, and wherein an immune response against said tumor-associated antigen is generated in said subject and thereby treats or prevents said cancer.

57. The method of embodiment 56, wherein the subject is a human.

58. The method of embodiment 56, wherein the cancer is melanoma, lymphoma, leukemia, lung cancer, bladder cancer, colon cancer, breast cancer, prostate cancer, esophageal cancer, liver cancer, pancreatic cancer, ovarian cancer, non-small cell lung cancer, renal cancer, neuroblastoma, colorectal cancer, uterine cancer, acute myelocytic leukemia, sarcoma, brain cancer or bone cancer.

59. The method of embodiment 56, wherein the tumor-associated antigen comprises BAGE, GAGE, MAGE, NY-ESO-1, SSX, gp100, Melan-A/Mart-1, Tyrosinase, PSA, CEA, Mammaglobin-A, p53, HER-2/neu, livin, survivin, ß-catenin-m, ß-Actin/4/m, Myosin/m, HSP70-2/m, HLA-A2-R17OJ, GM2, GD2, GD3, MUC-1, sTn, globo-H, WT1, PR1, E75, ras, AFP, URLC10, VEGFR1 and 2, mutant p53, NY-ESO-1, HPV16 E7, ß-catenin, CDK4, CDC27, α actinin-4, TRP1/gp75, TRP2, gangliosides, PSMA, HER2, WT1, EphA3, EGFR, CD20, telomerase, MART-1, or an antigenic portion thereof.

60. A method of making a replication-competent herpesvirus vector particle of any one of embodiments 22-40 comprising introducing into a cell one or more polynucleotides comprising a herpesvirus vector system and culturing said cell under conditions to allow for the formation of a herpesvirus vector particle.

61. The method of embodiment 60, further comprising isolating the replication-competent herpesvirus vector particle.

As used herein, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

The subject matter of the present disclosure is further illustrated by the following non-limiting examples.

EXPERIMENTAL

Example 1. Methods to Generate an RRV gH Codon Signature in SIV 160

The codons marked with * in the natural SIV gp160 coding sequence were changed to the codons denoted by the ** to more reflect the codon usage in RRV glycoproteins. The codon-altered form of the SIVgp160 coding sequence is called d.o.gp160RRV-like. The decisions on what codons in the natural gp160 coding sequence to change was based on the desired to make the transgene more RRV glycoprotein-like in its codon usage.

General Rules Included:

Change from: Codons in the natural gp160 sequence that were highly utilized in the natural gp160 sequence and/or codons in the natural gp160 sequence that were not extensively utilized in RRV gH.

Change to: Codons that were highly utilized in RRV gH and/or codons that were not extensively utilized in the natural gp160 sequence.

| amino acid | Codon | RRV gH | SIV gp160 | human | SIVgp160 having codon usage signature of RRV gH |
|---|---|---|---|---|---|
| Alanine | GCA | 43 | 42 | 23 | 42 |
| | GCC | 24 | 17 | 40 | 17 |
| | GCG | 14 | 21 | 11 | 21 |
| | GCT | 19 | 21 | 27 | 21 |
| Arginine | AGA | 31 | 49 | 21 | 49 |
| | AGG* | 15 | 38 | 21 | 0 |
| | CGA | 8 | 9 | 11 | 9 |
| | CGC | 15 | 4 | 18 | 4 |
| | CGG | 12 | 0 | 20 | 0 |
| | CGT** | 19** | 0** | 8 | 38** |
| Asparagine | AAC | 41 | 28 | 53 | 28 |
| | AAT | 59 | 72 | 47 | 72 |
| Apartic Acid | GAC | 15 | 38 | 54 | 38 |
| | GAT | 85 | 63 | 46 | 63 |
| Cysteine | TGC | 15 | 30 | 54 | 30 |
| | TGT | 85 | 70 | 46 | 70 |
| Glutamine | CAA | 68 | 50 | 27 | 50 |
| | CAG | 32 | 50 | 73 | 50 |
| Glutamic Acid | GAA** | 87** | 49** | 42 | 100** |
| | GAG* | 13 | 51 | 58 | 0 |
| Glycine | GGA** | 62** | 41** | 25 | 54** |
| | GGC | 8 | 21 | 34 | 21 |
| | GGG* | 0 | 18 | 25 | 5 |
| | GGT | 31 | 20 | 16 | 20 |
| Histidine | CAC | 50 | 25 | 58 | 25 |
| | CAT | 50 | 75 | 42 | 75 |
| Isoleucine | ATA | 45 | 43 | 17 | 43 |
| | ATC | 7 | 29 | 47 | 29 |
| | ATT | 47 | 27 | 36 | 27 |
| Leucine | CTA | 7 | 14 | 7 | 14 |
| | CTC* | 1 | 19 | 20 | 2 |
| | CTG | 15 | 13 | 40 | 13 |
| | CTT | 14 | 11 | 13 | 11 |
| | TTA** | 32** | 16** | 8 | 33** |
| | TTG | 31 | 27 | 13 | 27 |
| Lysine | AAA | 83 | 50 | 43 | 50 |
| | AAG | 17 | 50 | 57 | 50 |
| Methionine | ATG | 100 | 100 | 100 | 100 |
| Phenylalanine | TTC | 17 | 42 | 54 | 42 |
| | TTT | 83 | 58 | 46 | 58 |
| Proline | CCA | 29 | 59 | 28 | 59 |
| | CCC | 13 | 16 | 32 | 16 |
| | CCG** | 39** | 6** | 11 | 25** |
| | CCT* | 19 | 19 | 29 | 0 |
| Serine | AGC | 8 | 13 | 24 | 13 |
| | AGT | 21 | 18 | 15 | 18 |
| | TCA | 29 | 22 | 15 | 22 |
| | TCC | 16 | 11 | 22 | 11 |
| | TCG | 11 | 4 | 5 | 4 |
| | TCT | 16 | 31 | 19 | 31 |
| Threonine | ACA | 38 | 36 | 28 | 36 |
| | ACC | 24 | 19 | 36 | 19 |
| | ACG** | 26** | 6** | 11 | 40** |
| | ACT* | 12 | 40 | 25 | 6 |
| Tryptophan | TGG | 100 | 100 | 100 | 100 |
| Tyrosine | TAC | 25 | 28 | 56 | 28 |
| | TAT | 75 | 72 | 44 | 72 |
| Valine | GTA | 32 | 25 | 12 | 25 |
| | GTC | 7 | 31 | 24 | 31 |
| | GTG | 23 | 27 | 46 | 27 |
| | GTT | 38 | 17 | 18 | 17 |
| stop | TAA | 100 | 100 | 30 | 0 |
| | TAG | 0 | 0 | 24 | 0 |
| | TGA | 0 | 0 | 47 | 100 |

Example 2

Glycoproteins of the rhesus monkey rhadinovirus (RRV, a gamma2 KSHV-related herpesvirus) and other herpesviruses have a bad codon usage and are naturally trans-induced by the immediate early gene product ORF57. The viral-encoded glycoproteins of HIV, SIV and related lentiretroviruses also have a bad codon usage and are naturally transinduced by rev. We noticed that the nature of the bad codon usage of RRV gH and gL was different from the bad codon usage of HIV and SIV gp160. We changed the codon usage for six amino acids in a SIV gp160 cassette to reflect the bad codon usage of RRV gH and gL. A total of 10.5% of the codons were changed and the rev-response element (the RRE) was left intact. The effects on expression were astounding. The SIV gp160 with the altered codon usage was no longer trans-induced by rev. However, this codon-altered gp160 cassette was now strongly trans-induced by RRV orf 57. These results indicate that for both SIV rev and RRV orf57, two completely different virus families, transinduction was dependent on the nature of the bad codon usage. Furthermore, the codon-dependent transinduction appears to be intimately tied to cellular proteins called Schlafens. Rev induction of the natural gp160 sequence was potently inhibited by three of the five known Schlafens and orf57 induction of the codon-modified version of gp160 was potently inhibited by all five Schlafens. The inhibitory activity of Schlafen 11 against codon-modified gp160 could be overcome by increasing concentrations of orf57 in a dose-dependent manner. Our results suggest that the cellular Schlafens serve as virus restriction factors for both herpesviruses and lentiviruses and that both orf57 and rev function at least in part to overcome this restriction. These observations have practical applications in attempts to use recombinant RRV as an experimental vaccine approach for AIDS in monkeys. The Desrosiers laboratory has previously published that recombinant RRV-SIVenv with a codon-optimized env cassette and CMV i.e. promoter did NOT elicit detectable anti-env antibody responses in monkeys. However, the new recombinant RRV-SIVenv with altered codon usage and orf57-inducible env expression IS eliciting anti-env antibody responses. This recombinant herpesvirus approach can match, or come close to matching, live attenuated SIV for the degree of vaccine protection.

Example 3. Persisting Viruses: Importance of Codon Usage for the Regulation of Viral Gene Expression Abstract The glycoproteins of herpesviruses and of HIV/SIV are made late in the replication cycle and are derived from transcripts that employ an unusual codon usage that is quite different from that of the host cell. Here we show that the actions of natural transinducers from these two different families of enveloped viruses (rev of SIV and orf57 of the rhesus monkey rhadinovirus) are dependent upon the nature of the skewed codon usage. In fact, transinducibility by rev and by orf57 can be flipped simply by changing the nature of the codon usage. This codon-dependent transinduction appears to be intimately tied to cellular proteins called schlafens. Our findings point to a new general principle in which multiple families of enveloped viruses utilize an unusual, skewed codon usage to temporally regulate late expression of their structural gene products.

Introduction

Some viruses are able to maintain lifelong infections in their natural host despite strong host surveillance measures. Such persisting viruses include members of the herpes, lenti-retro, polyoma, papilloma, and adeno families of viruses. It is perhaps no accident that these five families of persisting viruses strictly regulate their gene expression in a temporal fashion. Structural proteins are made late in the virus replication cycle and expression of these late gene products is typically induced by viral trans-inducers made earlier in the viral replication cycle. A variety of strategies are used by different persisting viruses to achieve this temporal regulation of structural gene expression; these include both transcriptional and post-transcriptional mechanisms. For the gamma-herpesviruses, viral-encoded transcription factors such as the orf50/RTA family of proteins can act on 'late' viral promoters to activate their transcription[1-3] and the viral-encoded orf57 family of proteins act post-transcriptionally to facilitate expression of the late structural genes[4-6].

We have noticed an uncanny set of similarities when comparing the viral-encoded envelope glycoproteins of lenti-retroviruses (the gp160 of HIV and SIV) and the viral-encoded envelope glycoproteins of the herpesviruses. Glycoprotein H of the gamma-2 herpesvirus of rhesus monkeys called RRV (rhesus monkey rhadinovirus) has been used as the example for some of these comparisons[7]. Both gp160 and RRV gH are made late in the lytic cycle of these persistently replicating viruses. They both have an unusual, skewed codon usage. If one puts a strong promoter (such as the CMV immediate early promoter/enhancer) in front of each reading frame and transfects the expression cassette into 293T cells, essentially no protein expression can be detected. There are two ways in which protein expression can be rescued in these assays: by optimizing the codon usage to reflect the major codon usage of the cellular exome or by providing the natural viral-encoded trans-inducer in trans. For HIV and SIV, the natural trans-inducer is the early viral gene product called rev. For RRV, the natural trans-inducer is the early viral gene product called orf57. The levels of viral glycoprotein expression from a codon-optimized sequence far exceed those from the natural coding sequence even when optimal levels of transinducers are provided[7,8]. These observations prompted us to investigate further the influence of codon usage on the regulated expression of viral genes.

Codon Modification of SIV Gp160 and RRV gH

Figure 21A:
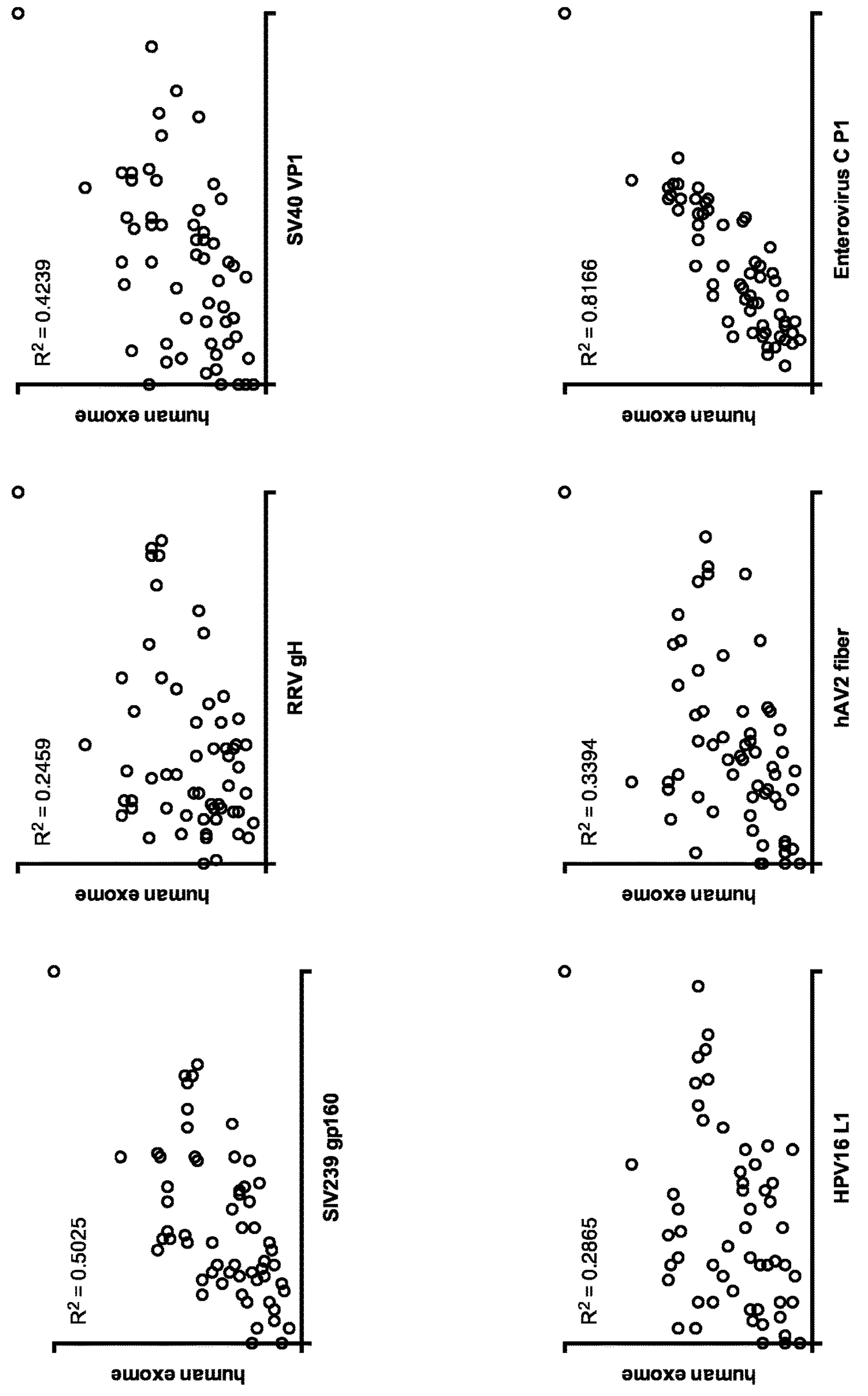
FIG. 21*a*-21*b* shows codon usage of late gene products of five persistent viruses.
Figure 21B:
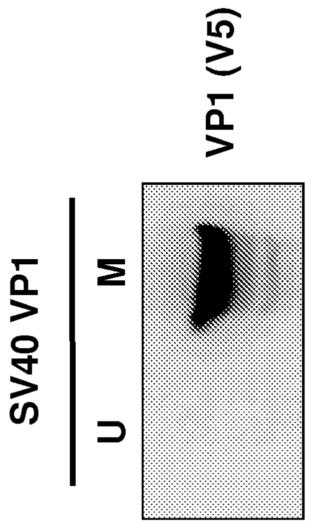

An unusual, skewed codon usage for structural gene products is not confined to the lenti-retro and herpes groups of viruses. Structural gene products of the polyoma, papilloma, and adeno families of persisting viruses also have unusual, skewed codon usage patterns when compared to that of the human exome (FIG. 21*a*). Similar to SIV gp160 and RRV gH, expression of SV40 VP1 from an expression cassette of natural codon usage was below the limit of detection, while codon optimization of VP1 coding sequence led to readily detectable levels of expression (FIG. 21*b*).

Figure 16A:
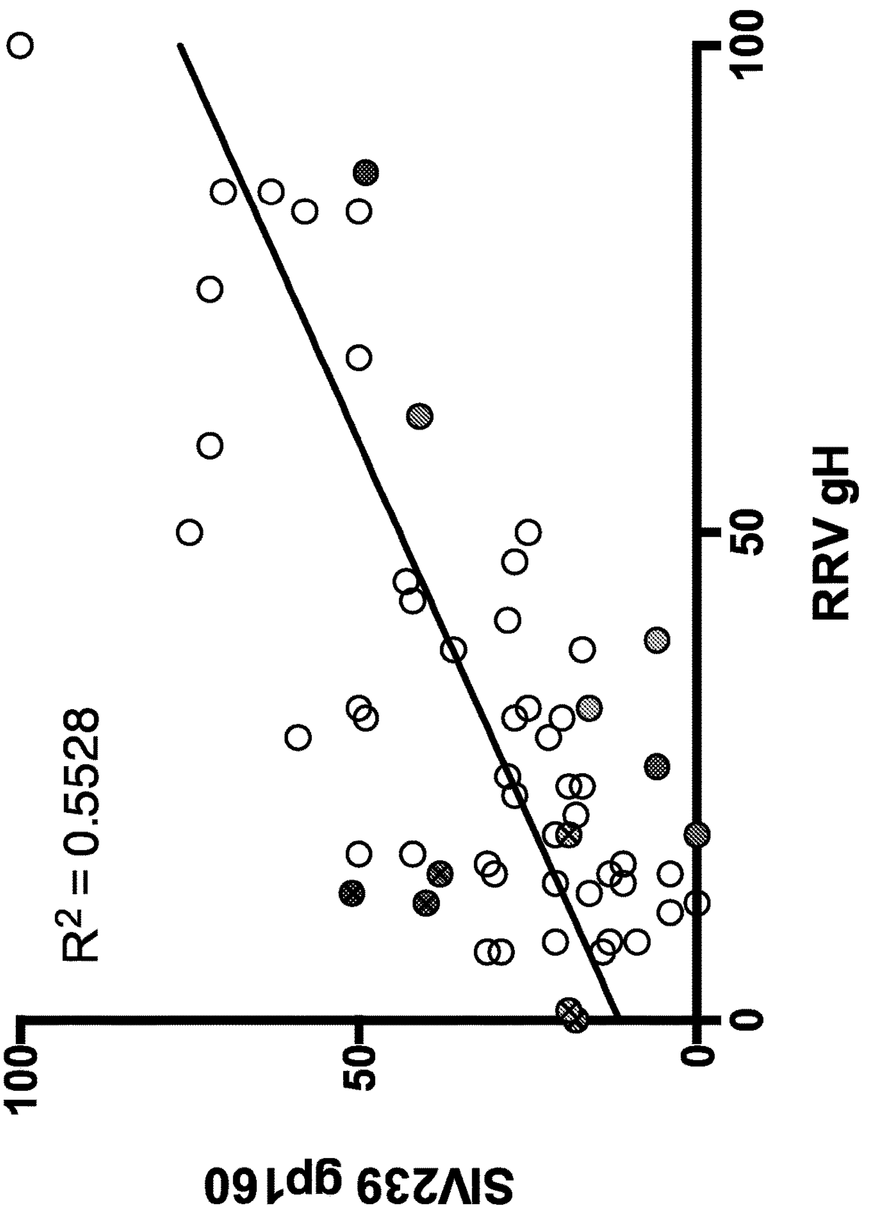
FIG. 16*a*-16*d* shows the influence of codon usage for SIV gp160 and RRV gH.
Figure 16B:
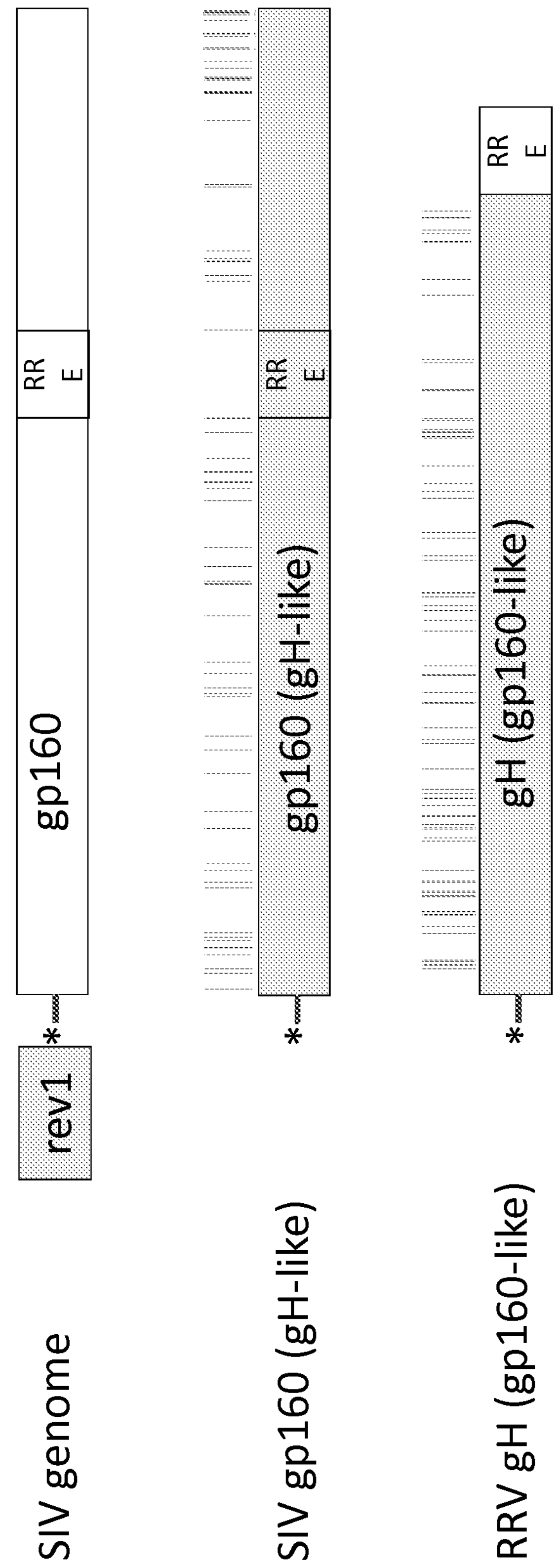

Comparison of the codon usage of SIV gp160 and with that of RRV gH revealed several codons that were overrepresented in one sequence but not the other, i.e. the nature of the unusual skewed codon usage was different (FIG. 16*a* and Table 2). Six codons were chosen based on their bias of usage. To make SIV gp160 more gH-like in its codon usage, codons were changed in a way that reduced the usage of codons that have relatively high frequencies in SIV gp160 and/or increased the usage of codons that have relatively high frequencies in RRV gH. The opposite codon changes were performed to make RRV gH more gp160-like in its codon usage. More specifically, six codons—AGG, GAG, CCT, ACT, CTC, and GGG—in SIV gp160 were changed to CGT, GAA, CCG, ACG, TTA, and GGA, respectively. The number of altered codons was 93, which comprised 10.5% of the total codons in SIV gp160. Conversely, six codons—CGT, GAA, CCG, ACG, TTA, and GGA—in RRV gH were changed to AGG, GAG, CCT, ACT, CTC, and GGG, respectively. The number of altered codons in RRV gH was 104, accounting 14.3% of its total codons (Table 2). The % GC was 43.1%/42.1% in SIV gp160 and 36.5%/40.2% in RRV gH before and after codon modification, respectively. The codon changes in SIV gp160 and RRV gH were distributed rather evenly throughout the entire coding region (FIG. 16*b*). The rev response element (RRE) region in SIV gp160 was not codon-modified; the 1520-1876 nucleotide stretch that contains the RRE[9,10] was left intact. A splicing donor sequence was also present in front of the ATG start codon of each coding sequence since it is required for efficient rev-mediated induction as has been previously noted[11,12].

In Table 3, codons in blue (column 2) were changed to the synonymous codons in red (column 6) to make gp160 more gH-like in its codon usage. Codons in red (column 6) were changed to its synonymous codon in blue (column 2) to make gH more gp160-like in its codon usage. '% in gH' and '% in gp160' indicate the frequency with which that codon is used among the different possible codons for the indicated amino acid in the gH and gp160 coding sequences, respectively. Also shown are the numbers of each codon change in gH and gp160 sequences, and total accumulated changes in the entire coding sequences of gH and gp160, respectively.

| Amino Acid | Codon | % in gH | % in gp160 | % in Human exome | Codon | % in gH | % in gp160 | % in Human exome | # of changes in gp160 (gH-like) | # of changes in gH (gp160-like) |
|---|---|---|---|---|---|---|---|---|---|---|
| Arg | AGG | 15 | 38 | 21 | CGT | 19 | 0 | 8 | 18 | 5 |
| Glu | GAG | 13 | 51 | 58 | GAA | 87 | 49 | 42 | 23 | 33 |
| Pro | CCT | 19 | 19 | 29 | CCG | 39 | 6 | 11 | 6 | 12 |
| Thr | ACT | 12 | 40 | 25 | ACG | 26 | 6 | 11 | 25 | 11 |
| Leu | CTC | 1 | 19 | 20 | TTA | 32 | 16 | 8 | 14 | 27 |
| Gly | GGG | 0 | 18 | 25 | GGA | 62 | 41 | 25 | 7 | 16 |
| | | | | | | | | | 93/880 (10.5%) | 104/726 (14.3%) |

Induction of SIV Gp160 and RRV gH Expression from Codon-Modified Sequences

Figure 16C:
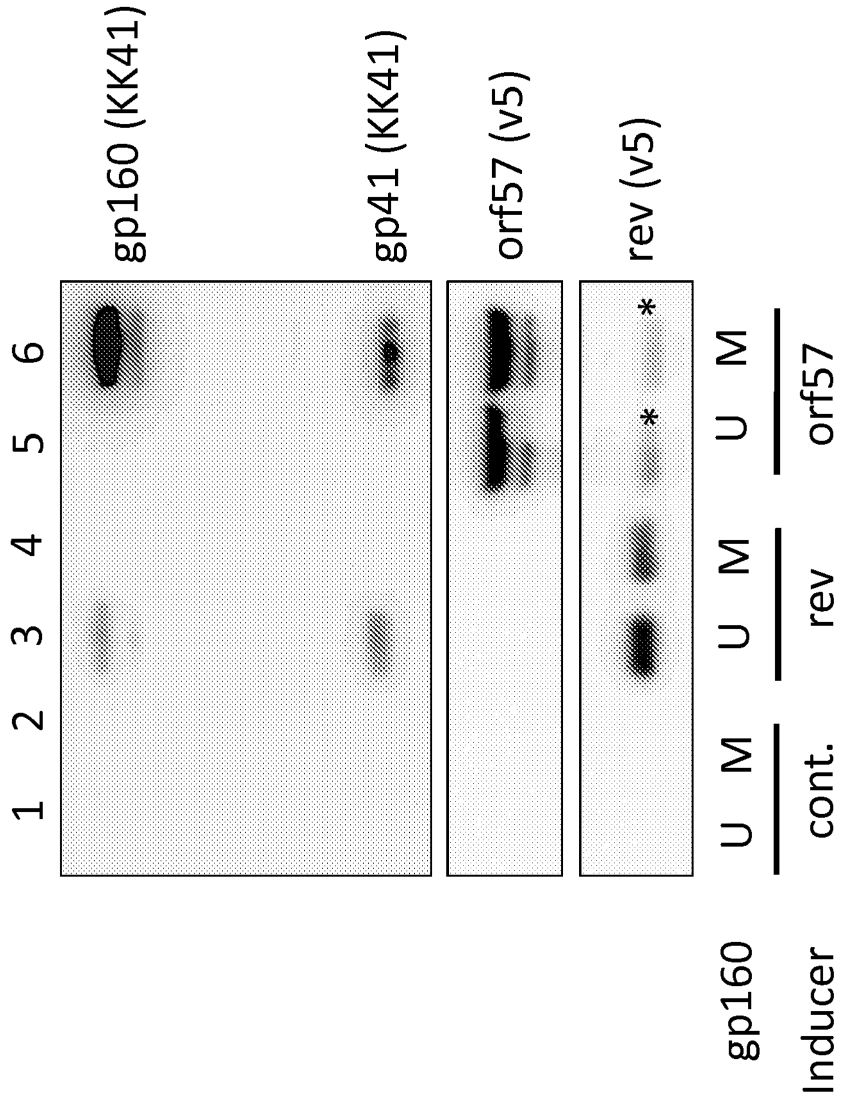

Expression of SIV gp160 from the expression cassette with natural codon usage was not detectable in the absence of any inducer (FIG. 16*c*, lane 1), but was readily detectable in the presence of its natural inducer, rev (FIG. 16*c*, lane 3), as has been repeatedly observed in many previous studies[12, 13]. However, SIV gp160 expression from this cassette was not induced by orf57 (FIG. 16*c*, lane 5), indicating a specific induction of SIV gp160 by rev but not by orf57. The codon-modified version of the SIV gp160 expression cassette, however, showed completely different results. The codon-modified (gH-like) SIV gp160 was again not expressed detectably in the absence of trans-inducer (FIG. 16*c*, lane 2). Surprisingly, it was not induced at all by its natural inducer, rev (FIG. 16*c*, lane 5) even though it still contained the cis-acting sequences RRE and SD that are known to be required for rev-mediated induction. However, expression of this cassette was now very nicely induced by the heterologous inducer, orf57 (FIG. 16*c*, lane 6). Thus, we were amazingly able to switch the induction pattern of SIV gp160 simply by changing the codon usage.

Figure 16D:
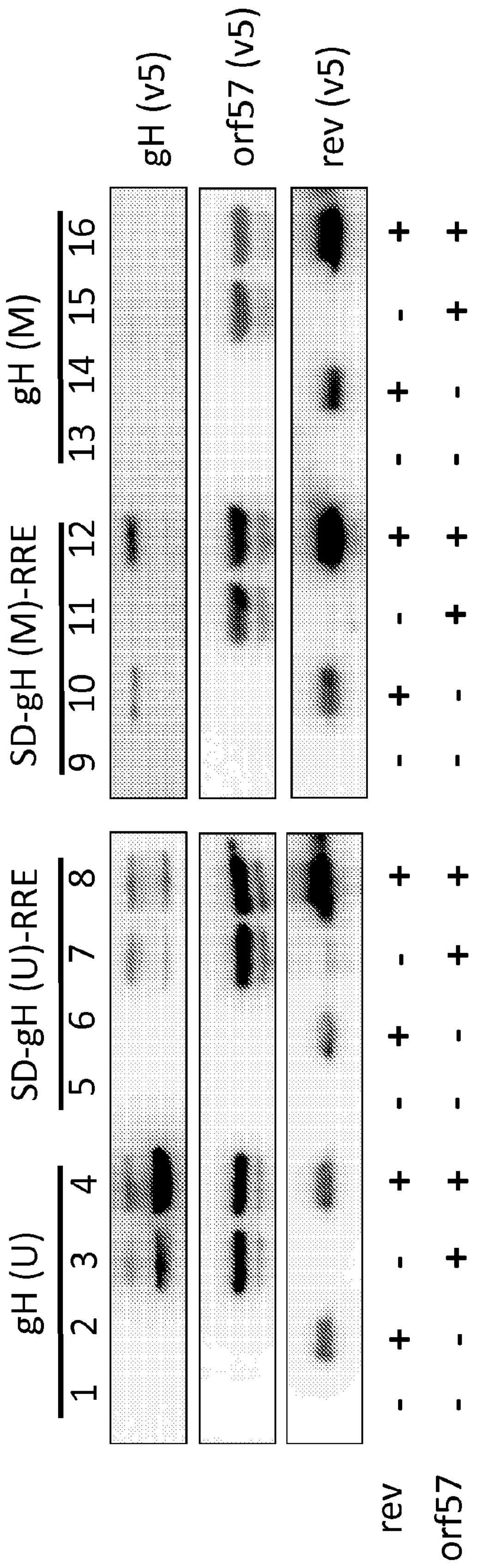

We next sought to do similar experiments by modifying the RRV gH coding sequence to make it more resemble the codon usage of SIV gp160 (FIG. 16*d*). Again, six codons were changed but this time in the exact opposite direction of what was used for the codon changes performed with SIV gp160. Also, to observe any rev-mediated induction, SD and RRE were tethered at the 5' and 3' end of target sequences, respectively. The RRV gH expression cassette with the natural codon usage was inducible by adding its homologous inducer, orf57, but not by rev. However, as observed with codon-modified gp160 above, we could completely switch the induction pattern of RRV gH simply by changing its codon usage. The codon-modified (gp160-like) gH, when tethered by SD and RRE, was inducible by rev but not by orf57 (FIG. 16*d*). No rev-mediated induction was observed in the absence of SD and RRE, again showing the necessity of these cis-acting sequences for rev activity in addition to the nature of the codon usage.

Figure 17A:
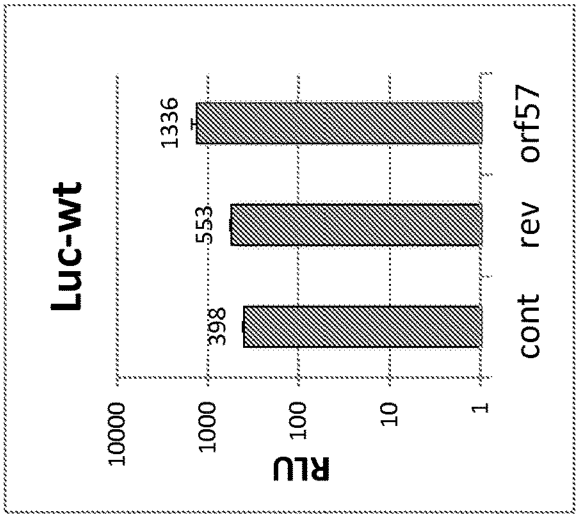
FIG. 17 shows the induction of luciferase from the expression cassettes with unmodified and codon-modified luciferase sequences. The coding sequence of firefly luciferase was modified to make it gp160-like or gH-like (GCC→GCA, CGC→AGG, CGG→AGG, AAC→AAT, TGC→TGT, ATC→ATA, CTG→TTG, CCG→CCA, TAC→TAT, and GTT→GTA to make gp160-like firefly luciferase; GCC→GCA, GAC→GAT, TGC→TGT, ATC→ATA, CTC→TTG, CTG→TTA, AAG→AAA, TTC→TTT, TAC→TAT and GTC→GTA to make gH-like firefly luciferase) and they were further modified by 6 additional codon changes listed in Table 2. Each luciferase sequence was flanked with splicing donor sequence (ctaatacatcttctgcatcaaacaagtaagt (SEQ ID NO: 5)) and the RRE. The levels of firefly luciferase expression from each expression cassette in the presence of empty vector, orf57, or rev were measured. The levels of *renilla* luciferase expression from a pRL-SV plasmid (Promega) were used for calibration of transfection efficiency among the samples.
Figure 17B:
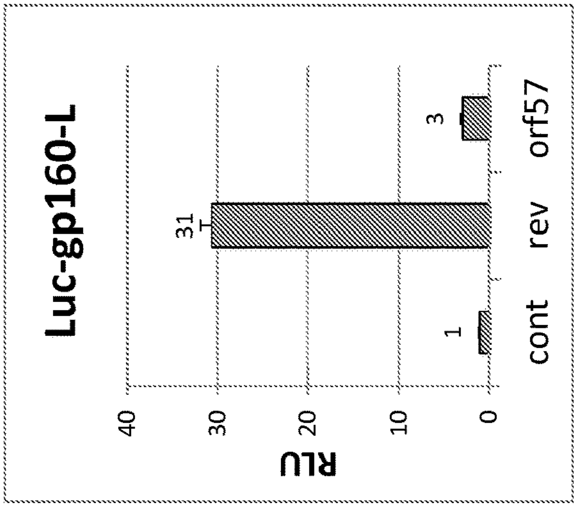
Figure 17C:
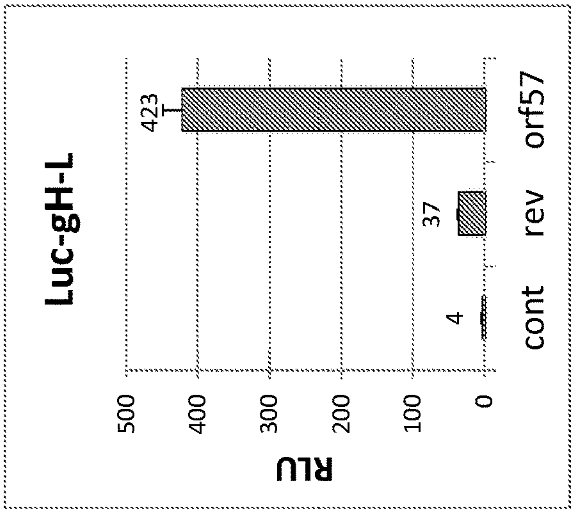

In order to examine the influence of codon usage in a completely different system, we changed the coding sequence of firefly luciferase to make it either RRV gH-like or SIV gp160-like in its codon usage. Expression of firefly luciferase from the expression cassette with natural codon usage was not induced to any appreciable extent by either rev or orf57 (FIG. 17*a*). However, expression of firefly luciferase from the expression cassette with gH-like or gp160-like codon usage was efficiently induced by orf57 or rev, respectively (FIGS. 17*b* and 17*c*).

Rev and Orf57 Overcome Schlafen-Mediated Restriction

Figure 18A:
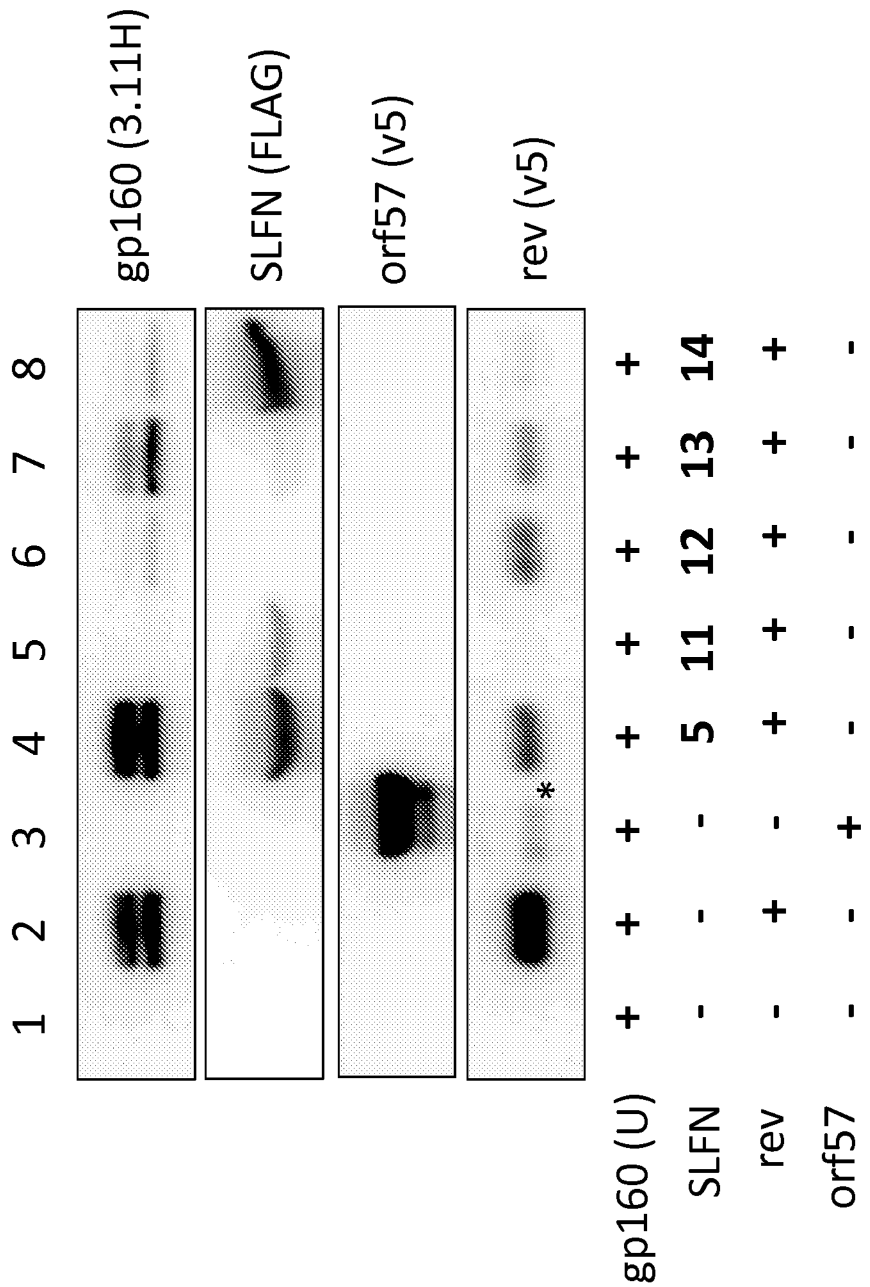
FIG. 18*a*-18*f* shows the regulation of SIV gp160 expression by schlafens. Expression cassettes for gp160 with the unmodified (U) or codon-modified (M, gH-like) SIV gp160 sequence, schlafens, orf57, and rev were transfected into 293T cells as indicated. The expression of each protein was detected using corresponding antibodies by immunoblotting. Each well of 293T cells on a 6-well plate was transfected with increasing amounts of plasmid DNAs (μg) indicated.
Figure 18B:
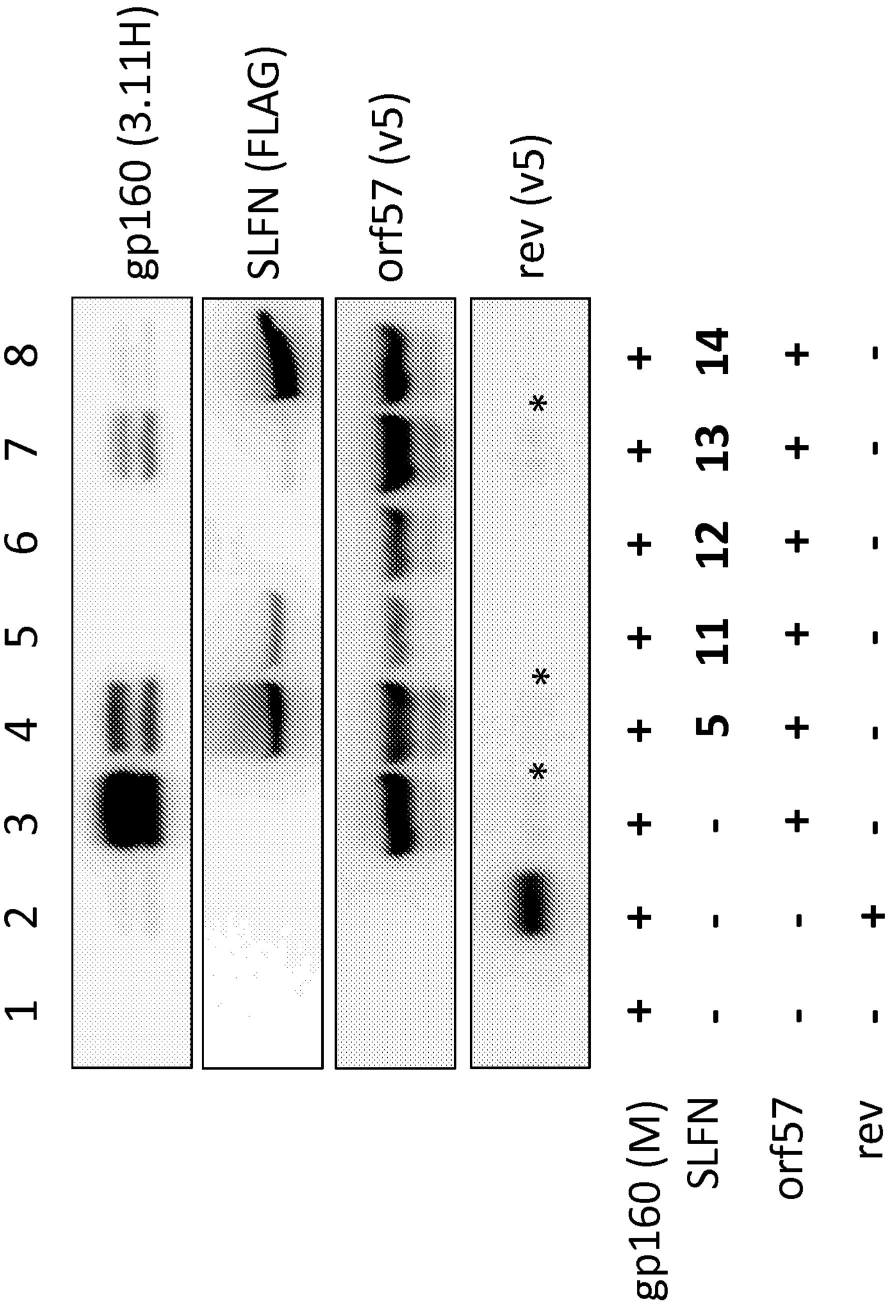

Schlafens are interferon-inducible cellular genes; six human schlafens (5, 11, 12, 12L, 13, and 14) have been identified to date[14]. Li et al. have reported that schlafen 11 restricts HIV-1 gag expression both from proviral clones and from gag expression cassettes[15]. We thus investigated a potential influence of schlafens on the codon usage-dependent trans-inductions that we observed. Rev induction of SIV gp160 from the expression cassette with natural codon usage was potently inhibited by schlafens 11, 12, and 14, less so by schlafen 13, and not at all by schlafen 5 (FIG. 18*a*). Orf57 induction of SIV gp160 from the codon-modified (gH-like) cassette was also potently inhibited by schlafens 11, 12, and 14, less so by schlafen 13, and only modestly by schlafen 5 (FIG. 18*b*).

Figure 18C:
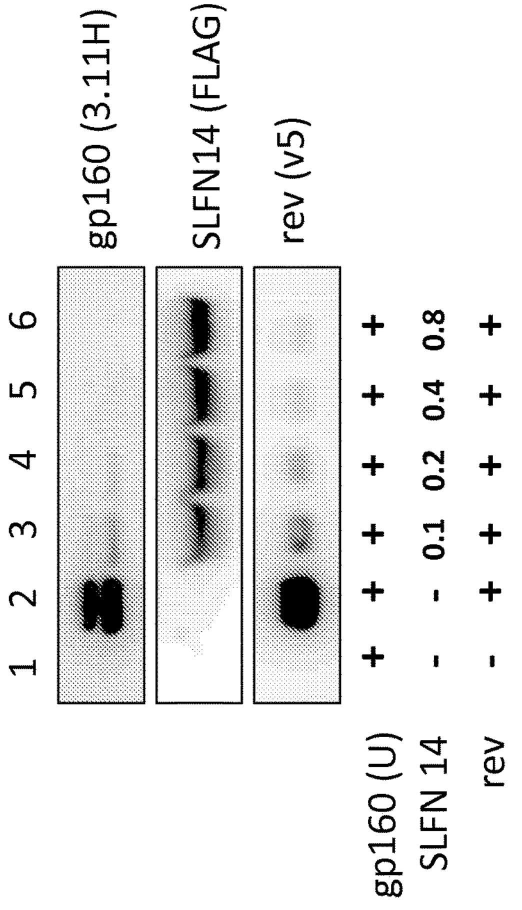
Figure 18D:
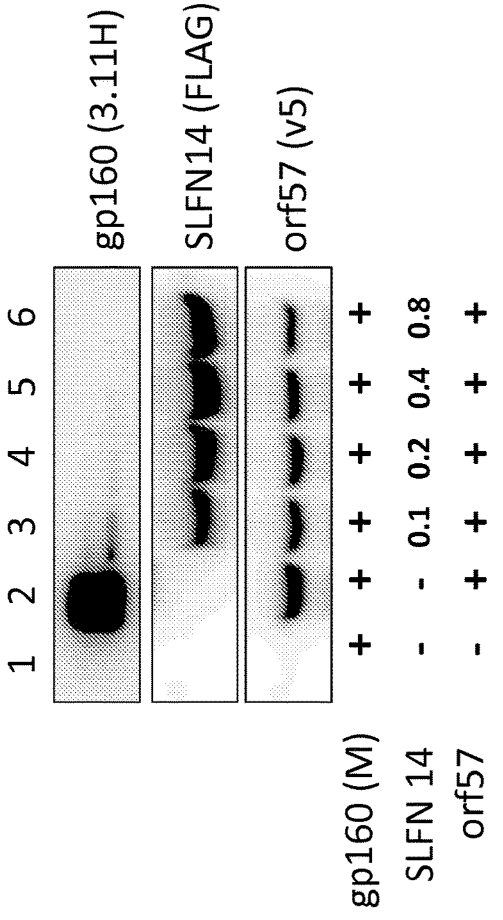
Figure 18E:
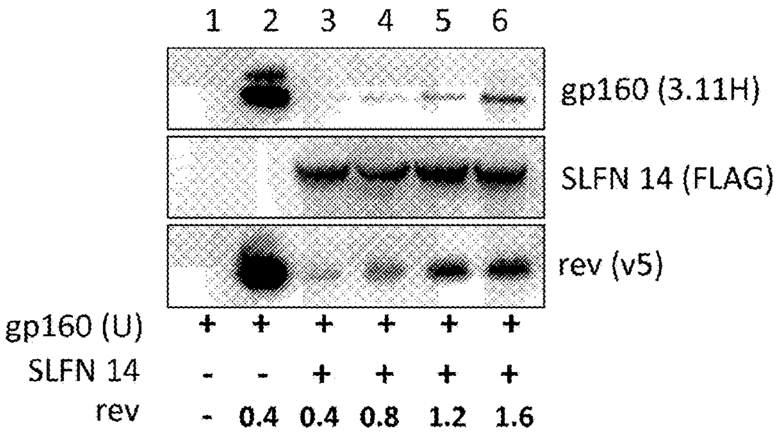
Figure 18F:
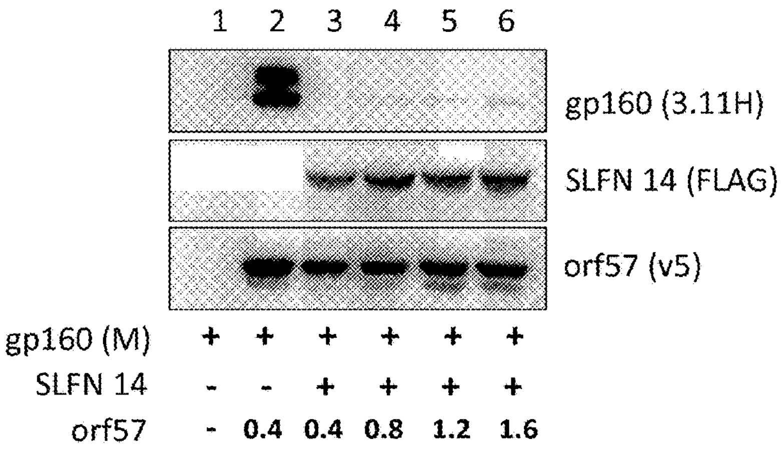

We next examined the dose dependence of schlafen's ability to inhibit rev-induced and orf57-induced expression (FIG. 18*c* and 318). We also examined the ability of increasing amounts of rev and of orf57 to overcome the schlafen-mediated inhibition (FIGS. 18*e* and 18*f*). Schlafen 14 was used for these experiments. In FIGS. 18*c* and *d*, with input DNA amounts for rev and orf57 kept constant, a dose-dependent increase in the ability of schlafen 14 to inhibit rev and orf57 was observed. In FIGS. 18*e* and *f*, with constant DNA amounts for schlafen 14, a dose-dependent increase in the ability of rev or orf57 to overcome the schlafen-mediated inhibition was observed. Thus, both rev and orf57 are able to overcome the restricting effects imposed by schlafen 14.

Figure 19A:
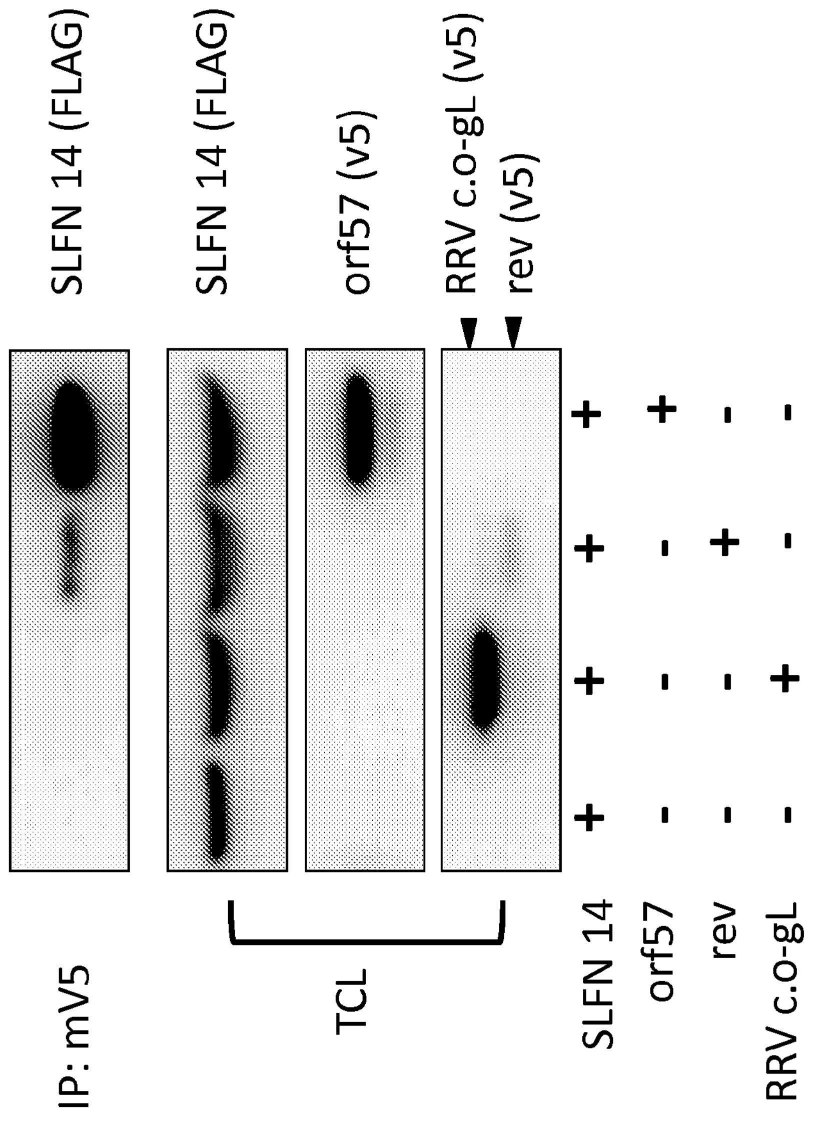
FIG. 19*a*-19*b* shows the interaction of schlafen 14 with rev and orf57.
Figure 19B:
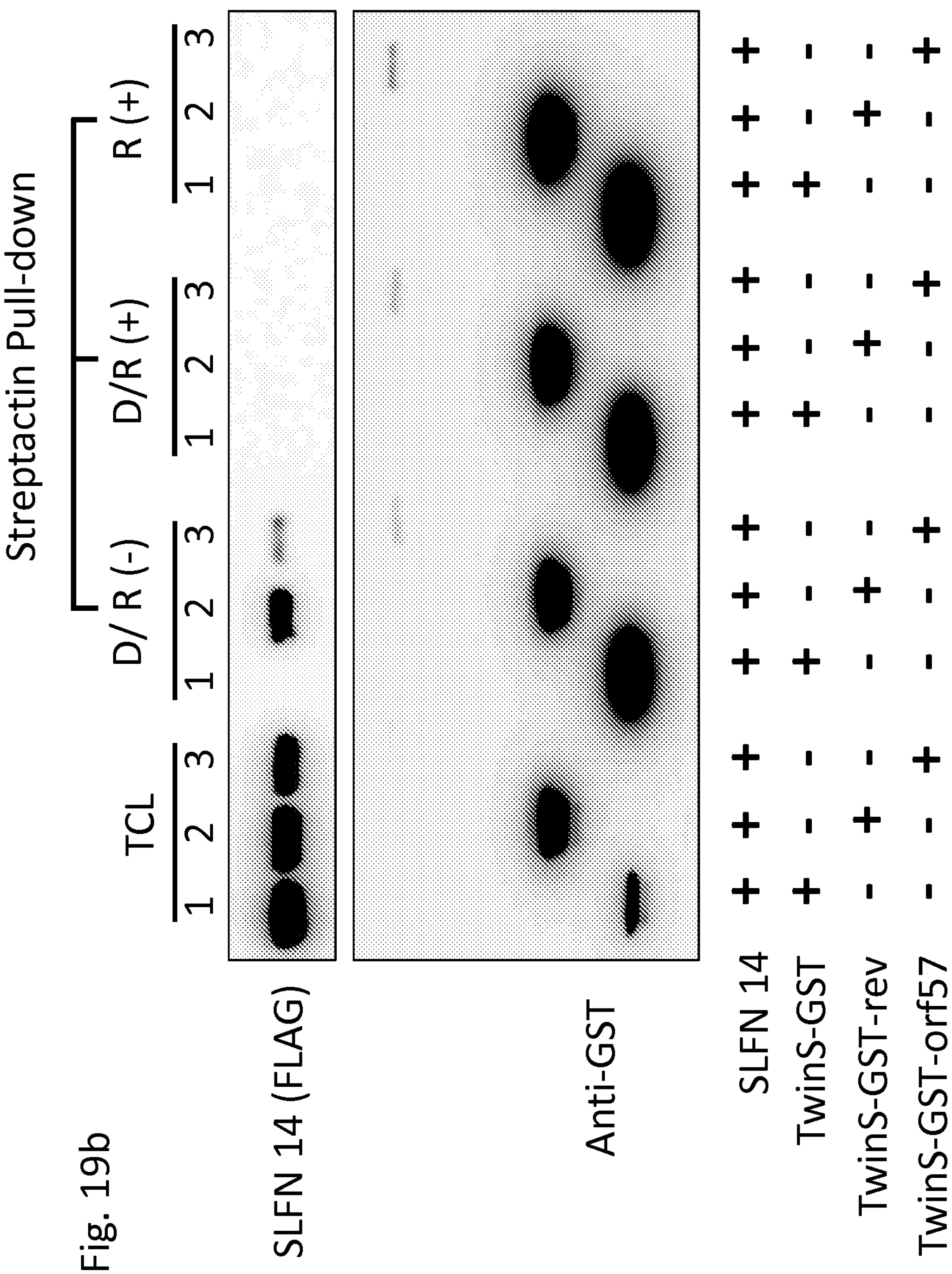

The above results prompted us to investigate the possibility of an interaction between schlafen 14 and each trans-inducer. V5-tagged rev, v5-tagged orf57, or v5-tagged gL (codon-optimized) as control was expressed by transfection and v5-tagged proteins in cell extracts were immunoprecipitated. Schlafen 14 specifically immunoprecipitated with rev and with orf57 but not with the gL negative control (FIG. 19*a*). Twinstrep-tagged GST, GST-rev, or GST-orf57 was co-expressed with schlafen 14 (FIG. 19*b*). The pulled-down fractions of rev and orf57 but not GST contained schlafen 14. However, treatment of RNase A alone or in combination with DNase I, dissociated this interaction, indicating that it was mediated by cellular RNA(s).

The Effect of Rev and Orf57 on their Target RNAs

Figure 22B:
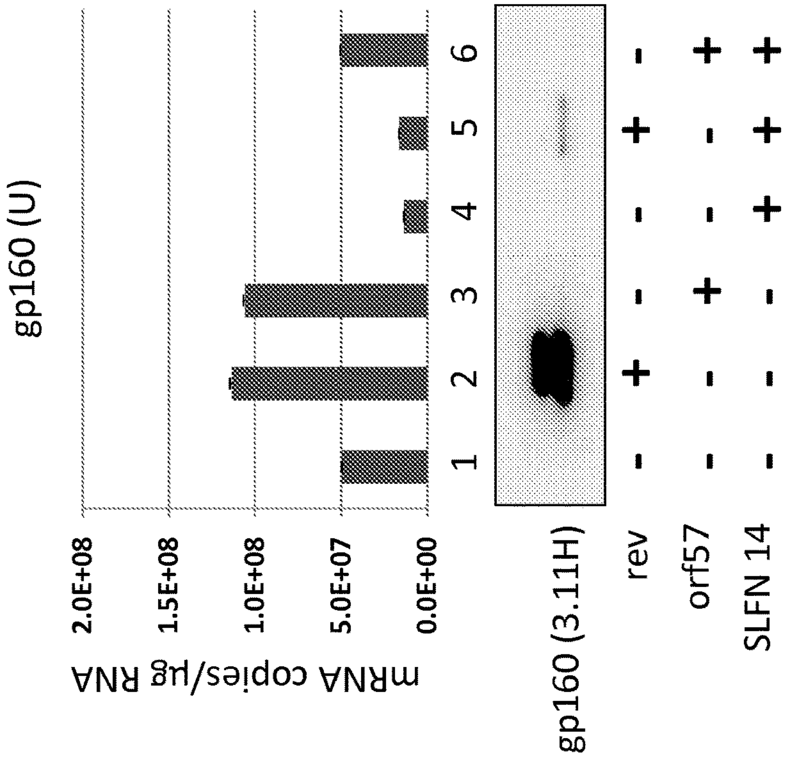
FIG. 22*a*-22*c* shows the effect of rev and orf57 on their target RNA levels. Expression cassette of gp160 with the unmodified (U) or codon-modified (M, gH-like) gp160 sequence, schlafen 14, and orf57, and rev were transfected into 293T cells as indicated. Total cellular RNAs were purified and gp160-specific RNAs were measured (copies/μg RNA) by a real time RT-PCR. Standard deviations from triplicates were indicated with error bars.
Figure 22A:
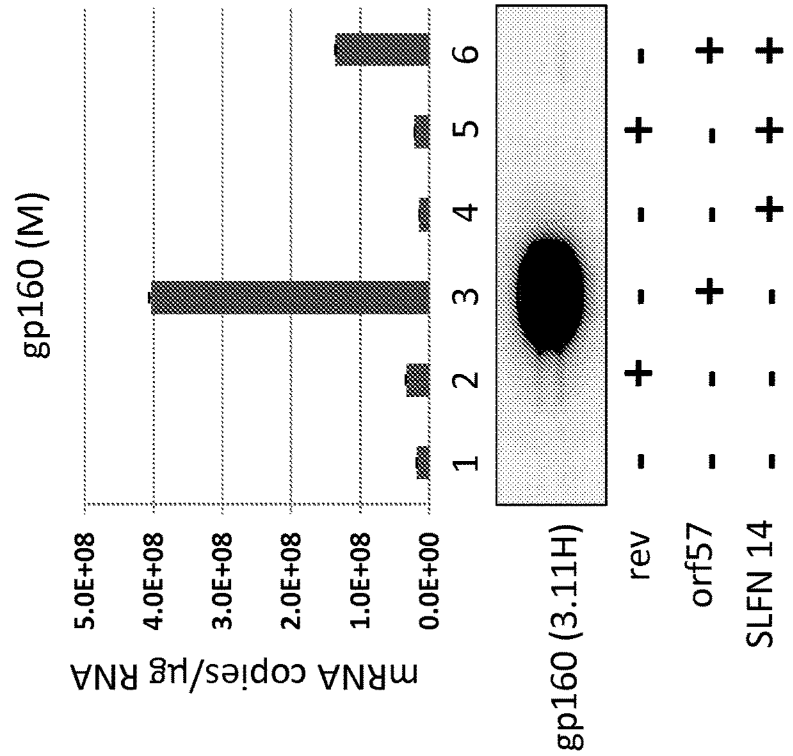
Figure 22C:
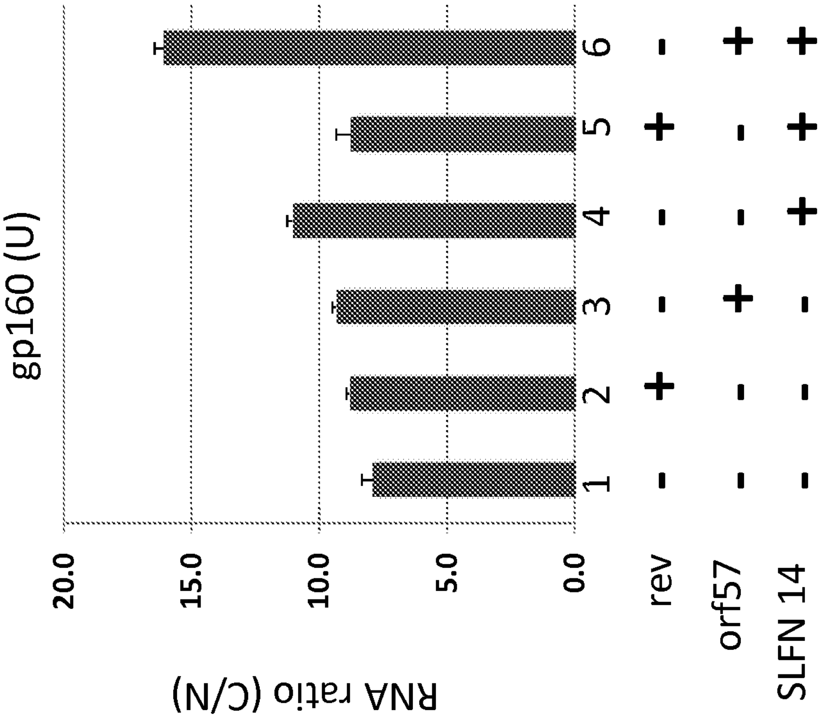

To examine the effects of orf57 and rev on levels of target RNA, transfections were performed in the presence and absence of schlafen 14 (FIG. 22). Schlafen 14 was included to evaluate its restricting activity. Orf57 dramatically increased (about 22-fold) the level of its target RNA, codon-modified (gH-like) SIV gp160 RNA, present in the cell (FIG. 22*a*, lane 1 vs. 3). The levels of gp160 protein derived from the codon-modified (gH-like) cassette were well matched with the RNA levels. Addition of schlafen 14 under these conditions dampened orf57-mediated RNA enhancement (FIG. 22*a*, lane 3 vs. 6). It is noteworthy that schlafen 14 almost completely blocked gp160 protein expression (FIG. 22*a*, lane 6), but the gp160 RNA levels were still markedly higher than control (FIG. 22*a*, lane 1), suggesting that schlafen 14-mediated inhibition is related to post-transcriptional processes.

The effects of rev on its natural target sequence were somewhat different from those of orf57 described above (FIG. 22*b*). The levels of gp160 RNA from the expression cassette with natural codon usage showed only a moderate increase by the co-expression of rev or orf57 (about 2-fold each). However, gp160 protein expression was very effectively rescued only by rev, but not by orf57 (FIG. 22*b*, lanes 2 and 3). Expression of schlafen 14 under these conditions diminished gp160 RNA enhancement and, accordingly, protein expression (FIG. 22*b*, lanes 4-6). Although the levels of gp160 RNA with unmodified sequence in the presence of both rev and schlafen 14 were even lower than control, there was still a detectable level of protein expression as compared to control (FIG. 22*b*, lane 1 vs. lane 5). Taken together, these results suggest that rev-mediated induction is related to post-transcriptional processes in the absence of a significant enhancement of the levels of its target RNA as was observed with orf57-mediated induction. Also, it should be noted from Supplementary FIGS. 22*a* and 2*b* that orf57-mediated enhancement of target RNA levels was dependent on the codon usage of its target sequence since very different degrees of induction (22-fold for a codon-modified (gH-like) gp160 vs. 2-fold for an unmodified SIV gp160) were observed.

To further investigate the action of rev on the expression of unmodified SIV gp160, nuclear vs. cytoplasmic RNAs were separately isolated using the cell pellets that received the same transfections as in Supplementary FIG. 22*b*. The ratio of cytoplasmic/nuclear gp160 RNA was not significantly changed among samples tested (FIG. 22*c*) by rev, suggesting that rev induced, at least in our experimental setting, SIV gp160 protein expression from the expression cassette with natural codon usage via a mechanism independent of nuclear export of its cognate RNA.

Figure 20A:
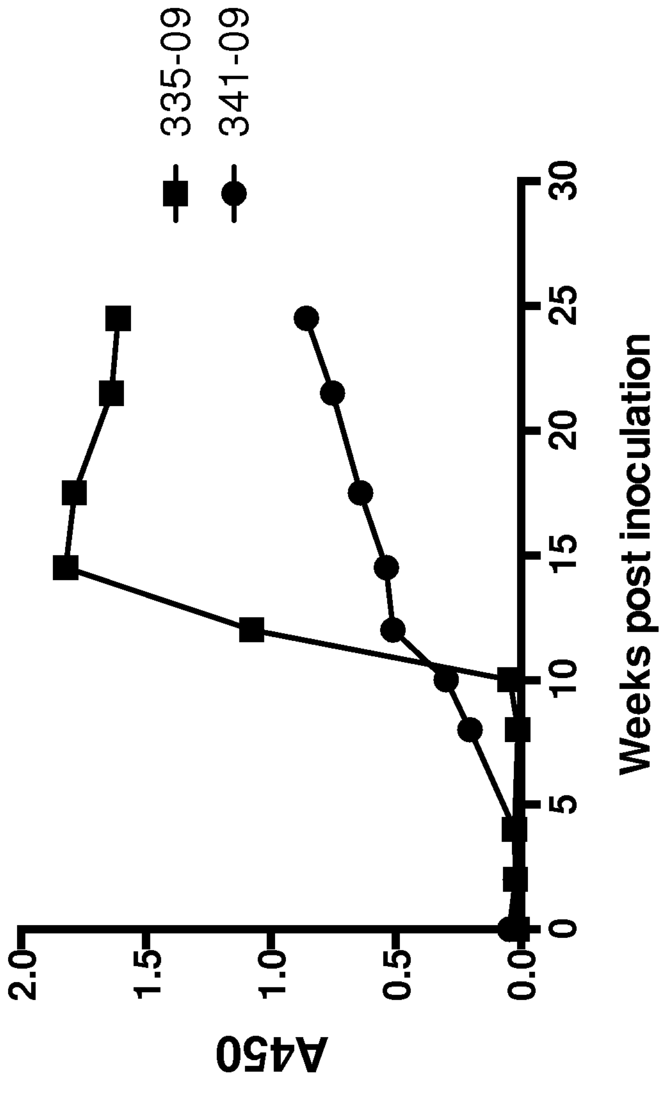
FIG. 20*a*-20*b* shows the elicitation of anti-env antibodies by recombinant RRV with codon-modified gp160 sequence.
Figure 20B:
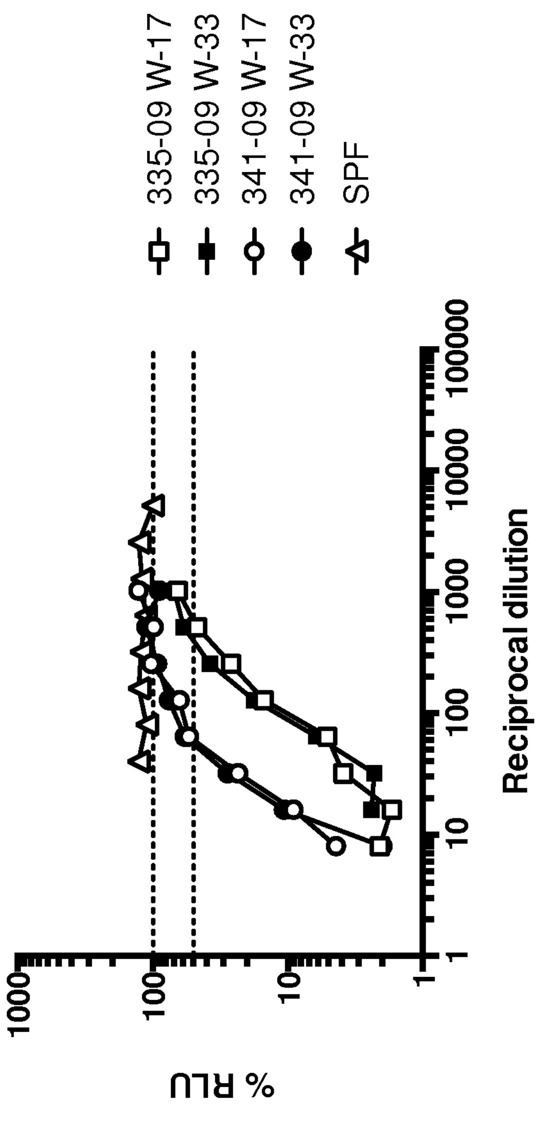
Figure 23:
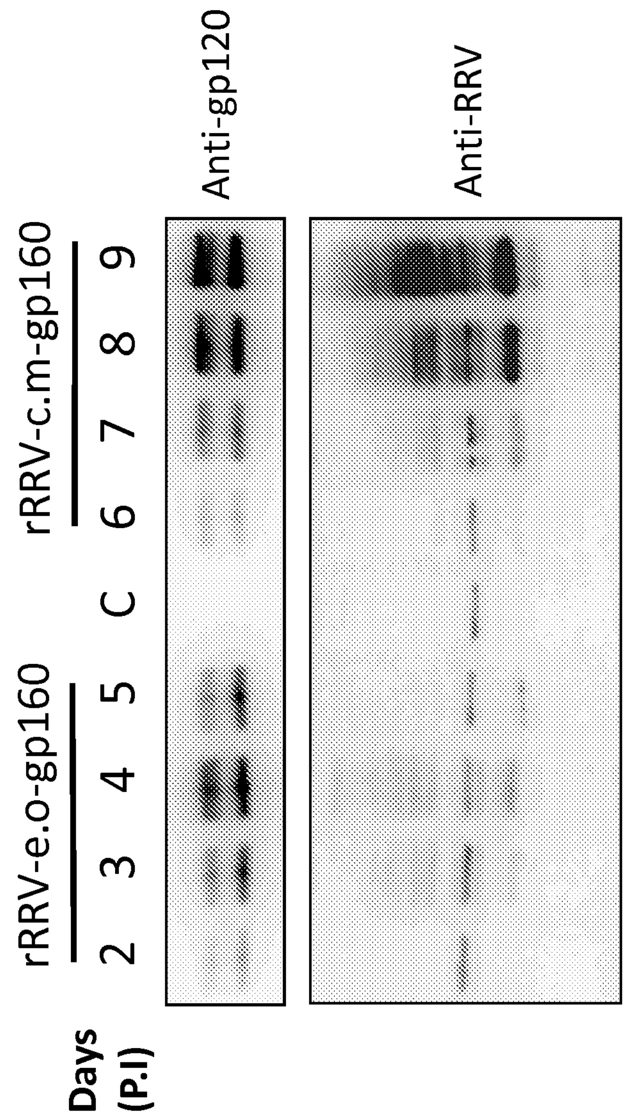
FIG. 23 shows the delayed expression of SIV gp160 by recombinant RRV with codon-modified gp160 sequence. Recombinant RRVs expressing gp160 from expression-optimized (e.o) or codon-modified (c.m) (gH-like) sequence were made and tittered by qPCR. Each well of rhesus fibroblast cells on a 6-well plates was infected with equal amount of each recombinant RRV ($1.0\times10^9$ genome copies) and harvested at the indicated time points. Expression of gp160 and RRV viral proteins was measured using an anti-gp120 (3.11H) antibody and anti-RRV whole sera, respectively. P.I denotes post-infection.

Elicitation of Anti-Env Antibodies by Recombinant RRV with Codon-Modified Gp160 Sequences In previous studies with recombinant RRV that employed the CMV immediate early promoter and a codon-optimized version of gp160 gene sequences, anti-gp160 antibodies were not elicited upon monkey infection[16]. Expression of gp160 from this earlier construct should not be temporally regulated as a late gene product. We thus constructed a recombinant RRV using the codon-modified version of gp160 sequences whose expression should now be temporally regulated as a late gene product. The CMV immediate early promoter was again used for this new recombinant RRV. Consistent with expectation, gp160 protein synthesis in fibroblasts infected with the new recombinant RRV appeared late, coincident with the major RRV proteins (FIG. 23). Now, for the first time, upon experimental infection of rhesus monkeys, anti-gp160 antibody responses were readily measured (FIG. 20*a*). These antibodies have persisted for more than one year and were capable of neutralizing SIV316 (FIGS. 20 *a* and *b*) but not SIV239 (data not shown) in vitro. The titers of anti-gp160 antibodies in these animals were considerably lower than those found in SIV infected animals. It should be noted that anti-gp160 antibody responses were also not achieved with a recombinant CMV that employed a codon-optimized version of gp160 sequences[17,18].

Discussion

We have focused our attention on five families of persisting viruses. All five have early→late transitions for expression of structural gene products. Representative structural gene products from all five are derived from RNA transcripts with a markedly skewed, poor codon usage. We have put a strong promoter in front of three of these and this yielded essentially no detectable protein expression under transfection conditions that yielded very strong levels of expression of their codon-optimized versions. These results alone provide suggestive evidence that multiple families of persisting viruses use abnormal codon usage to achieve regulated expression of their late structural gene products.

Our data show that rev induction of Env protein expression depends on the nature of the bad codon usage. Rev inducibility was lost when 10.5% of the codons were replaced with synonymous codons reflecting the codon usage of RRV gH. While it had been previously known that rev induction depended on the rev response element (the RRE) and the presence of a splice donor upstream of the coding sequence[11,19], the dependence on the nature of the bad codon usage had not been previously known. Similarly, our data show that orf57 induction of RRV gH protein expression also depends on the nature of the bad codon usage. Orf57 inducibility was lost when 14.3% of the codons were replaced with synonymous codons reflecting the codon usage of SIV gp160. Again, this dependence of orf57-inducing activity on the nature of the bad codon usage had not been previously known. Remarkably, rev dependence of gp160 expression can be flipped to orf57 dependence simply by changing the nature of the codon usage; similarly, orf57 dependence of RRV gH expression can be flipped to rev dependence simply by changing the nature of the codon usage. It is important to note that no complicated algorithms have been used, at least to date, to select the codon biases that have resulted in this remarkable flip in dependencies. It will be interesting for future experiments to sort out which codons or which locations are most important for the effect.

Our data further suggest that the restricted expression of the parental env and gH sequences is intimately tied to the schlafen family of cellular proteins. Rev- and orf57-dependent expression was inhibited by schlafen 14 in a dose-dependent fashion and schlafen 14-mediated inhibition could be overcome by rev or by orf57 depending on the target RNA, again in a dose dependent fashion. Furthermore, rev and schlafen 14 could be co-immunoprecipitated, but the interaction did not appear to be direct since it was abrogated by RNase A digestion. It is noteworthy in the context of HIV/SIV replication that the viral proteins whose expression is inhibited by schlafen 11 (gag, rt, vif, vpu, and vpr) are expressed from RNAs that contain the RRE[15]. Thus, a main role of rev could be to rescue expression of HIV/SIV proteins inhibited by cellular schlafens.

While our data unambiguously make the case for the importance of the nature of aberrantly skewed codon usage for the specificity of trans-induction across multiple families of enveloped viruses, it should by no means be assumed that this is the only mechanism for regulating late structural gene expression or that the specific mechanisms of codon usage dependence is the same across multiple families. Indeed, while the early literature emphasized the effects of rev in regulating the egress of unspliced and minimally spliced RNAs out of the nucleus[19,20], recent literature has emphasized the effects of rev on expression of RNA in the cytoplasm[21,22] and on other regulatory effects[23-25]. The literature is similarly diverse for the post-transcriptional effects of orf57 of gamma-2 herpesviruses with respect to RNA egress, RNA stability, and translation[8,26-29]. At least under the assay conditions employed in our transfection experiments shown in supplementary FIG. 17, orf57 specifically enhanced the accumulation of target RNA in the cytoplasm, while rev specifically increased the ability of target RNAs to be translated. The enhancement of target RNA levels by orf57 is consistent with a previous publication from our laboratory[8] and with published work by others[26,30]. What exactly is being recognized to achieve the codon usage-dependent trans-induction is a fascinating question. While one could speculate on RNA secondary structure, it is difficult to imagine how the distributed codon changes could result in specific RNA secondary structures that could be responsible for the ability to flip rev vs. orf57 trans-induction.

What advantage might temporal regulation of expression of structural proteins provide to these five families of persisting viruses? Perhaps in the face of persisting immune responses, these viruses need to make as much of these essential virion proteins in as short a time frame as possible in order to get infectious virus out of the cell before destruction. Even more fascinating is the evolution of abnormal codon usage as a means for achieving this temporal regulation. If schlafens indeed are key restricting elements in this story, one can easily envision an evolutionary battle: codon usage and trans-induction as the armament on the virus' side, with schlafens trying to keep up on the host side.

Our observations on the influence of codon usage have practical utility for the use of persisting viruses as vaccine vectors or vectors for gene therapy. The altered codon usage in our recombinant RRV-SIVenv has allowed us for the first time to achieve anti-gp160 antibody responses with this herpesvirus vector system.

Methods Summary

Codon usage was analyzed using the graphical codon usage analyser (GCUA) software[31] and MacVector program. Codon-modified SIVgp160, RRV gH, firefly luciferase, and codon-optimized SV40 VP1 sequences were synthesized in vitro (GenScript) and cloned in pcDNA6-v5 HisA. HEK293T/17 cells were maintained in Dulbecco's modified Eagle medium (DMEM) supplemented with 10% fetal calf serum (FCS) and transfected using a jetPRIME transfection reagent (Polyplus transfection) according to the manufacturer's suggestion. Recombinant RRV harboring codon-modified SIV gp160 sequence was generated by the method described earlier[16,32] and titrated using a real-time qPCR assay. Expression of gp160 was verified in vitro by infecting rhesus fibroblast cells with recombinant RRV followed by immunoblotting. The levels of anti-env antibodies in animal serum were measured by a enzyme-linked immunosorbent assay (ELISA). Neutralization assays were performed using monkey sera taken at weeks 17 and 33 post-inoculation with rRRV according to methods described previously[33].

Methods

Plasmids.

The cDNA sequences encoding unmodified and codon-modified (gH-like) SIV gp160 were cloned in pcDNA6-v5-hisA plasmid vector (Life Technologies) with the splicing donor sequence (aaacaagtaagt (SEQ ID NO: 6)) in front of the translational start codon of gp160 coding sequence. The cDNA sequences expressing unmodified and codon-modified (gp160-like) RRV gH were cloned in pcDNA6-v5-hisA plasmid vector with or without the splicing donor sequence (ctaatacatcttctgcatcaaacaagtaagt (SEQ ID NO: 5)) and the RRE as indicated in FIG. 16*b*. The cDNA sequences expressing unmodified and codon-modified (gp160-like and gH-like) firefly luciferase were cloned in pcDNA6-v5-hisA plasmid vector with the splicing donor sequence (ctaatacatcttctgcatcaaacaagtaagt (SEQ ID NO: 5)) in front of the translational start codon and the RRE after the stop codon. The RRV orf57 and HIV-1 rev cDNA sequences (from pCMV-HIV-1, NIH AIDS reagent program) were cloned in pEF1-v5-hisA (Life Technologies) and pcDNA6-v5-hisA plasmid vector, respectively. The plasmids expressing human schlafen 5, 11, 12, 13, and 14 were in pcDNA4-FLAG (Life Technologies) and obtained from Dr. Michael David (UCSD). For protein-protein interaction study, cDNA sequences encoding HIV-1 rev or RRV orf57 were cloned in pEBG plasmid vector with a twinstrep tag at the N-terminus. Firefly luciferase sequences with unmodified, gH-like, or gp160-like codon usage were cloned in pcDNA6-v5-hisA plasmid with splicing donor and the RRE at the N-terminus and C-terminus, respectively. The wild type and codon-optimized sequence of SV40 VP1 were cloned in pcDNA6-v5-hisA plasmid.

Cell Culture and Transfection.

HEK293T/17 cells (ATCC) were cultured and maintained in Dulbecco's modified Eagle medium (DMEM, Life Technologies) supplemented with 10% fetal calf serum (FCS, Life Technologies), glutamine, and penicillin-streptomycin. For rhesus fibroblast (RF) cells, 20% of FCS was added. HEK293T/17 cells seeded onto 6-well plates 1 day earlier were transfected, unless it was indicated otherwise, with 2 μg of gp160, 1 μg of rev or orf57, and 0.2 μg schlafen plasmid DNAs using a jetPRIME transfection reagent (Polyplus transfection).

Antibodies and Reagents.

The antibodies and reagents used in this study were obtained from the following sources; mouse and rabbit anti-v5 (Life Technologies), mouse and rabbit anti-FLAG (Sigma), kk41 (NIH AIDS reagent program), anti-GST (sigma), Protein A agarose (Pierce), and strep-tactin agarose (Fisher scientific). Anti-gp120 antibody (3.11H) was purified from hybridoma cell line acquired from Dr. J. E. Robinson. DNase I (2,000 U/ml) and RNase A (10 mg/ml) were purchased from New England Biolabs and Thermo Scientific, respectively.

Immunoblotting, Immunoprecipitation, and Strep-Tactin Pull-Down.

Cells were harvested, resuspended, and lysed with lysis buffer (50 mM Tris-pH 8.0, 150 mM NaCl, 0.5% NP-40) supplemented with protease inhibitor (Roche). The supernatants, after centrifugation (12,000 g for 5 min), were transferred into new tubes and their protein levels were measured using a bicinchoninic acid protein assay kit (Pierce) and normalized. An equal volume of 2×SDS sample buffer (Sigma) was added to each lysate, and then the samples were incubated at 95° C. for 5 min and separated by sodium dodecyl sulfate-polyacrylamide gel electrophoresis (SDS-PAGE). The proteins from the gels were transferred to a polyvinylidene difluoride (PVDF) membrane (Roche) and subjected to immunoblotting. Briefly, the membranes were blocked with phosphate-buffered saline (PBS) containing 5% skim milk for 30 min at room temperature and incubated with the appropriate primary antibody for 2 hours, followed by 1 hour incubation with the appropriate horseradish peroxidase (HRP)-conjugated secondary antibody. Specific signals were detected by an enhanced chemiluminescence system using a SuperSignal West Pico chemiluminescent substrate (Pierce). For immunoprecipitation or streptactin pull-down, the cell lysates above were mixed with the appropriate antibody and incubated with protein A/G agarose or strep-tactin agarose for 2 hours at 4° C. The agarose beads were washed with cold lysis buffer 3 times and subjected to immunoblotting.

RNA Purification and Fractionation.

Cells grown on a 10 cm culture dish were rinsed with PBS and detached using PBS containing 1 mM EDTA. Roughly ⅙ of the cells were subjected to immunoblotting, and the remaining ⅚ of cells were subjected to fractionation. For fractionation, cells were pelleted by low-speed centrifugation (6,000 g, 1 min), and then 1.0 ml of ice-cold cell fractionation buffer (PARIS kit, Ambion) and 3 μl of RNase OUT (Life Technologies) were added to the cell pellets. After incubation of 10 min on ice with gentle mixing, the nuclear pellets and cytoplasmic supernatants were separated by centrifugation for 3 min at 500 g. For the cytoplasmic fraction, 0.3 ml of supernatant was mixed with an equal volume of 2× lysis/binding buffer (PARIS kit), and 0.3 ml of 100% ethanol was added to the mixture. For the nuclear fraction, the nuclear pellet obtained above was lysed with 0.6 ml of RLT buffer (RNeasy Plus miniprep kit, Qiagen) and passed through a QIAshredder and gDNA elimination column (Qiagen). The total RNA from these nuclear and cytoplasmic fractions was purified further using an RNeasy plus miniprep kit according to the manufacturer's instructions.

Real-Time qPCR.

For real-time PCR analysis, HEK293T/17 cells on 6-well plate were transfected with plasmids expressing unmodified or codon-modified (gH-like) gp160 (in pcDNA6-v5 HisA), rev (pCMV-HIV-1), orf57 (pIRES-orf57-FLAG), or human schlafen 14 (pcDNA4-schlafen 14-FLAG). Total RNA or nuclear/cytoplasmic fraction was purified as described above and normalized. Real-time qPCR was performed using a primer set (forward; GCCTATCCCTAACCCTCTCC (SEQ ID NO: 7), reverse; CAGATGGCTGGCAACTAGAA (SEQ ID NO: 8), reporter; FAM-AAACCCGCTGATCAGCCTCGA-NFQ (SEQ ID NO: 9)) and 4× Taqman Fast Virus 1-step Master mix (Life Technologies), and AB 7500 real-time PCR system. The thermo cycle was composed of reverse transcription (50° C., 5 min), inactivation (95° C., 1 min) followed by 40 cycles of amplification (95° C., 15 sec; 60° C., 45 sec). The number of RNA copy was calculated by using a pcDNA6-v5-hisA DNA as a standard.

Luciferase Assay.

Each well of 293T cells on a 48-well plate was transfected with 250 ng of firefly reporter plasmid, 25 ng of pRL-SV *renilla* plasmid (Promega), and 62.5 ng of plasmid encoding trans-inducer (pcDNA6-rev or pEF1-orf57) by using a jetPRIME transfection reagent. At 36 hr after transfection, firefly and *renilla* luciferase activities were measured using the Dual-Luciferase reporter assay reagents (Promega) and the luciferase activity was normalized as the ratio of firefly/*renilla* luciferase values. Standard deviations from triplicates were indicated with error bars.

Generation of Recombinant RRV.

Recombinant RRV expressing SIV env from the codon-modified (gH-like) gp160 sequence was made by overlapping cosmid transfection as described earlier[32] and tittered by real-time qPCR using a primer set specific to the sequence of latency-associated nuclear antigen (LANA) of RRV (Forward; ACCGCCTGTTGCGTGTTA (SEQ ID NO: 10), reverse; CAATCGCCAACGCCTCAA (SEQ ID NO: 11), reporter; FAM-CAGGCCCCATCCCC (SEQ ID NO: 12)). Two rhesus monkeys were inoculated with this recombinant RRV ($9\times10^7$ genome copies/animal) and the levels of anti-env antibodies in their serum were measured for over a year using an enzyme-linked immunosorbent assay.

SIVgp120 ELISA.

Wells of an ELISA plate (Nunc MaxiSorp 468667) were coated overnight with 100 μl of recombinant SIVmac239 gp120 protein (Immune Technology Corp, IT-001-022p) diluted to 1 μg/ml in bicarbonate buffer solution (0.8 g $Na_2CO_3$, 1.47 g $NaHCO_3$, 500 ml deionized water) with a plate cover. Wells were then washed 12 times with deionized water using a Nunc Immuno Washer. Wells were blocked using 300 μl of 5% skim milk in PBS containing 0.05% of Tween-20 (PBS-T) for one hour at 37° C. with a plate cover. The wells were washed 3 times with deionized water. Serum was diluted 1:20 or 1:100 in 5% skim milk in PBS-T and 100 μl was added to the wells, followed by incubation for 1 hour at 37° C. with a plate cover. The wells were then washed 12 times with PBS-T. HRP-conjugated goat anti-monkey secondary antibody (Santa Cruz, sc-2458) was diluted 1:2000 in 5% skim milk in PBS-T and 100 μl was added to each well, and incubated for one hour at 37° C. with a plate cover. The wells were washed 12 times with PBS-T and 100 μl of TMB substrate (Thermo Scientific, 34028) were then added to the wells. The reaction was allowed to develop for 2 minutes, and then 100 μl of phosphoric acid (1M) was added to each well to stop the reaction and then absorbance was measured on a Wallac Victor3 Multilabel Counter (Perkin Elmer, 1420-051) at a wavelength 450 nM.

1 Lukac, D. M., Kirshner, J. R. & Ganem, D. Transcriptional activation by the product of open reading frame 50 of Kaposi's sarcoma-associated herpesvirus is required for lytic viral reactivation in B cells. *Journal of virology* 73, 9348-9361 (1999).
2 Zalani, S., Holley-Guthrie, E. & Kenney, S. Epstein-Barr viral latency is disrupted by the immediate-early BRLF1 protein through a cell-specific mechanism. *Proceedings of the National Academy of Sciences of the United States of America* 93, 9194-9199 (1996).
3 Sun, R. et al. A viral gene that activates lytic cycle expression of Kaposi's sarcoma-associated herpesvirus. *Proceedings of the National Academy of Sciences of the United States of America* 95, 10866-10871 (1998).
4 Kirshner, J. R., Lukac, D. M., Chang, J. & Ganem, D. Kaposi's sarcoma-associated herpesvirus open reading frame 57 encodes a posttranscriptional regulator with multiple distinct activities. *Journal of virology* 74, 3586-3597 (2000).
5 Sandri-Goldin, R. M. & Mendoza, G. E. A herpesvirus regulatory protein appears to act post-transcriptionally by affecting mRNA processing. *Genes & development* 6, 848-863 (1992).
6 Ruvolo, V., Wang, E., Boyle, S. & Swaminathan, S. The Epstein-Ban virus nuclear protein SM is both a post-transcriptional inhibitor and activator of gene expression. *Proceedings of the National Academy of Sciences of the United States of America* 95, 8852-8857 (1998).
7 Bilello, J. P., Morgan, J. S. & Desrosiers, R. C. Extreme dependence of gH and gL expression on ORF57 and association with highly unusual codon usage in rhesus monkey rhadinovirus. *Journal of virology* 82, 7231-7237, doi:10.1128/JVI.00564-08 (2008).
8 Shin, Y. C. & Desrosiers, R. C. Rhesus monkey rhadinovirus ORF57 induces gH and gL glycoprotein expression through posttranscriptional accumulation of target mRNAs. *Journal of virology* 85, 7810-7817, doi:10.1128/JVI.00493-11 (2011).

9 Cochrane, A. W., Chen, C. H. & Rosen, C. A. Specific interaction of the human immunodeficiency virus Rev protein with a structured region in the env mRNA. *Proceedings of the National Academy of Sciences of the United States of America* 87, 1198-1202 (1990).
10 Malim, M. H. et al. HIV-1 structural gene expression requires binding of the Rev trans-activator to its RNA target sequence. *Cell* 60, 675-683 (1990).
11 Chang, D. D. & Sharp, P. A. Regulation by HIV Rev depends upon recognition of splice sites. *Cell* 59, 789-795 (1989).
12 Lu, X. B., Heimer, J., Rekosh, D. & Hammarskjold, M. L. U1 small nuclear RNA plays a direct role in the formation of a rev-regulated human immunodeficiency virus env mRNA that remains unspliced. *Proceedings of the National Academy of Sciences of the United States of America* 87, 7598-7602 (1990).
13 Hammarskjold, M. L. et al. Regulation of human immunodeficiency virus env expression by the rev gene product. *Journal of virology* 63, 1959-1966 (1989).
14 Bustos, O. et al. Evolution of the Schlafen genes, a gene family associated with embryonic lethality, meiotic drive, immune processes and orthopoxvirus virulence. *Gene* 447, 1-11, doi:10.1016/j.gene.2009.07.006 (2009).
15 Li, M. et al. Codon-usage-based inhibition of HIV protein synthesis by human schlafen 11. *Nature* 491, 125-128, doi:10.1038/nature11433 (2012).
16 Bilello, J. P. et al. Vaccine protection against simian immunodeficiency virus in monkeys using recombinant gamma-2 herpesvirus. *Journal of virology* 85, 12708-12720, doi:10.1128/JVI.00865-11 (2011).
17 Hansen, S. G. et al. Effector memory T cell responses are associated with protection of rhesus monkeys from mucosal simian immunodeficiency virus challenge. *Nature medicine* 15, 293-299, doi:10.1038/nm.1935 (2009).
18 Hansen, S. G. et al. Profound early control of highly pathogenic SIV by an effector memory T-cell vaccine. *Nature* 473, 523-527, doi:10.1038/nature10003 (2011).
19 Malim, M. H., Hauber, J., Le, S. Y., Maizel, J. V. & Cullen, B. R. The HIV-1 rev trans-activator acts through a structured target sequence to activate nuclear export of unspliced viral mRNA. *Nature* 338, 254-257, doi:10.1038/338254a0 (1989).
20 Felber, B. K., Hadzopoulou-Cladaras, M., Cladaras, C., Copeland, T. & Pavlakis, G. N. rev protein of human immunodeficiency virus type 1 affects the stability and transport of the viral mRNA. *Proceedings of the National Academy of Sciences of the United States of America* 86, 1495-1499 (1989).
21 D'Agostino, D. M., Felber, B. K., Harrison, J. E. & Pavlakis, G. N. The Rev protein of human immunodeficiency virus type 1 promotes polysomal association and translation of gag/pol and vpu/env mRNAs. *Molecular and cellular biology* 12, 1375-1386 (1992).
22 Perales, C., Carrasco, L. & Gonzalez, M. E. Regulation of HIV-1 env mRNA translation by Rev protein. *Biochimica et biophysica acta* 1743, 169-175, doi:10.1016/j.bbamcr.2004.09.030 (2005).
23 Brandt, S. et al. Rev proteins of human and simian immunodeficiency virus enhance RNA encapsidation. *PLoS pathogens* 3, e54, doi:10.1371/journal.ppat.0030054 (2007).
24 Blissenbach, M., Grewe, B., Hoffmann, B., Brandt, S. & Uberla, K. Nuclear RNA export and packaging functions of HIV-1 Rev revisited. *Journal of virology* 84, 6598-6604, doi:10.1128/JVI.02264-09 (2010).
25 Groom, H. C., Anderson, E. C. & Lever, A. M. Rev: beyond nuclear export. *The Journal of general virology* 90, 1303-1318, doi:10.1099/vir.0.011460-0 (2009).
26 Nekorchuk, M., Han, Z., Hsieh, T. T. & Swaminathan, S. Kaposi's sarcoma-associated herpesvirus ORF57 protein enhances mRNA accumulation independently of effects on nuclear RNA export. *Journal of virology* 81, 9990-9998, doi:10.1128/JVI.00896-07 (2007).
27 Pilkington, G. R. et al. Kaposi's sarcoma-associated herpesvirus ORF57 is not a bona fide export factor. *Journal of virology* 86, 13089-13094, doi:10.1128/JVI.00606-12 (2012).
28 Malik, P., Blackbourn, D. J. & Clements, J. B. The evolutionarily conserved Kaposi's sarcoma-associated herpesvirus ORF57 protein interacts with REF protein and acts as an RNA export factor. *The Journal of biological chemistry* 279, 33001-33011, doi:10.1074/jbc.M313008200 (2004).
29 Williams, B. J. et al. The prototype gamma-2 herpesvirus nucleocytoplasmic shuttling protein, ORF 57, transports viral RNA through the cellular mRNA export pathway. *The Biochemical journal* 387, 295-308, doi:10.1042/BJ20041223 (2005).
30 Sahin, B. B., Patel, D. & Conrad, N. K. Kaposi's sarcoma-associated herpesvirus ORF57 protein binds and protects a nuclear noncoding RNA from cellular RNA decay pathways. *PLoS pathogens* 6, e1000799, doi:10.1371/journal.ppat.1000799 (2010).
31 Fuhrmann, M. et al. Monitoring dynamic expression of nuclear genes in *Chlamydomonas reinhardtii* by using a synthetic luciferase reporter gene. *Plant molecular biology* 55, 869-881, doi:10.1007/s11103-004-2150-6 (2004).
32 Bilello, J. P., Morgan, J. S., Damania, B., Lang, S. M. & Desrosiers, R. C. A genetic system for rhesus monkey rhadinovirus: use of recombinant virus to quantitate antibody-mediated neutralization. *Journal of virology* 80, 1549-1562, doi:10.1128/JVI.80.3.1549-1562.2006 (2006).
33 Martinez-Navio, J. M. & Desrosiers, R. C. Neutralizing capacity of monoclonal antibodies that recognize peptide sequences underlying the carbohydrates on gp41 of simian immunodeficiency virus. *Journal of virology* 86, 12484-12493, doi:10.1128/JVI.01959-12 (2012).

TABLE 3

| SEQ ID | AA/DNA | Description |
|---|---|---|
| 1 | DNA | Wild type gp160 |
| 2 | AA | Wild type gp160 |
| 3 | DNA | SIVgp160 envelope with codon usage signature of RRV gH |
| 4 | AA | SIVgp160 envelope with codon usage signature of RRV gH |

The present inventions has been described more fully hereinabove with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A replication-competent herpesvirus vector system comprising (a) a polynucleotide encoding a trans-inducer polypeptide that enhances expression of a herpesvirus late gene, and (b) a polynucleotide comprising a heterologous recombinant transgene of interest operably linked to a promoter, wherein said heterologous recombinant transgene of interest comprises a codon usage signature of the herpesvirus late gene.

2. The replication-competent herpesvirus vector system of claim 1, wherein said herpesvirus vector system is derived from a Gammaherpes virus.

3. The replication-competent herpesvirus vector system of claim 2, wherein said Gammaherpesvirus is a gamma-2 herpesvirus.

4. The replication-competent herpesvirus vector system of claim 1, wherein said herpesvirus vector system is derived from a herpesvirus of the Betaherpesvirinae subfamily.

5. The replication-competent herpesvirus vector system of claim 1, wherein said herpesvirus vector system is derived from a herpesvirus of the Alphaherpesvirinae subfamily.

6. The replication-competent herpesvirus vector system of claim 1, wherein said heterologous recombinant transgene of interest encodes an antigen.

7. The replication-competent herpesvirus vector system of claim 6, wherein said antigen is a microbial antigen or a tumor-associated antigen.

8. The replication-competent herpesvirus vector system of claim 7, wherein said microbial antigen comprises a viral antigen, a parasitic antigen, a mycobacteria antigen, or a bacterial antigen.

9. The replication-competent herpesvirus vector system of claim 8, wherein said viral antigen comprises a viral antigen from Retroviridae or Flaviviridae.

10. The replication-competent herpesvirus vector system of claim 9, wherein said Retroviridae or Flaviviridae viral antigen comprises a viral antigen from a dengue virus, a lentivirus, a human immunodeficiency virus (HIV) or a simian immunodeficiency virus (SIV).

11. The replication-competent herpesvirus vector system of claim 8, wherein said viral antigen comprises an envelope polypeptide.

12. The replication-competent herpesvirus vector system of claim 11, wherein said envelope polypeptide is from HIV or SIV.

13. The replication-competent herpesvirus vector system of claim 12, wherein said recombinant transgene comprises the polynucleotide set forth in SEQ ID NO: 1 or a polynucleotide having at least 90% sequence identity to SEQ ID NO: I, wherein said polynucleotide provides an improved immune response when compared to a recombinant transgene that encodes the envelope polypeptide from HIV or SIV but that lacks the codon usage signature.

14. The replication-competent herpesvirus vector system of claim 8, wherein said bacterial antigen is from *Mycobacterium tuberculosis.*

15. The replication-competent herpesvirus vector system of claim 7, wherein said microbial antigen is from *Plasmodium.*

16. The replication-competent herpesvirus vector system of claim 7, wherein said tumor-associated antigen (a) is associated with melanoma, lymphoma, leukemia, lung cancer, bladder cancer, colon cancer, breast cancer, prostate cancer, esophageal cancer, liver cancer, pancreatic cancer, ovarian cancer, non-small cell lung cancer, renal cancer, neuroblastoma, colorectal cancer, uterine cancer, acute myelocytic leukemia, sarcoma, brain cancer or bone cancer or (b) comprises BAGE, GAGE, MAGE, NY-ESO-1, SSX, gp100, Melan-A/Mart-1, Tyrosinase, PSA, CEA, Mammaglobin-A, p53, HER-2/neu, livin, survivin, B-catenin-m, B-Actin/4/m, Myosin/m, HSP70-2/m, HLA-A2-R170J, GM2, GD2, GD3, MUC-1, sTn, globo-H, WT1, PR1, E75, ras, AFP, URLC10, VEGFR1 and 2, mutant p53, NY-ESO-1, HPV16 E7, B-catenin, CDK4, CDC27, a actinin-4, TRPI/gp75, TRP2, gangliosides, PSMA, HER2, WT1, EphA3, EGFR, CD20, telomerase, MART-1, or an antigenic portion thereof.

17. A host cell or cell line comprising the replication-competent herpesvirus vector system of claim 1.

18. A replication-competent herpesvirus vector particle comprising within its genome a polynucleotide comprising a sequence encoding a trans-inducer polypeptide that enhances expression of a herpesvirus late gene and a heterologous recombinant transgene of interest operably linked to a promoter, wherein said heterologous recombinant transgene comprises a codon usage signature of the herpesvirus late gene.

19. The replication-competent herpesvirus vector particle of claim 18, wherein said herpesvirus particle is derived from a Gammaherpes virus.

20. The replication-competent herpesvirus vector particle of claim 19, wherein said Gammaherpes virus is a gamma-2 herpesvirus.

21. The replication-competent herpesvirus vector particle of claim 18, wherein said herpesvirus particle is derived from a herpesvirus of the Betaherpesvirinae subfamily.

22. The replication-competent herpesvirus vector particle of claim 18, wherein said herpesvirus particle is derived from a herpesvirus of the Alphaherpesvirinae subfamily.

23. The replication-competent herpesvirus vector particle of claim 18, wherein said heterologous recombinant transgene of interest encodes an antigen.

24. The replication-competent herpesvirus vector particle of claim 23, wherein said antigen is a microbial antigen or a tumor-associated antigen.

25. The replication-competent herpesvirus vector particle of claim 24, wherein said microbial antigen comprises a viral antigen, a parasitic antigen, a mycobacteria antigen or a bacterial antigen.

26. A pharmaceutical composition comprising the replication-competent herpesvirus vector particle of claim 18.

27. A method for delivering a transgene of interest to a cell comprising contacting the cell with a replication-competent herpesvirus vector particle of claim 18.

28. A method of generating an immune response against a microbial antigen in a subject in need thereof comprising administering to said subject a therapeutically effective amount of the replication competent herpesvirus vector particle of claim 18, wherein the heterologous recombinant transgene encodes the microbial antigen, and wherein an immune response against said microbial antigen is generated in said subject.

29. A method for treating or inhibiting a microbial infection or cancer in a subject in need thereof comprising administering to said subject a therapeutically effective amount of the replication-competent herpesvirus vector particle of claim 18, wherein the heterologous recombinant transgene encodes a microbial antigen or a tumor-associated antigen, and wherein an immune response against said microbial antigen or tumor-associated antibody is generated in said subject and thereby treats or inhibits said microbial infection or cancer.

30. The replication-competent herpesvirus vector system of claim 1, wherein the herpesvirus late gene comprises a polynucleotide encoding a capsid protein, a tegument protein, or an envelope protein.

31. The replication-competent herpesvirus vector system of claim 1, wherein the herpesvirus late gene comprises a polynucleotide encoding a glycoprotein.

32. The replication-competent herpesvirus vector system of claim 31, wherein the glycoprotein is selected from the group consisting of glycoprotein B (gB), glycoprotein C (gC), glycoprotein D (gD), glycoprotein H (gH), and glycoprotein L (gL).

33. The replication-competent herpesvirus vector system of claim 1, wherein the trans-inducer polypeptide is ORF57.

34. A method of increasing expression of a transgene by a host cell, comprising (a) altering codons of the transgene to reflect the codon usage signature of a herpesvirus late gene, (b) inserting the transgene with the altered codons into a replication-competent herpesvirus vector, (c) introducing into the host cell the replication-competent herpesvirus vector, and (d) culturing the host cell comprising the replication-competent herpesvirus vector in the presence of a herpesvirus trans-inducer polypeptide that enhances expression of the herpesvirus late gene.

35. The method of claim 34, wherein the replication-competent herpesvirus vector is derived from a Gammaherpes virus, a Betaherpes virus, or an Alphaherpes virus.

36. The method of claim 34, wherein the herpesvirus late gene comprises a polynucleotide encoding a capsid protein, a tegument protein, or an envelope protein.

37. The method of claim 34, wherein the herpesvirus late gene comprises a polynucleotide encoding a glycoprotein.

38. The method of claim 37, wherein the glycoprotein is selected from the group consisting of glycoprotein B (gB), glycoprotein C (gC), glycoprotein D (gD), glycoprotein H (gH), and glycoprotein L (gL).

39. The method of claim 38, wherein the trans-inducer polypeptide is ORF57.

40. The method of claim 34, comprising altering codons of the transgene to codons that are present at high frequency in the coding sequence of the herpesvirus late gene.

41. The method of claim 34, wherein the altered codons are codons that are present at high frequency in the coding sequence of the herpesvirus late gene.

42. The replication-competent herpesvirus vector system of claim 1, wherein said heterologous recombinant transgene of interest comprises codons used at high frequency in the coding sequence of the herpesvirus late gene.

43. The replication-competent herpesvirus vector system of claim 1, wherein said heterologous recombinant transgene of interest has been modified to comprise one or more codons present at high frequency in the coding sequence of the herpesvirus late gene.

* * * * *

SEQUENCE LISTING

```
<160> NUMBER OF SEQ ID NOS: 12

<210> SEQ ID NO 1
<211> LENGTH: 2640
<212> TYPE: DNA
<213> ORGANISM: Simian immunodeficiency virus

<400> SEQUENCE: 1

atgggatgtc ttgggaatca gctgcttatc gccatcttgc ttttaagtgt ctatgggatc      60

tattgtactc tatatgtcac agtcttttat ggtgtaccag cttggaggaa tgcgacaatt     120

cccctctttt gtgcaaccaa gaatagggat acttggggaa caactcagtg cctaccagat     180

aatggtgatt attcagaagt ggcccttaat gttacagaaa gctttgatgc ctggaataat     240

acagtcacag aacaggcaat agaggatgta tggcaactct ttgagacctc aataaagcct     300

tgtgtaaaat tatccccatt atgcattact atgagatgca ataaaagtga gacagataga     360

tggggattga caaaatcaat aacaacaaca gcatcaacaa catcaacgac agcatcagca     420

aaagtagaca tggtcaatga gactagttct tgtatagccc aggataattg cacaggcttg     480

gaacaagagc aaatgataag ctgtaaattc aacatgacag ggttaaaaag agacaagaaa     540

aaagagtaca atgaaacttg gtactctgca gatttggtat gtgaacaagg gaataacact     600

ggtaatgaaa gtagatgtta catgaaccac tgtaacactt ctgttatcca agagtcttgt     660

gacaaacatt attgggatgc tattagattt aggtattgtg cacctccagg ttatgctttg     720

cttagatgta atgacacaaa ttattcaggc tttatgccta aatgttctaa ggtggtggtc     780

tcttcatgca caaggatgat ggagacacag acttctactt ggtttggctt taatggaact     840

agagcagaaa atagaactta tatttactgg catggtaggg ataataggac tataattagt     900

ttaaataagt attataatct aacaatgaaa tgtagaagac caggaaataa gacagtttta     960

ccagtcacca ttatgtctgg attggttttc cactcacaac caatcaatga taggccaaag    1020

caggcatggt gttggtttgg aggaaaatgg aaggatgcaa taaaagaggt gaagcagacc    1080

attgtcaaac atcccaggta tactggaact aacaatactg ataaaatcaa tttgacggct    1140

cctggaggag gagatccgga agttaccttc atgtggacaa attgcagagg agagttcctc    1200

tactgtaaaa tgaattggtt tctaaattgg gtagaagata ggaatacagc taaccagaag    1260

ccaaaggaac agcataaaag gaattacgtg ccatgtcata ttagacaaat aatcaacact    1320

tggcataaag taggcaaaaa tgtttatttg cctccaagag agggagacct cacgtgtaac    1380

tccacagtga ccagtctcat agcaaacata gattggattg atggaaacca aactaatatc    1440

accatgagtg cagaggtggc agaactgtat cgattggaat tgggagatta taaattagta    1500

gagatcactc caattggctt ggcccccaca gatgtgaaga ggtacactac tggtggcacc    1560

tcaagaaata aaagaggggt ctttgtgcta gggttcttgg gtttctcgc  aacggcaggt    1620

tctgcaatgg gcgcggcgtc gttgacgctg accgctcagt cccgaacttt attggctggg    1680

atagtgcagc aacagcaaca gctgttggac gtggtcaaga gacaacaaga attgttgcga    1740

ctgaccgtct ggggaacaaa gaacctccag actagggtca ctgccatcga gaagtactta    1800
```

-continued

```
aaggaccagg cgcagctgaa tgcttgggga tgtgcgttta gacaagtctg ccacactact   1860

gtaccatggc caaatgcaag tctaacacca aagtggaaca atgagacttg gcaagagtgg   1920

gagcgaaagg ttgacttctt ggaagaaaat ataacagccc tcctagagga ggcacaaatt   1980

caacaagaga agaacatgta tgaattacaa aagttgaata gctgggatgt gtttggcaat   2040

tggtttgacc ttgcttcttg gataaagtat atacaatatg gagtttatat agttgtagga   2100

gtaatactgt taagaatagt gatctatata gtacaaatgc tagctaagtt aaggcagggg   2160

tataggccag tgttctcttc cccaccctct tatttccagc agacccatat ccaacaggac   2220

ccggcactgc caaccagaga aggcaaagaa agagacggtg gagaaggcgg tggcaacagc   2280

tcctggcctt ggcagataga atatattcat ttcctgatcc gccaactgat acgcctcttg   2340

acttggctat tcagcaactg cagaaccttg ctatcgagag tataccagat cctccaacca   2400

atactccaga ggctctctgc gaccctacag aggattcgag aagtcctcag gactgaactg   2460

acctacctac aatatgggtg gagctatttc catgaggcgg tccaggccgt ctggagatct   2520

gcgacagaga ctcttgcggg cgcgtgggga gacttatggg agactcttag gagaggtgga   2580

agatggatac tcgcaatccc caggaggatt agacaagggc ttgagctcac tctcttgtga   2640
```

<210> SEQ ID NO 2
<211> LENGTH: 879
<212> TYPE: PRT
<213> ORGANISM: Simian immunodeficiency virus

<400> SEQUENCE: 2

```
Met Gly Cys Leu Gly Asn Gln Leu Leu Ile Ala Ile Leu Leu Leu Ser
1               5                   10                  15

Val Tyr Gly Ile Tyr Cys Thr Leu Tyr Val Thr Val Phe Tyr Gly Val
            20                  25                  30

Pro Ala Trp Arg Asn Ala Thr Ile Pro Leu Phe Cys Ala Thr Lys Asn
        35                  40                  45

Arg Asp Thr Trp Gly Thr Thr Gln Cys Leu Pro Asp Asn Gly Asp Tyr
    50                  55                  60

Ser Glu Val Ala Leu Asn Val Thr Glu Ser Phe Asp Ala Trp Asn Asn
65                  70                  75                  80

Thr Val Thr Glu Gln Ala Ile Glu Asp Val Trp Gln Leu Phe Glu Thr
                85                  90                  95

Ser Ile Lys Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ile Thr
        115                 120                 125

Thr Thr Ala Ser Thr Thr Ser Thr Thr Ala Ser Ala Lys Val Asp Met
    130                 135                 140

Val Asn Glu Thr Ser Ser Cys Ile Ala Gln Asp Asn Cys Thr Gly Leu
145                 150                 155                 160

Glu Gln Glu Gln Met Ile Ser Cys Lys Phe Asn Met Thr Gly Leu Lys
                165                 170                 175

Arg Asp Lys Lys Lys Glu Tyr Asn Glu Thr Trp Tyr Ser Ala Asp Leu
            180                 185                 190

Val Cys Glu Gln Gly Asn Asn Thr Gly Asn Glu Ser Arg Cys Tyr Met
        195                 200                 205

Asn His Cys Asn Thr Ser Val Ile Gln Glu Ser Cys Asp Lys His Tyr
    210                 215                 220
```

-continued

```
Trp Asp Ala Ile Arg Phe Arg Tyr Cys Ala Pro Pro Gly Tyr Ala Leu
225                 230                 235                 240

Leu Arg Cys Asn Asp Thr Asn Tyr Ser Gly Phe Met Pro Lys Cys Ser
                245                 250                 255

Lys Val Val Val Ser Ser Cys Thr Arg Met Met Glu Thr Gln Thr Ser
            260                 265                 270

Thr Trp Phe Gly Phe Asn Gly Thr Arg Ala Glu Asn Arg Thr Tyr Ile
        275                 280                 285

Tyr Trp His Gly Arg Asp Asn Arg Thr Ile Ile Ser Leu Asn Lys Tyr
    290                 295                 300

Tyr Asn Leu Thr Met Lys Cys Arg Arg Pro Gly Asn Lys Thr Val Leu
305                 310                 315                 320

Pro Val Thr Ile Met Ser Gly Leu Val Phe His Ser Gln Pro Ile Asn
                325                 330                 335

Asp Arg Pro Lys Gln Ala Trp Cys Trp Phe Gly Gly Lys Trp Lys Asp
            340                 345                 350

Ala Ile Lys Glu Val Lys Gln Thr Ile Val Lys His Pro Arg Tyr Thr
        355                 360                 365

Gly Thr Asn Asn Thr Asp Lys Ile Asn Leu Thr Ala Pro Gly Gly Gly
    370                 375                 380

Asp Pro Glu Val Thr Phe Met Trp Thr Asn Cys Arg Gly Glu Phe Leu
385                 390                 395                 400

Tyr Cys Lys Met Asn Trp Phe Leu Asn Trp Val Glu Asp Arg Asn Thr
                405                 410                 415

Ala Asn Gln Lys Pro Lys Glu Gln His Lys Arg Asn Tyr Val Pro Cys
            420                 425                 430

His Ile Arg Gln Ile Ile Asn Thr Trp His Lys Val Gly Lys Asn Val
        435                 440                 445

Tyr Leu Pro Pro Arg Glu Gly Asp Leu Thr Cys Asn Ser Thr Val Thr
    450                 455                 460

Ser Leu Ile Ala Asn Ile Asp Trp Ile Asp Gly Asn Gln Thr Asn Ile
465                 470                 475                 480

Thr Met Ser Ala Glu Val Ala Glu Leu Tyr Arg Leu Glu Leu Gly Asp
                485                 490                 495

Tyr Lys Leu Val Glu Ile Thr Pro Ile Gly Leu Ala Pro Thr Asp Val
            500                 505                 510

Lys Arg Tyr Thr Thr Gly Gly Thr Ser Arg Asn Lys Arg Gly Val Phe
        515                 520                 525

Val Leu Gly Phe Leu Gly Phe Leu Ala Thr Ala Gly Ser Ala Met Gly
    530                 535                 540

Ala Ala Ser Leu Thr Leu Thr Ala Gln Ser Arg Thr Leu Leu Ala Gly
545                 550                 555                 560

Ile Val Gln Gln Gln Gln Gln Leu Leu Asp Val Val Lys Arg Gln Gln
                565                 570                 575

Glu Leu Leu Arg Leu Thr Val Trp Gly Thr Lys Asn Leu Gln Thr Arg
            580                 585                 590

Val Thr Ala Ile Glu Lys Tyr Leu Lys Asp Gln Ala Gln Leu Asn Ala
        595                 600                 605

Trp Gly Cys Ala Phe Arg Gln Val Cys His Thr Thr Val Pro Trp Pro
    610                 615                 620

Asn Ala Ser Leu Thr Pro Lys Trp Asn Asn Glu Thr Trp Gln Glu Trp
625                 630                 635                 640

Glu Arg Lys Val Asp Phe Leu Glu Glu Asn Ile Thr Ala Leu Leu Glu
```

-continued

```
                645                 650                 655

Glu Ala Gln Ile Gln Gln Glu Lys Asn Met Tyr Glu Leu Gln Lys Leu
            660                 665                 670

Asn Ser Trp Asp Val Phe Gly Asn Trp Phe Asp Leu Ala Ser Trp Ile
        675                 680                 685

Lys Tyr Ile Gln Tyr Gly Val Tyr Ile Val Val Gly Val Ile Leu Leu
    690                 695                 700

Arg Ile Val Ile Tyr Ile Val Gln Met Leu Ala Lys Leu Arg Gln Gly
705                 710                 715                 720

Tyr Arg Pro Val Phe Ser Ser Pro Pro Ser Tyr Phe Gln Gln Thr His
                725                 730                 735

Ile Gln Gln Asp Pro Ala Leu Pro Thr Arg Glu Gly Lys Glu Arg Asp
            740                 745                 750

Gly Gly Glu Gly Gly Gly Asn Ser Ser Trp Pro Trp Gln Ile Glu Tyr
        755                 760                 765

Ile His Phe Leu Ile Arg Gln Leu Ile Arg Leu Leu Thr Trp Leu Phe
    770                 775                 780

Ser Asn Cys Arg Thr Leu Leu Ser Arg Val Tyr Gln Ile Leu Gln Pro
785                 790                 795                 800

Ile Leu Gln Arg Leu Ser Ala Thr Leu Gln Arg Ile Arg Glu Val Leu
                805                 810                 815

Arg Thr Glu Leu Thr Tyr Leu Gln Tyr Gly Trp Ser Tyr Phe His Glu
            820                 825                 830

Ala Val Gln Ala Val Trp Arg Ser Ala Thr Glu Thr Leu Ala Gly Ala
        835                 840                 845

Trp Gly Asp Leu Trp Glu Thr Leu Arg Arg Gly Gly Arg Trp Ile Leu
    850                 855                 860

Ala Ile Pro Arg Arg Ile Arg Gln Gly Leu Glu Leu Thr Leu Leu
865                 870                 875
```

<210> SEQ ID NO 3
<211> LENGTH: 2640
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atgggatgtc ttggaaatca gctgcttatc gccatcttgc ttttaagtgt ctatggaatc     60

tattgtacgc tatatgtcac agtcttttat ggtgtaccag cttggcgtaa tgcgacaatt    120

cccttatttt gtgcaaccaa gaatcgtgat acgtggggaa caacgcagtg cctaccagat    180

aatggtgatt attcagaagt ggcccttaat gttacagaaa gctttgatgc ctggaataat    240

acagtcacag aacaggcaat agaagatgta tggcaattat ttgaaacctc aataaagccg    300

tgtgtaaaat tatccccatt atgcattacg atgagatgca ataaaagtga aacagataga    360

tggggattga caaaatcaat aacaacaaca gcatcaacaa catcaacgac agcatcagca    420

aaagtagaca tggtcaatga aacgagttct tgtatagccc aggataattg cacaggcttg    480

gaacaagaac aaatgataag ctgtaaattc aacatgacag gattaaaaag agacaagaaa    540

aaagaataca atgaaacgtg gtactctgca gatttggtat gtgaacaagg aaataacacg    600

ggtaatgaaa gtagatgtta catgaaccac tgtaacacgt ctgttatcca agaatcttgt    660

gacaaacatt attgggatgc tattagattt cgttattgtg caccgccagg ttatgctttg    720
```

-continued

```
cttagatgta atgacacaaa ttattcaggc tttatgccga aatgttctaa ggtggtggtc    780

tcttcatgca cacgtatgat ggaaacacag acgtctacgt ggtttggctt taatggaacg    840

agagcagaaa atagaacgta tatttactgg catggtcgtg ataatcgtac gataattagt    900

ttaaataagt attataatct aacaatgaaa tgtagaagac caggaaataa gacagtttta    960

ccagtcacca ttatgtctgg attggttttc cactcacaac caatcaatga tcgtccaaag   1020

caggcatggt gttggtttgg aggaaaatgg aaggatgcaa taaaagaagt gaagcagacc   1080

attgtcaaac atccccgtta tacgggaacg aacaatacgg ataaaatcaa tttgacggct   1140

ccgggaggag gagatccgga agttaccttc atgtggacaa attgcagagg agaattctta   1200

tactgtaaaa tgaattggtt tctaaattgg gtagaagatc gtaatacagc taaccagaag   1260

ccaaaggaac agcataaacg taattacgtg ccatgtcata ttagacaaat aatcaacacg   1320

tggcataaag taggcaaaaa tgtttatttg ccgccaagag aaggagactt aacgtgtaac   1380

tccacagtga ccagtttaat agcaaacata gattggattg atggaaacca aacgaatatc   1440

accatgagtg cagaagtggc agaactgtat cgattggaat tgggagatta taaattagta   1500

gaaatcacgc caattggctt ggcccccaca gatgtgaaga ggtacactac tggtggcacc   1560

tcaagaaata aaagaggggt ctttgtgcta gggttcttgg gtttctcgc aacggcaggt    1620

tctgcaatgg gcgcggcgtc gttgacgctg accgctcagt cccgaacttt attggctggg   1680

atagtgcagc aacagcaaca gctgttggac gtggtcaaga gacaacaaga attgttgcga   1740

ctgaccgtct ggggaacaaa gaacctccag actagggtca ctgccatcga gaagtactta   1800

aaggaccagg cgcagctgaa tgcttgggga tgtgcgttta gacaagtctg ccacactact   1860

gtaccatggc caaatgcaag tctaacacca aagtggaaca atgaaacgtg gcaagaatgg   1920

gaacgaaagg ttgacttctt ggaagaaaat ataacagcct tactagaaga agcacaaatt   1980

caacaagaaa agaacatgta tgaattacaa aagttgaata gctgggatgt gtttggcaat   2040

tggtttgacc ttgcttcttg gataaagtat atacaatatg gagtttatat agttgtagga   2100

gtaatactgt taagaatagt gatctatata gtacaaatgc tagctaagtt acgtcaggga   2160

tatcgtccag tgttctcttc cccaccctct tatttccagc agacccatat ccaacaggac   2220

ccggcactgc caaccagaga aggcaaagaa agagacggtg gagaaggcgg tggcaacagc   2280

tcctggccgt ggcagataga atatattcat ttcctgatcc gccaactgat acgcttattg   2340

acgtggctat tcagcaactg cagaaccttg ctatcgagag tataccagat cttacaacca   2400

atattacagc gtttatctgc gaccctacag cgtattcgag aagtcttacg tacggaactg   2460

acctacctac aatatggatg gagctatttc catgaagcgg tccaggccgt ctggagatct   2520

gcgacagaaa cgcttgcggg cgcgtgggga gacttatggg aaacgcttcg tagaggtgga   2580

agatggatat tagcaatccc ccgtcgtatt agacaaggac ttgaattaac gttattgtga   2640
```

<210> SEQ ID NO 4
<211> LENGTH: 879
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Gly Cys Leu Gly Asn Gln Leu Leu Ile Ala Ile Leu Leu Leu Ser
1               5                   10                  15

Val Tyr Gly Ile Tyr Cys Thr Leu Tyr Val Thr Val Phe Tyr Gly Val
```

-continued

```
            20                  25                  30

Pro Ala Trp Arg Asn Ala Thr Ile Pro Leu Phe Cys Ala Thr Lys Asn
        35                  40                  45

Arg Asp Thr Trp Gly Thr Thr Gln Cys Leu Pro Asp Asn Gly Asp Tyr
    50                  55                  60

Ser Glu Val Ala Leu Asn Val Thr Glu Ser Phe Asp Ala Trp Asn Asn
65                  70                  75                  80

Thr Val Thr Glu Gln Ala Ile Glu Asp Val Trp Gln Leu Phe Glu Thr
                85                  90                  95

Ser Ile Lys Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ile Thr
        115                 120                 125

Thr Thr Ala Ser Thr Thr Ser Thr Thr Ala Ser Ala Lys Val Asp Met
    130                 135                 140

Val Asn Glu Thr Ser Ser Cys Ile Ala Gln Asp Asn Cys Thr Gly Leu
145                 150                 155                 160

Glu Gln Glu Gln Met Ile Ser Cys Lys Phe Asn Met Thr Gly Leu Lys
                165                 170                 175

Arg Asp Lys Lys Lys Glu Tyr Asn Glu Thr Trp Tyr Ser Ala Asp Leu
            180                 185                 190

Val Cys Glu Gln Gly Asn Asn Thr Gly Asn Glu Ser Arg Cys Tyr Met
        195                 200                 205

Asn His Cys Asn Thr Ser Val Ile Gln Glu Ser Cys Asp Lys His Tyr
    210                 215                 220

Trp Asp Ala Ile Arg Phe Arg Tyr Cys Ala Pro Pro Gly Tyr Ala Leu
225                 230                 235                 240

Leu Arg Cys Asn Asp Thr Asn Tyr Ser Gly Phe Met Pro Lys Cys Ser
                245                 250                 255

Lys Val Val Val Ser Ser Cys Thr Arg Met Met Glu Thr Gln Thr Ser
            260                 265                 270

Thr Trp Phe Gly Phe Asn Gly Thr Arg Ala Glu Asn Arg Thr Tyr Ile
        275                 280                 285

Tyr Trp His Gly Arg Asp Asn Arg Thr Ile Ile Ser Leu Asn Lys Tyr
    290                 295                 300

Tyr Asn Leu Thr Met Lys Cys Arg Arg Pro Gly Asn Lys Thr Val Leu
305                 310                 315                 320

Pro Val Thr Ile Met Ser Gly Leu Val Phe His Ser Gln Pro Ile Asn
                325                 330                 335

Asp Arg Pro Lys Gln Ala Trp Cys Trp Phe Gly Gly Lys Trp Lys Asp
            340                 345                 350

Ala Ile Lys Glu Val Lys Gln Thr Ile Val Lys His Pro Arg Tyr Thr
        355                 360                 365

Gly Thr Asn Asn Thr Asp Lys Ile Asn Leu Thr Ala Pro Gly Gly Gly
    370                 375                 380

Asp Pro Glu Val Thr Phe Met Trp Thr Asn Cys Arg Gly Glu Phe Leu
385                 390                 395                 400

Tyr Cys Lys Met Asn Trp Phe Leu Asn Trp Val Glu Asp Arg Asn Thr
                405                 410                 415

Ala Asn Gln Lys Pro Lys Glu Gln His Lys Arg Asn Tyr Val Pro Cys
            420                 425                 430

His Ile Arg Gln Ile Ile Asn Thr Trp His Lys Val Gly Lys Asn Val
        435                 440                 445
```

-continued

Tyr Leu Pro Pro Arg Glu Gly Asp Leu Thr Cys Asn Ser Thr Val Thr
    450                 455                 460

Ser Leu Ile Ala Asn Ile Asp Trp Ile Asp Gly Asn Gln Thr Asn Ile
465                 470                 475                 480

Thr Met Ser Ala Glu Val Ala Glu Leu Tyr Arg Leu Glu Leu Gly Asp
                485                 490                 495

Tyr Lys Leu Val Glu Ile Thr Pro Ile Gly Leu Ala Pro Thr Asp Val
            500                 505                 510

Lys Arg Tyr Thr Thr Gly Gly Thr Ser Arg Asn Lys Arg Gly Val Phe
        515                 520                 525

Val Leu Gly Phe Leu Gly Phe Leu Ala Thr Ala Gly Ser Ala Met Gly
    530                 535                 540

Ala Ala Ser Leu Thr Leu Thr Ala Gln Ser Arg Thr Leu Leu Ala Gly
545                 550                 555                 560

Ile Val Gln Gln Gln Gln Gln Leu Leu Asp Val Val Lys Arg Gln Gln
                565                 570                 575

Glu Leu Leu Arg Leu Thr Val Trp Gly Thr Lys Asn Leu Gln Thr Arg
            580                 585                 590

Val Thr Ala Ile Glu Lys Tyr Leu Lys Asp Gln Ala Gln Leu Asn Ala
        595                 600                 605

Trp Gly Cys Ala Phe Arg Gln Val Cys His Thr Thr Val Pro Trp Pro
    610                 615                 620

Asn Ala Ser Leu Thr Pro Lys Trp Asn Asn Glu Thr Trp Gln Glu Trp
625                 630                 635                 640

Glu Arg Lys Val Asp Phe Leu Glu Glu Asn Ile Thr Ala Leu Leu Glu
                645                 650                 655

Glu Ala Gln Ile Gln Gln Glu Lys Asn Met Tyr Glu Leu Gln Lys Leu
            660                 665                 670

Asn Ser Trp Asp Val Phe Gly Asn Trp Phe Asp Leu Ala Ser Trp Ile
        675                 680                 685

Lys Tyr Ile Gln Tyr Gly Val Tyr Ile Val Val Gly Val Ile Leu Leu
    690                 695                 700

Arg Ile Val Ile Tyr Ile Val Gln Met Leu Ala Lys Leu Arg Gln Gly
705                 710                 715                 720

Tyr Arg Pro Val Phe Ser Ser Pro Pro Ser Tyr Phe Gln Gln Thr His
                725                 730                 735

Ile Gln Gln Asp Pro Ala Leu Pro Thr Arg Glu Gly Lys Glu Arg Asp
            740                 745                 750

Gly Gly Glu Gly Gly Gly Asn Ser Ser Trp Pro Trp Gln Ile Glu Tyr
        755                 760                 765

Ile His Phe Leu Ile Arg Gln Leu Ile Arg Leu Leu Thr Trp Leu Phe
    770                 775                 780

Ser Asn Cys Arg Thr Leu Leu Ser Arg Val Tyr Gln Ile Leu Gln Pro
785                 790                 795                 800

Ile Leu Gln Arg Leu Ser Ala Thr Leu Gln Arg Ile Arg Glu Val Leu
                805                 810                 815

Arg Thr Glu Leu Thr Tyr Leu Gln Tyr Gly Trp Ser Tyr Phe His Glu
            820                 825                 830

Ala Val Gln Ala Val Trp Arg Ser Ala Thr Glu Thr Leu Ala Gly Ala
        835                 840                 845

Trp Gly Asp Leu Trp Glu Thr Leu Arg Arg Gly Gly Arg Trp Ile Leu
    850                 855                 860

-continued

Ala Ile Pro Arg Arg Ile Arg Gln Gly Leu Glu Leu Thr Leu Leu
865 870 875

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
ctaatacatc ttctgcatca aacaagtaag t 31

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
aaacaagtaa gt 12

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gcctatccct aaccctctcc 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
cagatggctg gcaactagaa 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic probe
<220> FEATURE:
<221> NAME/KEY: misc_feature
<223> OTHER INFORMATION: 5'- FAM
<220> FEATURE:
<221> NAME/KEY: misc_feature
<223> OTHER INFORMATION: 5' - FAM
<220> FEATURE:
<221> NAME/KEY: misc_feature
<223> OTHER INFORMATION: 3' -NFQ

<400> SEQUENCE: 9
aaacccgctg atcagcctcg a 21

<210> SEQ ID NO 10

-continued

<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accgcctgtt gcgtgtta 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caatcgccaa cgcctcaa 18

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<223> OTHER INFORMATION: 5' -FAM

<400> SEQUENCE: 12
caggccccat cccc 14

UNITED STATES PATENT AND TRADEMARK OFFICE
CERTIFICATE OF CORRECTION

Page 1 of 1

PATENT NO. : 10,010,594 B2
APPLICATION NO. : 15/118421
DATED : July 3, 2018
INVENTOR(S) : Ronald Desrosiers et al.

It is certified that error appears in the above-identified patent and that said Letters Patent is hereby corrected as shown below:

On the Title Page

Item (60), Line 1, "61/061,945," should be -- 62/061,945, --.

In the Claims

At Column 60, Line 55, "NO: I," should be -- NO: 1, --.

At Column 61, Line 10, "WT1," should be -- WTI, --.

Signed and Sealed this
Third Day of September, 2019

Andrei Iancu
*Director of the United States Patent and Trademark Office*